(12) United States Patent
Gazit et al.

(10) Patent No.: US 7,625,707 B2
(45) Date of Patent: Dec. 1, 2009

(54) ANTIBACTERIAL AGENTS AND METHODS OF IDENTIFYING AND UTILIZING SAME

(75) Inventors: Ehud Gazit, Ramat-HaSharon (IL); Izhack Cherny, Tel-Aviv (IL)

(73) Assignee: Ramot At Tel Aviv University Ltd., Tel-Aviv (IL)

( * ) Notice: Subject to any disclaimer, the term of this patent is extended or adjusted under 35 U.S.C. 154(b) by 324 days.

(21) Appl. No.: 10/574,405

(22) PCT Filed: Sep. 27, 2004

(86) PCT No.: PCT/IL2004/000898

§ 371 (c)(1),
(2), (4) Date: Mar. 31, 2006

(87) PCT Pub. No.: WO2005/031362

PCT Pub. Date: Apr. 7, 2005

(65) Prior Publication Data

US 2007/0298043 A1     Dec. 27, 2007

Related U.S. Application Data

(60) Provisional application No. 60/507,488, filed on Oct. 2, 2003, provisional application No. 60/550,334, filed on Mar. 8, 2004.

(51) Int. Cl.
*G01N 33/53* (2006.01)
(52) U.S. Cl. ...................................................... 435/7.1
(58) Field of Classification Search ........................ None
See application file for complete search history.

(56) References Cited

U.S. PATENT DOCUMENTS

| | | | |
|---|---|---|---|
| 2,920,080 A | 1/1960 | Bucourt et al. |
| 3,042,685 A | 7/1962 | Roussel |
| 3,625,973 A | 12/1971 | Julia |
| 3,790,596 A | 2/1974 | Shkilkova et al. |
| 3,791,932 A | 2/1974 | Schuurs et al. |
| 3,839,153 A | 10/1974 | Schuurs et al. |
| 3,850,578 A | 11/1974 | McConnnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,976,639 A | 8/1976 | Batcho et al. |
| 3,984,533 A | 10/1976 | Uzgiris |
| 3,996,345 A | 12/1976 | Ullman et al. |
| 4,034,074 A | 7/1977 | Miles |
| 4,036,945 A | 7/1977 | Haber |
| 4,098,876 A | 7/1978 | Piasio et al. |
| 4,299,917 A | 11/1981 | Berger et al. |
| 4,331,647 A | 5/1982 | Goldenberg |
| 4,626,540 A | 12/1986 | Capps et al. |
| 4,666,828 A | 5/1987 | Gusella |
| 4,683,202 A | 7/1987 | Mullis |
| 4,801,531 A | 1/1989 | Frossard |
| 4,816,567 A | 3/1989 | Cabilly et al. |
| 4,873,316 A | 10/1989 | Meade et al. |
| 4,879,219 A | 11/1989 | Wands et al. |
| 4,925,673 A | 5/1990 | Steiner et al. |
| 4,946,778 A | 8/1990 | Ladner et al. |
| 4,970,233 A | 11/1990 | McHugh |
| 5,011,771 A | 4/1991 | Bellet et al. |
| 5,013,556 A | 5/1991 | Woodle et al. |
| 5,192,659 A | 3/1993 | Simons |
| 5,210,215 A | 5/1993 | Politi et al. |
| 5,270,163 A | 12/1993 | Gold et al. |
| 5,272,057 A | 12/1993 | Smulson et al. |
| 5,281,521 A | 1/1994 | Trojanowski et al. |
| 5,304,470 A | 4/1994 | Fischer et al. |
| 5,332,648 A | 7/1994 | Kihara et al. |
| 5,475,096 A | 12/1995 | Gold et al. |
| 5,545,806 A | 8/1996 | Lonberg et al. |
| 5,545,807 A | 8/1996 | Surani et al. |
| 5,556,744 A | 9/1996 | Weiner et al. |
| 5,567,588 A | 10/1996 | Gold et al. |
| 5,569,825 A | 10/1996 | Lonberg et al. |
| 5,595,877 A | 1/1997 | Gold et al. |

(Continued)

FOREIGN PATENT DOCUMENTS

DE           3412445           10/1985

(Continued)

OTHER PUBLICATIONS

Altland et al. "Potential Treatment of Transthyretin-Type Amyloidoses by Sulfite", Neurogenetics, 2: 183-188, 1999.
Appukkuttan et al. "Microwave Enhanced Formation of Electron Rich Arylboronates", Synlett, 8: 1204-1206, 2003. Figs. Scheme 4, Compounds 5A, 5B, 5C, 5D.
Azriel et al. "Analysis of the Minimal Amyloid-Forming Fragment of the Islet Amyloid Polypeptide", The Journal of Biological Chemistry, 276(36): 34156-34161, 2001.
Balaram "De Novo Design; Backbone Conformational Constraints in Nucleating Helices and β-hairpins", J. Peptide Res., 54: 195-199, 1999.
Berson et al. "Proprotein Convertase Cleavage Liberates A Fibrillogenic Fragment of A Resident Glycoprotein to Initiate Melanosome Biogenesis", Journal of Cell Biology, 161(3): 521-533, 2003.
Bong et al. "Self-Assembling Organic Nanotubes", Angewandte Chemie, International Edition,40:988-1011, 2001.

(Continued)

*Primary Examiner*—Robert A Zeman
*Assistant Examiner*—Nina A Archie

(57) ABSTRACT

A method of identifying a molecule capable of inducing death of a bacterial cell which includes exposing toxin and antitoxin polypeptides of a toxin-antitoxin pair produced by the bacterial cell to a plurality of molecules, and identifying a molecule of the plurality of molecules capable of preventing or disrupting binding between the antitoxin and said toxin polypeptides, thereby identifying the molecule capable of inducing death of the bacterial cell.

1 Claim, 16 Drawing Sheets
(2 of 16 Drawing Sheet(s) Filed in Color)

U.S. PATENT DOCUMENTS

| | | |
|---|---|---|
| 5,625,126 A | 4/1997 | Lonberg et al. |
| 5,633,425 A | 5/1997 | Lonberg et al. |
| 5,637,459 A | 6/1997 | Burke et al. |
| 5,643,768 A | 7/1997 | Kawasaki |
| 5,658,754 A | 8/1997 | Kawasaki |
| 5,659,041 A | 8/1997 | Pollak et al. |
| 5,661,016 A | 8/1997 | Lonberg et al. |
| 5,683,867 A | 11/1997 | Biesecker et al. |
| 5,688,561 A | 11/1997 | Ichikawa et al. |
| 5,705,337 A | 1/1998 | Gold et al. |
| 5,916,642 A | 6/1999 | Chang |
| 6,162,828 A | 12/2000 | Fukuda et al. |
| 6,251,625 B1 | 6/2001 | Bommarius et al. |
| 6,255,286 B1 | 7/2001 | Yanai et al. |
| 6,261,569 B1 | 7/2001 | Comis et al. |
| 6,303,567 B1 | 10/2001 | Findeis et al. |
| 6,309,669 B1 | 10/2001 | Setterstrom et al. |
| 6,326,174 B1 | 12/2001 | Joyce et al. |
| 6,359,112 B2 | 3/2002 | Kapurniotu et al. |
| 6,361,861 B2 | 3/2002 | Gao et al. |
| 6,472,436 B1 | 10/2002 | Schubert et al. |
| 6,593,339 B1 | 7/2003 | Eek et al. |
| 6,610,478 B1 | 8/2003 | Takle et al. |
| 6,613,875 B1 | 9/2003 | Ghadiri |
| 6,617,114 B1 | 9/2003 | Fowlkes et al. |
| 6,677,153 B2 | 1/2004 | Iversen |
| 6,689,753 B1 | 2/2004 | Soto-Jara |
| 6,858,318 B2 | 2/2005 | Kogiso et al. |
| 6,976,639 B2 | 12/2005 | Williams et al. |
| 7,045,537 B1 | 5/2006 | Woolfson et al. |
| 2001/0041732 A1 | 11/2001 | Gurley et al. |
| 2002/0006954 A1 | 1/2002 | Hensley et al. |
| 2002/0086067 A1 | 7/2002 | Choi et al. |
| 2002/0151506 A1 | 10/2002 | Castillo et al. |
| 2003/0130484 A1 | 7/2003 | Gordon et al. |
| 2003/0158237 A1 | 8/2003 | Saragovi et al. |
| 2003/0225155 A1 | 12/2003 | Fernandez-Pol et al. |
| 2004/0029830 A1 | 2/2004 | Hebert |
| 2004/0052928 A1 | 3/2004 | Gazit |
| 2004/0152672 A1 | 8/2004 | Carson et al. |
| 2005/0020809 A1 | 1/2005 | Gazit |
| 2005/0069950 A1 | 3/2005 | Haynie |
| 2006/0079454 A1 | 4/2006 | Reches et al. |
| 2006/0194777 A1 | 8/2006 | Gazit et al. |
| 2006/0234947 A1 | 10/2006 | Gazit |
| 2007/0021345 A1 | 1/2007 | Gazit |
| 2007/0135334 A1 | 6/2007 | Gazit |
| 2008/0305040 A1 | 12/2008 | Klunk |

FOREIGN PATENT DOCUMENTS

| | | |
|---|---|---|
| DE | 10043282 | 3/2002 |
| EP | 0081122 | 6/1983 |
| EP | 0264166 | 4/1988 |
| EP | 0421946 | 4/1991 |
| EP | 0885904 | 3/2004 |
| EP | 966975 | 9/2005 |
| JP | 63-044895 | 2/1988 |
| JP | 02-295923 | 12/1990 |
| JP | 10-245342 | 9/1998 |
| WO | WO 80/00789 | 1/1980 |
| WO | WO 92/19253 | 11/1992 |
| WO | WO 97/16191 | 5/1997 |
| WO | WO 98/20135 | 5/1998 |
| WO | WO 99/42102 | 8/1999 |
| WO | WO 99/58652 | 11/1999 |
| WO | WO 00/24390 | 5/2000 |
| WO | WO 01/05421 * | 1/2001 |
| WO | WO 01/05421 A1 * | 1/2001 |
| WO | WO 01/10457 | 2/2001 |
| WO | WO 01/45726 | 6/2001 |
| WO | WO 01/49281 | 7/2001 |
| WO | WO 01/49307 | 7/2001 |
| WO | WO 01/93836 | 12/2001 |
| WO | WO 02/072086 | 9/2002 |
| WO | WO 02/094857 | 11/2002 |
| WO | WO 03/013442 | 2/2003 |
| WO | WO 03/024443 | 3/2003 |
| WO | WO 03/039540 | 5/2003 |
| WO | WO 03/063760 | 7/2003 |
| WO | WO 03/070269 | 8/2003 |
| WO | WO 03/077866 | 9/2003 |
| WO | WO 2004/052773 | 6/2004 |
| WO | WO 2004/060791 | 7/2004 |
| WO | WO 2005/016339 | 2/2005 |
| WO | WO 2005/020809 | 3/2005 |
| WO | WO 2005/027901 | 3/2005 |
| WO | WO 2005/031362 | 4/2005 |
| WO | WO 2005/000193 | 6/2005 |
| WO | WO 2005/085867 | 9/2005 |
| WO | WO 2006/013552 | 2/2006 |
| WO | WO 2006/018850 | 2/2006 |
| WO | WO 2006/020681 | 2/2006 |
| WO | WO 2006/027780 | 3/2006 |
| WO | WO 2006/006172 | 6/2006 |
| WO | WO 2007/029003 | 3/2007 |
| WO | WO 2007/043048 | 4/2007 |

OTHER PUBLICATIONS

Chapman et al. "Role of *Escherichia coli* Curli Operons in Directing Amyloid Fiber Formation", Science, 295(5556): 851-855, 2002, Abstract.

Cherny et al. "The YefM Antitoxin Defines A Family of Natively Unfolded Proteins", The Journal of Biological Chemistry, 279(9): 8252-8261, 2004.

Chou et al. "Empirical Predictions of Protein Conformation", Ann. Rev. Biochem., 47: 251-276, 1978.

Claessen et al. "A Novel Class of Secreted Hydrophodic Proteins is Involved in Aerial Hyphae Formation in *Streptomyces coelicolor* by Forming Amyloid-Like Fibrils", Genes & Development, 17: 1714-1726, 2003.

Clark et al. "Self-Assembling Cyclic β3-Peptide Nanotubes as Artificial Transmembrane Ion Channels", Journal of the American Chemical Society, JACS, 120: 651-656, 1998.

Cohen et al "Inhibition of Amyloid Fibril Formation and Cytotoxicity by Hydroxyindole Derivatives", Biochemistry, 45: 4727-4735, 2006. Abstract, p. 4728, col. 1, Last §, p. 4728, col. 2, § 2, Fig.1, p. 4729, col. 1, p. 4728, col. 1, Last §, p. 4728, col. 2, § 2, Fig.1, p. 4728, col. 1, Last §, p. 4728, col. 2, § 2, Fig.1, 4, p. 4732, col. 2, § 2,3, p. 4733, col. 2, § 4.

Elliot et al. "The Chaplins: A Family of Hydrophobic Cell-Surface Proteins Involved in Aerial mycelium Formation in *Streptomyces coelicolor*", Genes & Development, 17: 1727-1740, 2003.

Engelberg-Kulka et al. "Bacterial Programmed Cell Death Systems as Targets for Antibiotics", Trends in Microbiology, 12(2): 66-71, 2004.

Gazit "Mechanisms of Amyloid Fibril Self-Assembly and Inhibition Model Short Peptides as A Key Research Tool", The FEBS Journal, 272: 5971-5978, 2005.

Gazit "Mechanistic Studies of Process of Amyolid Fibrils Formation by the Use of Peptide Fragments and Analogues: Implications for the Design of Fibrillization Inhibitors", Current Medicinal Chemistry, 9: 1725-1735, 2002.

Ghadiri et al. "Artificial Transmembrane Ion Channels From Self-Assembling Peptide Nanotubes", Nature, 369(6478): 301-304, 1994.

Grady et al. "Axe-Txe, A Broad-Spectrum Proteic Toxin-Antitoxin System Specified by A Multidrug-Resistant, Clinical Isolate of *Enterococcus faecium*", Molecular Biology, 47(5): 1419-1432, 2003. Abstract, p. 1424, col. 1—p. 1426, col. 2, Fig.5.

Higaki et al. "Regulation of Drug Absorption From Small Intestine by Enteric Nervous System I: A Poorly Absorbable Drug Via Passive Diffusion", Drug Metabolism and Pharmacokinetics, 19(3): 198-205, 2004.

Holmes et al. "Extensive Neurite Outgrowth and Active Synapse Formation on Self-Assembling Peptide Scaffolds", Proc. Natl. Acad. Sci. USA, 97(12): 6728-6733, 2000.

Hoyle et al. "*Pseudomonas aeruginosa* Biofilm as A Diffusion Barrier to Piperacillin", Antimicrobial Agents and Chemotherapy, 36(9): 2054-2056, 1992.

Huang et al. "A Review on Polymer Nanofibers by Electrospinning and Their Applications in Nanocomposites", Composites Science and Technology, 63: 2223-2253, 2003.

Inglot "Comparison of the Antiviral Activity in Vitro of Some Non-Steroidal Anti-Inflammatory Drugs", Journal of General Virology, 4(2): 203-214, 1969.

Jack et al. "The Organization of Aromatic Side Groups in An Amyloid Fibril Probed by Solid-State 2H and 19F NMR Spectroscopy", Journal of the American Chemical Society, JACS, 128: 8098-8099, 2006.

Jayawarna et al. "Nanostructured Hydrogels for Three-Dimensional Cell Culture Through Self-Assembly of Fluorenylmethoxycarbonyl-Dipeptides", Advanced Materials, 18: 611-614, 2006.

Jin "Electrospinning *Bombyx mori* Silk With Poly (Ethylene Oxide)" Biomacromolecules, 3: 1233-1239, 2002.

Kaplan "Fibrous Proteins-Silk as a Model System", Polymer Degradation and Stability, 59: 25-32, 1998.

Kimura et al. "Analysis and Prediction of Absorption Profile Including Hepatic First-Pass Metabolism of N-Methyltyramine, A Potent Stimulant of Gastrin Release Present in Beer, After Oral Ingestion in Rats by Gastrointestinal-Transit-Absorption Model", Drug Metabolism and Disposition, 28(5): 577-581, 2000.

Kisilevsky et al. "Arresting Amyloidosis In Vivo Using Small-Molecule Anionic Sulphonates or Sulphates: Implications for Alzheimer's Disease", Nature Medicine, 1: 143-148, 1995. Abstract.

Kocisko et al. "New Inhibitors of Scrabie-Associated Prion Protein Formation in A Library of 2,000 Drugs and Natural Products", Journal of Virology, 77(19): 10288-10294, 2003.

Kon-Ya et al "Indole Derivatives as Potent Inhibitors of Larval Settlement by the Barnacle, *Balanus amphitrite*", Bioscience Biotechnology Biochemistry, JP, 58(12): 2178-2181, 1994. Compound 102.

Kubik "High-Performance Fibers from Spider Silk", Angewandte Chemie, International Edition 41(15): 2721-2723, 2002.

Lashuel et al. "New Class of Inhibitors of Amyloid-? Fibril Formation. Implications for the Mechanism of Pathogenesis in Alzheimer's Disease", The Journal of Biological Chemistry, 277(45): 42881-42890, 2002.

Lazaris et al. "Spider Silk Fibers Spun From Soluble Recombinant Silk Produced in Mammalian Cells", Science, 295: 472-476, 2002. p. 474-475.

Lee et al. "Anti-Diabetic Constituent From the Node of Lotus Rhizome (*Nelumbo nucifera gaertn*)", Natural Product Sciences, 7(4), 107-109, 2001. p. 108, col. 1, Last §—col. 2, § 1.

Lee et al. "Virus-Based Febrication of Micro- and Nanofibers Using Electrospinnig" Nano Letters,4(3): 387-390, 2004.

Liao et al. "Triphenylmethane Dyes as Inhibitors of Reverse Transcriptase RNA Polymerase and Protein Synthesis: Structure Activity Relationships", Journal of Medicinal Chemistry, 18(1): 117-120, 1975. Abstract.

Losert et al. "Effect of Indole 3 Alkanecarboxylic Acifs on Glucose Utilization in Rats" Arzneimittel-Forschung/Drug Research, 25(6): 880-887, 1975. p. 880, col. 1, § 6, p. 886, col. 2, § 4, 5, p. 887, col. 1, § 3.

Mah et al. "A Genetic Basis for *Pseudomonas aeruginosa* Biofilm Antibiotic Resistance", Nature, 426: 306-310, 2003.

Mahler et al. "Rigid, Self-Assembled Hydrogel Composed of A Modified Aromatic Dipeptide", Advanced Materials, 18(11): 1365-1370, 2006.

Matsui et al. "Crystalline Glyclylglycine Bolaamphiphile Tubules and Their pH-Sensitive Structural Transformation" The Journal of Physical Chemistry B, 104(15): 3384-3386, 2000.

Meluleni et al. "Mucoid *Pseudomonas aeruginosa* Growing in A Biofilm in Vitro are Killed by Opsonic Antibodies to the mucoid Exopolysaccharide Capsule but Not by Antibodies Produced During Chronic Lung Infection in Cystic Fibrosis Patients[1],[2]", Journal of Immunology, 155:2029-2038, 1995.

Murphy et al. "Biofilm Formation by Nontypeable Haemophilus Influenzae: Strain variability, Outer Membrane Antigen Expression and Role of pili", BMC Microbiology, 2(7): 1471-2180, 2002.

Nakajima "Amine Precursor Therapy: Manipulation of Brain Amine Activity With Precursor Amino Acid", Psychiatry and Clinical Neurosciences, 51(5), 267-274, 1997. p. 269, col. 1, § 2, 3.

Oza et al. "Synthesis and Evaluation of Anthranilic Acid-Based Transthyretin Amyloid Fibiril Inhibitors", Bioorganic & Medicinal Chemistry Letters, 9: 1-6, 1999.

Pavia et al. "Antimicrobial Activity of Nicotine Against A Spectrum of Bacterial and Fungal Pathogens", Journal of Medical Microbiology, 49(7): 675-676, 2000.

Peterson et al. "Inhibiting Transthyretin Conformational Chamges That Lead to Amyloid Fibril Formation", Proc. Natl. Acad. Sci. USA, 95: 12956-12960, 1998.

Pispisa et al. "A Spectroscopic and Molecular Mechanics Investigation on A Series of AIB-Based Linear Peptides and A Peptide Template, Both Containing Tryptophan and A Nitroxide Derivative as Probes", Biopolymers, 53: 169-181, 2000.

Reches et al. "Designed Aromatic Homo-Dipeptides: Formation of Ordered Nanostructures and Potential Nanotechnological Applications", Physical Biology, 3: S10-S19, 2006.

Reches et al. "Self-Assembly of Peptide Nanotubes and Amylois-Like Structures by Charged-Termini-Capped Diphenylalanine Peptide Analogues", Israel Journal of Chemistry, 45(3): 363-371, 2005.

Reches et al. "Supporting Online Material", Science, 300(5619): 1-9, 2003. Retrieved From the Internet: URL:http://www.sciencemag.org/cgi/data/300/5619/625/DC1.

Sacchettini et al. "Therapeutic Strategies for Human Amyloid Diseases", Nature Reviews, 1: 267-275, 2002.

Stewart "Theoretical Aspects of Antibiotic Diffusion Into Microbial Biofilms", Antimicrobial Agents and Chemotherapy, 40(11): 2517-2522, 1996.

Toledano et al. "Enzyme-Triggered Self-Assembly of Peptide Hydrogels Via Reversed Hydrolysis", Journal of the American Chemical Society, JACS, 128(4): 1070-1071, 2006.

True et al. "Epigenetic Regulation of Trenslation Reveals Hidden Genetic Variation to Produce Complex Traits", Nature, 431: 184-187, 2004.

Tsai et al. "Synthesis of AIB-Containing Peptidomimetics as Potential Inhibitors of Alzheimer's γ-Secretase", 218th ACS National Meeting, New Orleans, USA, Meeting Abstract, MEDI-018, 1999. Abstract.

Tsang et al. "A Simple Chemical Method of Opening and Filling Carbon Nanotubes", Nature, 372: 159-162, 1994.

Tuite et al. "Propagation of Yeast Prions", Nature Reviews, 4: 878-889, 2003.

Vauthey et al. "Molecular Self-assembly of Surfactant-Like Peptides to form Nanotubes and Nanovesicles", PNAS,99(8):5355-5360, 2002.

Westwater et al. "Use of Genetically Engineered Phage to Deliver Antimicrobial Agents to Bacteria: An Alternative Therapy for Treatment of Bacterial Infections", Antimicrobial Agents and Chemotherapy, 47 (4): 1301-1307, 2003.

Yokoi et al. "Dynamic Reassembly of Peptide RADA16 Nanofiber Scaffold", Proc. Natl. Acad. Sci. USA, 102(24): 8414-8419, 2005.

Zhang et al. "Supramolecular Hydrogels Respond to Ligand-Receptor Interaction", Journal of the American Chemical Society, 125(45): 13680-13681, 2003.

Akazome et al. "Enantioselective Inclusion of Methyl Phenyl Sulfoxides and Benzyl Methyl Sulfoxides by (R)-Phenylglycyl-(R)-Phenylglycine and the Crystal Structures of the Inclusion Cavities", Journal of Organic Chemistry, 65(1): 68-76, 2000.

Anguiano et al. "Protofibrillar Islet Amyloid Polypeptide Permeabilizes Synthetic Vesicles by A Pore-Like Mechanism That May Be Relevant to Type II Diabetes", Biochemistry, 41: 11338-11343, 2002.

Arvinte et al. "The Structure and Mechanism of Formation of Human Calcitonin Fibrils", The Journal of Biological Chemistry, 268(9): 6415-6422, 1993.

Austin et al. "Medical Progress: Calcitonin. Physiology and Pathophysiology", The New England Journal of Medicine, 304(5): 269-278, 1981.

Balbach et al. "Supramolecular Structure in Full-Length Alzheimer's β-Amyloid Fibrils: Evidence for A Parallel β-Sheet Organization From Solid-State Nuclear Magnetic Resonance", Biophysical Journal, 83: 1205-1216, 2002.

Bauer et al. "Interfacial Adsorption and Aggregation Associated Changes in Secondary Structure of Human Calcitonin Monitored by ATR-FTIR Spectroscopy", Biochemistry, 33: 12276-12282, 1994.

Benvenga et al. "Homology of Calcitonin With the Amyloid-Related Proteins", Journal of Endocrinological Investigation, 17: 119-122, 1994.

Berger et al. "Calcitonin-Like Immunoreactivity of Amyloid Fibrils in Medullary Thyroid Carcinomas", Virchows Archiv A Pathological Anatomy and Histopathology, 412: 543-551, 1988.

Bird et al. "Single-Chain Antigen-Binding Proteins", Science, 242(4877): 423-426, 1988.

Boerner et al. "Production of Antigen-Specific Human Monoclonal Antibodies From In Vitro-Primed Human Splenocytes", The Journal of Immunology, 147(1): 86-95, 1991.

Cherny et al. "The Formation of *Escherichia coli* Curli Amyloid Fibrils is Mediated by Prion-Like Peptide Repeats", Journal of Molecular Biology, 352(2): 245-252, 2005.

Cherny et al. "The YefM Antitoxin Defines A Family of Natively Unfolded Proteins", The Journal of Biological Chemistry, 279(9): 8252-8261, 2004.

Choplin "Computers and the Medicinal Chemist", Comprehensive Medicinal Chemistry, 4(Chap.17.2): 33-58, 1990.

Chou et al. "Conformational Parameters for Amino Acids in Helical, β-Sheet, and Random Coil Regions Calculated From Proteins", Biochemistry, 13(2): 211-222, 1974.

Claessens et al. "Review Commentary: π-π Interactions in Self-Assembly", Journal of Physical Organic Chemistry, 10: 254-272, 1997.

Cole et al. "The EBV-Hybridoma Technique and Its Application to Human Lung Cancer", Monoclonal Antibodies and Cancer Therapy, Proceedings of the Roche-UCLA Symposium, Park City, Utah, p. 77-96, 1985.

Copp "Endocrine Regulation of Calcium Metabolism", Annual Reviews in Physiology, 32: 61-86, 1970.

Engelberg-Kulka et al. "Bacterial Programmed Cell Death Systems as Targets for Antibiotics", Trends in Microbiology, vol. 12 (2): p. 66-71, 2004.

Findeis et al. "Modified-Peptide Inhibitors of Amyloid β-Peptide Polymerization", Biochemistry, 38: 6791-6800, 1999.

Fingl et al. "Inroduction: General Principles", The Pharmacological Basis of Therapeutics, 5th Ed., Sec.I(Chap.1): 1-53, 1975.

Fishwild et al. "High-Avidity Hum IgGκ Monoclonal Antibodies From A Novel Strain of Minilocus Transgenic Mice", Nature Biotechnology, 14: 845-851, 1996.

Forloni et al. "Anti-Amyloidogenic Activity of Tetracyclines: Studies in Vitro", FEBS Letters, 487(3): 404-407, 2001. Figs. 1,3.

Gillard et al. "Controlling Self-Assembly", Chemical European Journal, 3(12): 1933-1940, 1997.

Görbitz "Nanotube Formation by Hydrophobic Dipeptides", Chemistry, 7(23): 5153-5159, 2001, Abstract.

Grady et al. "Axe—Txe, A Broad-Spectrum Proteic Toxin—Antitoxin System Specified by a Multidrug-Resistant, Clinical Isolate of *Enterococcus faecium*" Molecular Microbiology, vol. 47(5: p. 1419-1432, 2003.

Grateau "[Coli's Curli or How Amyloid Can be Physiological.]", Médecine Sciences, 18(6-7): p. 664, 2002.

Häggqvist et al. "Medin: An Integral Fragment of Aortic Smooth Muscle Cell-Produced Lactadherin Forms the Most Common Human Amyloid", Proc. Natl. Acad. Sci. USA, 96: 8669-8674, 1999.

Haldar et al. "First Crystallographic Signature of the Highly Ordered Supramolecular Helical Assemblage From A Tripeptide Containing a Non-Coded Amino Acid", Tetrahedron Letters, 43(14): 2653-2656, 2002. Abstract.

Harlow et al. "Antibodies: A Laboratory Manual", Cold Spring Harbor Laboratory, p. III-IX, 1988.

Harrison et al. "Amyloid Peptides and Proteins in Review", Reviews in Physiology, Biochemistry and Pharmacology, 159: 1-77, 2007.

Hartgerink et al. "Peptide Nanotubes and Beyond", Chemistry European Journal, 4(8): 1367-1372, 1998. Abstract.

Hoogenboom et al. "By-Passing Immunisation. Human Antibodies From Synthetic Repertoires of Germline VH Gene Segments Rearranged In Vitro", Journal of Molecular Biology, 227: 381-388, 1992.

Inbar et al. "Localization of Antibody-Combining Sites Within the Variable Portions of Heavy and Light Chains", Proc. Natl. Acad. Sci. USA, 69(9): 2659-2662, 1972.

Jones et al. "Replacing the Complementarity-Determining Regions in A Human Antibody With Those From A Mouse", Nature, 321: 522-525, 1986.

Kamihira et al. "Conformational Transitions and Fibrillation Mechanism of Human Calcitonin as Studied by High-Resolution Solid-State 13C NMR [in Process Citation]", Protein Science, 9: 867-877, 2000.

Kanaori et al. "Study of human Calcitonin Fibrillation by Proton Nuclear Magnetic Resonance Spectroscopy", Biochemistry, 34: 12138-12143, 1995.

Kapurniotu et al. "Structure-Based Design and Study of Non-Amyloidogenic, Double N-Methylated IAPP Amyloid Core Sequences as Inhibitors of IAPP Amyloid Formation and Cytotoxicity", Journal of Molecular Biology, 315: 339-350, 2002.

Kedar et al. "In Vitro Synthesis of 'Amyloid' Fibrils From Insulin, Calcitonin and Parathormone", Israel Journal of Medical Science, 12(10): 1137-1140, 1976.

Kyte et al. "A Simple Method for Displaying the Hydropathic Character of A Protein", Journal of Molecular Biology, 157: 105-132, 1982.

Lansbury "Following Nature's Anti-Amyloid Strategy", Nature Biotechnology 19(2): 112-113, 2001. p. 112, Left-Hand col., Paragraph 1—Middle col., Paragraph 1.

Larrick et al. "PCR Amplification of Antibody Genes", Methods: A Companion to Methods in Enzymology, 2(2): 106-110, 1991.

Lonberg et al. "Antigen-Specific Human Antibodies From Mice Comprising Four Distinct Genetic Modifications", Nature, 368(6474): 856-859, 1994.

Lonberg et al. "Human Antibodies From Transgenic Mice", International Review of Immunology, 13: 65-93, 1995.

Lowe et al. "Structure-Function Relationships for Inhibitors of β-Amyloid Toxicity Containing the Recognition Sequence KLVFF", Biochemistry, 40: 7882-7889, 2001.

Lyon et al. "Self-Assembly and Gelation of Oxidized Gluthathione in Organic Solvents", Journal of the American Chemical Society, 123: 4408-4413, 2001.

Maji et al. "Fibril-Forming Model Synthetic Peptides Containing 3-Aminophenylacetic Acid", Tetrahedron, 58(43): 8695-8702, 2002, Abstract.

Marks et al. "By-Passing Immunization—Human Antibodies from V-Gene Libraries Displayed on Phage", Journal of Molecular Biology, 222: 581-597, 1991.

Marks et al. "By-Passing Immunization: Building High Affinity Human Antibodies by Chain Shuffling", Bio/Technology, 10: 779-783, 1992.

Maury et al. "Creation of Amyloid Fibrils From Mutant ASN187 Gelsolin Peptides", Biochemical and Biophysical Research Communications, 183(1): 227-231, 1992.

McGaughey et al. "π-Stacking Interactions", The Journal of Biological Chemistry, 273(25): 15458-15463, 1998.

Morrison "Success in Specification", Nature, 368(6474): 812-813, 1994.

Mosmann "Rapid Colorimetric Assay for Cellular Growth and Survival: Application to Proliferation and Cytotoxicity Assays", Journal of Immunological Methods, 65: 55-63, 1983.

Mosselman et al. "The Complete Islet Amyloid Polypeptide Precursor Is Encoded by Two Exons", FEBS Letters, 247: 154-158, 1989, Database Accession No. S04016.

Mutter "Studies on the Coupling Rates in Liquid-Phase Peptide Synthesis Using Competition Experiments", International Journal of Peptide Protein Research, 13: 274-277, 1979.

Neuberger "Generating High-Avidity Human Mabs in Mice", Nature Biotechnology, 14: 826, 1996.

Nicolaus "Symbiotic Approach to Drug Design", Decision Making in Drug Research, p. 173-186, 1983.

Offen et al. "A Low Molecular Weight Copper Chelator Crosses the Blood-Brain Barrier and Attenuates Experimental Autoimmune Encephalomyelitis", Journal of Neurochemistry, 89: 1241-1251, 2004.

Pack et al. "Improved Bivalent Miniantibodies, With Identical Avidity as Whole Anitbodies, Produced by High Cell Density Fermentation of *Escherichia coli*", Bio/Technology, 11: 1271-1277, 1993.

Petkova et al. "A Structural Model for Alzheimer's β-Amyloid Fibrils Based on Experimental Constraints From Solid State NMR", Proc. Natl. Acad. Sci. USA, 99(26): 16742-16747, 2002.

Pettmann et al. "Morphological and Biochemical Maturation of Neurones Cultured in the Absence of Glial Cells", Nature, 281: 378-380, 1979.

Porter "The Hydrolysis of Rabbit γ-Globulin and Antibodies With Crystalline Papain", Biochemical Journal, 73: 119-126, 1959.

Presta "Antibody Engineering", Current Opinion in Structural Biology, 2: 593-596, 1992.

Puchtler et al. "A Review of Early Concepts of Amyloid in Context With Contemporary Chemical Literature From 1839 to 1859", The Journal of Histochemistry and Cytochemistry, 14(2): 123-134, 1966.

Reches et al. "Amyloid Fibril Formation by Pentapeptide and Tetrapeptide Fragments of Human Calcitonin", The Journal of Biological Chemistry, 277(38): 35475-35480, 2002.

Reches et al. "Casting Metal Nanowires Within Discrete Self-Assembled Peptide Nanotubes", Science, 300(5619): 625-627, 2003, Abstract.

Riechmann et al. "Reshaping Human Antibodies for Therapy", Nature, 332: 323-329, 1988.

Shetty et al. "Aromatic π-Stacking in Solution as Revealed Through the Aggregation of Phenylacetylene Macrocycles", Journal of the American Chemical Society, 118: 1019-1027, 1996.

Sigel-Causey et al. "Phylogeny of the Pelecaniformes: Molecular Systematics of A Privative Group", Avian Molecular Evolution and Systematics, academic Press, p. 159-171, NBCI GenBank, Accession No. AAB58518, 1997.

Solomon et al. "Disaggregation of Alzheimer β-Amyloid by Site-Directed MAb", Proc. Natl. Acad. Sci. USA, 94: 4109-4112, 1997.

Sun et al. "Aromatic Van der Waals Clusters: Structure and Nonrigidity", Journal of Physical Chemistry, 100: 13348-13366, 1996.

Tjernberg et al. "Arrest of β-Amyloid Fibril Formation by A Pentapeptide Ligand", The Journal of Biological Chemistry, 271(15): 8545-8548, 1996.

Tjernberg et al. "Controlling Amyloid β-Peptide Fibril Formation With Protease-Stable Ligands", The Journal of Biological Chemistry, 272(19): 12601-12605, 1997.

Tonkinson et al. "Antisense Oligodeoxynucleotides as Clinical Therapeutic Agents", Cancer Investigation, 14(1): 54-65, 1996.

Verhoeyen et al. "Reshaping Human Antibodies: Grafting An Antilysozyme Activity", Science, 239: 1534-1536, 1988.

Vidal et al. "A Stop-Codon Mutation in the BRI Gene Associated With Familial British Dementia", Nature, 399: 776-781, 1999.

Whitlow et al. "Single-Chain Fv Proteins and Their Fusion Proteins", Methods: A Companion to Methods in Enzymology, 2(2): 97-105, 1991.

Wolfenden et al. "Affinities of Amino Acid Side Chains for Solvent Water", Biochemistry, 20: 849-855, 1981.

Zaidi et al. "Forty Years of Calcitonin—Where Are We Now? A Tribute to the Work of Iain Macintyre, FRS", Bone, 30(5): 655-663, 2002.

International Search Report Dated May 1, 2004 From International Searching Authority Re.: Application No. PCT/IL2004/000012.

International Search Report Dated Aug. 16, 2005 From the International Searching Authority Re.: Application No. PCT/IL2004/000898.

International Search Report Dated Jul. 19, 2004 From the International Searching Authority Re.: Application No. PCT/IL03/01045.

Notice of Allowance Dated Sep. 16, 2008 From the US Patent Office Re.: U.S. Appl. No. 11/148,262.

Office Action Dated Sep. 15, 2008 From the Israeli Patent Office Re.: Application No. 169121 and Its Translation Into English.

Office Action Dated Sep. 15, 2008 From the Israeli Patent Office Re.: Appliction No. 169120 and Its Translation Into English.

Official Action Dated Dec. 12, 2008 From the US Patent and Trademark Office Re.: U.S. Appl. No. 11/656,542.

Official Action Dated Dec. 16, 2008 From the US Patent and Trademark Office Re.: U.S. Appl. No. 10/562,852.

Written Opinion Not Dated From the International Searching Authority Re.: Application No. PCT/IL2004/000898, Apr. 14, 2004.

Reza et al "Self-assembling Organic Nanotubes Based on a Cyclic Peptide Architecture", Nature 366:324-327 (1993).

Sano "Prevention of Alzheimer's Disease: Where We Stand", Current Neurology and Neuroscience Reports, 2(5): 392-399, Oct. 2002. Abstract.

Hartgerink et al. "Self-Assembling Peptide Nanotubes", Journal of the American Chemical Society, 118: 43-50, 1996.

Ajayan et al. "Applications of Carbon Nanotubes", Topics of Applied Physics, 80: 391-425, 2001.

Booth et al. "Instability, Unfolding and Aggregation of Human Lysozyme Variants Underlying Amyloid Fibrillogenesis", Nature, 385: 787-793, 1997.

Glenner "Amyloid Deposits and Amyloidosis. The Beta-Fibrilloses (First of Two Parts)", The New England Journal of Medicine, 302(23): 1283-1292, 1980.

Ferrannini "Insulin Resistance Versus Insulin Deficiency in Non-Insulin-Dependent Diabetes Mellitus: Problems and Prospects", Endocrine Reviews, 19(4): 477-490, 1998.

Westermark "Amyloid and Polypeptide Hormones: What is Their Interrelationship?", Amyloid Int. J. Exp. Clin. Invest, 1:47-60, 1994.

Westermark "Islet Amyloid Polypeptide: Pinpointing Amino Acid Residues Linked to Amyloid Fibril Formation", Proc. Natl. Acad. Sci. USA, 87: 5036-5040, 1990.

Johnson et al. "Islet Amyloid, Islet-Amiloid Polypeptide, and Diabetes Mellitus", The New England Journal of Medicine, 321(8): 513-518, 1989.

Mosselman et al. "Islet Amyloid Polipeptide: Identification and Chromosomal Localization of the Human Gene", FEBS Letters, 239(2): 227-232, 1988.

Moriatry et al. "Effects of Sequential Proline Substitutions on Amoyloid Formation by Human Amylin20-29", Biochemistry, 38: 1811-1818, 1999.

Höppener et al. "Islet Amyloid and Type 2 Diabetes Mellitus", The New England Journal of Medicine, 343(6): 411-419, 2000.

Seino "S20G Mutation of the Amylin Gene Is Associated With Type II Diabetes in Japanes", Diabetologia, 44: 906-909, 2001.

Gillmore et al. "Amyloidosis A Review of Recent Diagnostic and Therapeutic Developments", British Journal of Haematology, 99: 245-256, 1997.

Kulkarni et al. "Investigation of the Efffect of Antisense Oligodeoxynucleotides to Islet Amyloid Polypeptide mRNA on Insulin Release, Content and Expression", Journal of Endocrinology, 151: 341-348, 1996.

Novials et al. "Reduction of Islet Amylin Expression and Basal Secretion by Adenovirus-Mediated Delivery of Amylin Antisense cDNA", Pancreas, 17(2): 182-186, 1998.

Kahn et al. "Islet Amyloid: A Long-Recognized But Underappreciated Pathological Feature of Type 2 Diabetes", Diabetes, 48: 241-253, 1999.

Merlini et al. "Intereaction of the Anthracycline 4'-Iodo-4'-Deoxydoxorubicin With Amyloid Fibrils: Inhibition of Amyloidogenesis", Proc. Natl. Acad. Sci. USA, 92: 2959-2963, 1995.

Soto et al. Beta-Sheet Breaker Peptides Inhibit Fibrillogenesis in A Rat Brain Model of Amyloidosis: Implications for Alzheimer's Therapy, Nature Medicine, 4(7): 822-826, 1998.

Tenidis et al. "Identification of A Penta- and Hexapeptide of Islet Amyloid Polypeptide (IAPP) With Amyloidogenic and Cytotoxic Propereties", Journal of Molecular Biology, 295(4): 1055-1071, 2000.

Kuner et al. "Controlling Polmerization of Beta-Amyloid and Prion-Derived Peptides With Synthetic Smal Molecule Ligands", Journal of Biological Chemistry, 275(3): 1673-1678, 2000.

Findeis "Approaches to Discovery and Characterization of Inhibitors of Amyloid Beta-Peptide Polymerization", Biochimia & Biophysica Acta, 1502: 76-84, 2000.

Wilesmith et al. "Bovine Spongiform Encephalopathy", Current Topics in Microbiology & Immunology, 172: 21-38, 1991.

Gajdusek "Unconventional Viruses and the Origin and Disappearance of Kuru", Science, 197(4307): 943-960, 1977.

Medora et al. "Fatal Familial Insomnia, A Prion Disease With A Mutation at Codon 178 of the Prion Protein Gene", The New England Journal of Medicine, 326(7): 444-449, 1992.

Pinkert et al. "An Albumin Enhancer Located lo Kb Upstream Functions Along With Its Promoter to Direct Efficient, Liver-Specific Expression in Transgenic Mice", Genes & Development, 1: 268-276, 1987.

Calame et al. "Transcriptional Controlling Elements in the Immunoglobulin and T Cell Receptor Loci", Advances in Immunology, 43: 235-275, 1988.

Winoto et al. "A Novel, Inducible and T Cell-Specific Enhancer Located at the 3' End of the T Cell Receptor Alpha Locus", The EMBO Journal, 8(3): 729-733, 1989.

Banerji et al. "A Lymphocyte-Specific Cellular Enhancer Is Located Downstream of the Joining Region in Immunoglobulin Heavy Chain Genes", Cell, 33: 729-740, 1983.

Byrne et al. "Mutiplex Gene Regulation: A Two-Tiered Approach to Transgene Regulation in Transgenic Mice", Proc. Natl. Acad. Sci. USA, 86: 5473-5477, 1989.

Edlund et al. "Cell-Specific Expression of the Rat Insuline Gene: Evidence for Role of Two Distinct 5' Flanking Elements", Science, 230(4278): 912-916, 1985.

Bursavich et al. "Designing Non-Peptide Peptidomimetics in the 21st Century: Inhibitors Targeting Comformational Ensembles", Journal of Medical Chemistry, 45(3): 541-558, 2002.

Baltzer et al. "De Novo Design of Proteins—What Are the Rules?", Chem. Rev., 101(10): 3153-3163, 2001.

Orlandi et al. "Cloning Immunoglobulin Variable Domains for Expression by the Polymerase Chain Reaction", Proc. Natl. Acad. Sci. USA, 86: 3833-3837, 1989.

Winter et al. "Man-Made Antibodies", Nature, 349: 293-299, 1991.

Kohler et al. "Continuous Cultures of Fused Cells Secreting Antibody of Predefined Specifity", Nature, 256: 495-497. 1975.

Kozbor et al. "Specific Immunoglobulin Production and Enhanced Tumorigenicity Following Ascites Growth of Human Hybridomas", Journal of Immunological Methods, 81: 31-42, 1985.

Cote et al. "Generation of Human Monoclonal Antibodies Reactive With Cellular Antigens", Proc. Natl. Acad. Sci. USA, 80: 2026-2030, 1983.

Cole et al. "Human Monoclonal Antibodies", Molecular &. Cellular Biochemistry, 62(2): 109-120, 1984.

Han et al. "Technetium Complexes for the Quantitation of Brain Amyloid", J. Am. Chem. Soc., 118: 4506-4507, 1996.

Sambrook et al. "Molecular Cloning: A Laboratory Manual", 2nd Edition, Cold Spring Harbor Laboratory, 1989.

Ausubel et al. Current Protocols in Molecular Biology, 1 (Suppl.63), 2002.

Perbal "A Practical Guide to Molecular Cloning", Wiley-Interscience Publication, 1988.

Stites et al. Basic & Clinical Immunology, 8th Edition, 1994.

Gait "Oligonucleotide Synthesis—A Practical Approach", IRL Press, 1984.

Freshney "Animal Cell Culture—A Practical Approach", IRL Press, 1986.

Marshak et al. "Strategies for Protein Purification and Charcterization, A Laboratory Course Manual", Cold Spring Harbor Laboratory Press, 1996.

Cooper "Selective Amyloid Staining As A Function of Amyloid Composition and Structure. Histochemical Analysis of the Alkaline Congo Red. Standardized Toluidine Blue, and Iodine Methods", Laboratory Investigation, 31(3): 232-238, 1974.

Gorman et al. "Alzheimer β-Amyloid Peptides, Structures Of Amyloid Fibrils and Alternate Aggregation Products", Biopolymers, 60: 381-394, 2001. Claims: 1-16, 22-26, 70-80, 91-100.

Kapurniotu et al. Database, Accession No. AAW93015, 1991. Claims: 1-16, 22-26.

Hoeppener et al. "The Complete Islet Amyloid Polypeptide Precursor Is Encoded by Two Exons", Biochem. Biophys. Res. Commun., 189: 1569-1577, 1993. Database, Accession No. S04016, 1993. Claims: 1-16, 22-26.

Stephenson et al. "The 'Promiscuous Drug Concept' With Applications to Alzheimer's Disease", FEBS Letters, 579: 1338-1342, 2005.

Hayden et al. "'A' Is for Amylin and Amyloid in Type 2 Diabetes Mellitus", JOP. J. Pancreas (Online), 2(4): 124-139, 2001.

Grady et al. "Axe-Txe, A Broad-Spectrum Proteic Toxin-Antitoxin System Specified by A Multidrug-Resistant, Clinical Isolate of *Enterococcus faecium*", Molecular Biology, 47(5): 1419-1432, 2003. Abstract, p. 1424, col. 1-p. 1426, col. 2, Fig.5.

Cherny et al. "The YefM Antitoxin Defines A Family of Natively Unfolded Proteins", The Journal of Biological Chemistry, 279(9): 8252-8261, 2004.

Engelberg-Kulka et al. "Bacterial Programmed Cell Death Systems as Targets for Antibiotics", Trends in Microbiology, 12(2): 66-71, 2004.

Forloni et al. "Anti-Amyloidogenic Activity of Tetracyclines: Studies In Vitro", FEBS Letters, 487(3): 404-407, 2001. Abstract, Results, Figs.1, 3.

Lansbury Jr. "Following Nature's Anti-Amyloid Strategy", Nature Biotechnology, 19(2): 112-113, 2001.

Grateau "Le Curli du Coli: Une Variété Physiologique d'Amylose", Medecine Sciences, 18(6-7): 664, 2002.

Cherny et al. "The Formation of *Escherichia coli* Curli Amyloid Fibrils Is Mediated by Prion-Like Peptide Repeats", Journal of Molecular Biology, 352(2): 245-252, 2005.

Görbitz "Nanotube Formation by Hydrophobic Dipeptides", Chemistry, 7(23): 5153-5159, 2001.

Reches et al. "Amyloid Fibril Formation by Pentapeptide and Tetrapeptide Fragments of Human Calcitonin", Journal of Biological Chemistry, 277(38): 35475-35480, 2002.

Haldar et al. "First Crystallographic Signature of the Highly Ordered Supramolecular Helical Assemblage From A Tripeptide Containing A Non-Coded Amino Acid", Tetrahedron Letters, 43(14): 2653-2656, 2002.

Maji et al. "Fibril-Forming Model Synthetic Peptides Containing 3-Aminophenylacetic Acid", Tetrahedron, 58(43): 8695-8702, 2002.

Hartgerink et al. "Peptide Nanotubes and Beyond", Chemistry, A European Journal, 4(8): 1367-1372, 1998.

Ghadiri et al. "Self-Assembling Organic Nanotubes Based on A Cyclic Peptide Architecture", Nature, 366: 324-327, 1993.

Horne et al. "A Heterocyclic Peptide Nanotube", Journal of the American Chemical Society, 125(31): 9372-9376, 2003.

Reches et al. "Casting Metal Nanowires Within Discrete Self-Assembled Peptide Nanotubes", Science, 300(5619): 625-627, 2003.

Adekore et al. "Carbon Nanotubes", p. 1-11, 2001.

Brauer "GB-245 Nanotubes: Directions and Techno", BCC, p. 1-14, 2000.

Martin et al. "The Emerging Field of Nanotube Biotechnology", Nature Reviews, 2: 29-37, 2003.

Zhang et al. "Design of Nanostructured Biological Materials Through Self-Assembly of Peptides and Proteins", Current Opinion in Chemical Biology, 6: 865-871, 2002.

Daenen et al. "The Wondrous World of Carbon Nanotubes", p. 1-8, 2003.

Gazit "Global Analysis of Tandem Aromatic Optapeptide Repeats: The Significance of the Aroma-Glycine Motif", Bioinformatics Discovery Note, 18(6): 880-883, 2002.

Gazit "The 'Correctly Folded' State of Proteins: Is it a Metastable State ?", Angew. Chem. Int. Ed., 41(2): 257-259, 2002.

Gazit "A Possible Role for 'Phi'-Stacking in the Self-Assembly of Amyloid Fibrils", FASEB: 77-83, 2002.

Coughlan et al. "Factors Influencing the Processing and Function of the Amyloid Beta Precursor Protein—A Potential Therapeutic Target in Alzheimer's Disease?", Pharmacology and Therapeutics, 86: 111-144, 2000.

Damas et al. "Review: TTR Amyloidosis—Structural Features Leading to Protein Aggregation and Their Implications on Therapeutic Strategies", Journal of Structural Biology, 130: 290-299, 2000.

Gazit "Mechanistic Studies of the Process of Amyloid Fibrils Formation by the Use of Peptide Fragments and Analogues: Implications of the Design of Fibrillization Inhibitors", Current Medicinal Chemistry, 9: 1667-1675, 2002.

Mazor et al. "Identification and Characterization of A Novel Molecular-Recognition and Self-Assembly Domain Within the Islet Amyloid Polypeptide", Journal of Molecular Biology, 322: 1013-1024, 2002.

Examiner's Report Dated Feb. 17, 2009 From the Australian Government, IP Australia Re.: Application No. 2004203461.

Office Action Dated Feb. 1, 2009 From the Israeli Patent Office Re.: Application No. 163285 and Its Translation Into English.

Office Action Dated Jan. 8, 2009 From the Israeli Patent Office Re.: Application No. 172788 and Its Translation Into English.

Office Action Dated Jan. 13, 2009 From the Government of India, Patent Office Re.: Application No. 1400/CHENP/2006.

Official Action Dated Feb. 24, 2009 From the US Patent and Trademark Office Re.: U.S. Appl. No. 11/660,522.

Official Action Dated Nov. 26, 2008 From the US Patent and Trademark Office Re.: U.S. Appl. No. 11/662,136.

Alic "Multiple Myeloma", Medical Network Inc., HealthAtoZ.com, 11 P., 2002. URL: http://www.lifesteps.com/gm/Atoz/ency/multiple_myeloma.jsp.

Chyan et al. "Potent Neuroprotective Properties Against the Alzheimer β-Amyloid by An Endogenous Melatonin-Related Indole Structure, Indole-3-Propionic Acid", The Journal of Biological Chemistry, 274(31): 21937-21942, Jul. 30, 1999.

Reza et al "Self-Assembling Organic Nanotubes Based on A Cyclic Peptide Architecture", Nature, 366: 324-327, 1993.

Sigma "Alphabetical List of Compounds: Phe-Phe, Phe-Pro, Phe-Val", Biochemicals and Reagents for Life Science Research, p. 774, 2000-2001.

Communication Pursuant to Article 94(3) EPC Dated Mar. 12, 2008 From the European Patent Office Re.: Application No. 05774727.1.

Communication Pursuant to Article 96(2) Dated Jul. 17, 2006 From the European Patent Office Re.: Application No. 03777149.0.

Communication Pursuant to Rules 109 and 110 EPC Dated Aug. 18, 2005 From the European Patent Office Re.: Application No. 04700494.0.

Examination Report Jan. 13, 2009 From the Government of India, Patent Office Re.: Application No. 1400/CHENP/2006.

Examiner's Report Dated Feb. 17, 2009 From the Australian Government, IP Australia Re.: Application No. 2004203461.

International Preliminary Report of Patentability Dated Mar. 17, 2006 From the International Preliminary Examining Authority Re.: Application No. PCT/IL2004/000890.

International Preliminary Report on Patentability Jan. 22, 2009 From the International Bureau of WIPO Re.: Application No. PCT/IL2005/000954.

International Preliminary Report on Patentability Dated Mar. 1, 2007 From the International Bureau of WIPO Re.: Application No. PCT/IL2005/000902.

International Preliminary Report on Patentability Dated Apr. 13, 2006 From the International Bureau of WIPO Re.: Application No. PCT/IL2004/000898.

International Preliminary Report on Patentability Dated Feb. 15, 2007 From the International Bureau of WIPO Re.: Application No. PCT/IL2005/000589.

International Preliminary Report on Patentability Dated Jan. 22, 2009 From the International Bureau of WIPO Re.: Application No. PCT/IL2004/000577.

International Preliminary Report on Patentability Dated Apr. 24, 2008 From the International Bureau of WIPO Re.: Application No. PCT/IL2006/001174.

International Preliminary Report on Patentability Dated Jan. 25, 2007 From the International Bureau of WIPO Re.: Application No. PCT/IL2005/000754.

OA Feb. 1, 2009 W Sec 8.

OA of Jan. 8, 2009 W Sec 8.

Official Action Dated Feb. 23, 2006 From the US Patent and Trademark Office Re.: U.S. Appl. No. 10/235,852.

Office Action Dated Feb. 1, 2009 From the Israeli Patent Office Re.: Application No. 163285 and Its Translation Into English.

Office Action Dated Jan. 8, 2009 From the Israeli Patent Office Re.: Application No. 172788 and Its Translation Into English.

Office Action Dated Jan. 13, 2009 From the Government of India, Patent Office Re.: Application No. 1400/CHENP/2006.

Official Action Dated May 2, 2008 From the US Patent and Trademark Office Re.: U.S. Appl. No. 11/656,542.

Official Action Dated Apr. 3, 2009 From the US Patent and Trademark Office Re.: U.S. Appl. No. 11/662,136.

Official Action Dated Apr. 10, 2009 From the US Patent and Trademark Office Re.: U.S. Appl. No. 11/386,880.

Official Action Dated Dec. 16, 2008 From the US Patent and Trademark Office Re.: U.S. Appl. No. 10/562,852.

Official Action Dated Apr. 19, 2006 From the US Patent and Trademark Office Re.: U.S. Appl. No. 10/901,243.

Official Action Dated Sep. 19, 2007 From the US Patent and Trademark Office Re.: U.S. Appl. No. 11/148,262.

Official Action Dated Feb. 24, 2009 From the US Patent and Trademark Office Re.: U.S. Appl. No. 11/660,522.

Official Action Dated Nov. 26, 2008 From the US Patent and Trademark Office Re.: U.S. Appl. No. 11/662,136.

Official Action Dated Sep. 27, 2007 From the US Patent and Trademark Office Re.: U.S. Appl. No. 11/148,266.

Partial European Search Report and the European Search Opinion Dated Apr. 16, 2009 From the European Patent Office Re.: Application No. 09002048.8.

Response Dated May 25, 2007 to Communication Pursuant to Article 94(3) of Jan. 18, 2007 From the European Patent Office Re.: Application No. 04700494.0.

Supplementary European Search Report Dated Apr. 18, 2006 From the European Patent Office Re.: Application No. 03704977.2.

Written Opinion Dated Jun. 15, 2006 From the International Preliminary Examining Authority Re.: Application No. PCT/IL03/00079.

Alic "Multiple Myeloma", Medical Network Inc., HealthAtoZ.com, 11 P., 2002. URL: http://www.lifesteps.com/gm/Atoz/ency/multiple_myeloma.jsp.

Asgharnejad "Ester Derivatives as Prodrugs", Transport Processes in Pharmaceutical Systems, 102: 186, 2000.

Chyan et al. "Potent Neuroprotective Properties Against the Alzheimer β-Amyloid by An Endogenous Melatonin-Related Indole Structure, Indole-3-Propionic Acid", The Journal of Biological Chemistry, 274(31): 21937-21942, Jul. 30, 1999.

Patani et al. "Bioisosterism: A Rational Approach in Drug Design", Chemical Reviews, 96(8): 3147-3176, 1996.

Reza et al "Self-Assembling Organic Nanotubes Based on A Cyclic Peptide Architecture", Nature, 366: 324-327, 1993.

Sigma "Alphabetical List of Compounds: Phe-Phe, Phe-Pro, Phe-Val", Biochemicals and Reagents for Life Science Research, p. 774, 2000-2001.

* cited by examiner

Fig. 2a

SEQUENCE LISTING

```
<160> NUMBER OF SEQ ID NOS: 132

<210> SEQ ID NO 1
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 1
atgaactgta caaaagagg                                              19

<210> SEQ ID NO 2
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 2
gacaagctta gtttcactca atg                                         23

<210> SEQ ID NO 3
<211> LENGTH: 19
<212> TYPE: DNA
<213> ORGANISM: Artificial sequence
<220> FEATURE:
```

```
<223> OTHER INFORMATION: Single strand DNA oligonucleotide

<400> SEQUENCE: 3
gtgaaactaa tctggtctg                                              19

<210> SEQ ID NO 4
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 4
tgaagctttt caataatgat aacgac                                      26

<210> SEQ ID NO 5
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 5
gtacaatgaa ctgtacaaaa gaag                                        24

<210> SEQ ID NO 6
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 6
cctttgaagc ttttcaataa tgataa                                      26

<210> SEQ ID NO 7
<211> LENGTH: 13
<212> TYPE: PRT
<213> ORGANISM: Artificial sequence
<220> FEATURE:
<223> OTHER INFORMATION: Synthetic peptide

<400> SEQUENCE: 7

Arg Thr Ile Ser Tyr Ser Glu Ala Arg Gln Asn Leu Ser
1               5                   10

<210> SEQ ID NO 8
<211> LENGTH: 13
<212> TYPE: PRT
<213> ORGANISM: Artificial sequence
<220> FEATURE:
<223> OTHER INFORMATION: Synthetic peptide

<400> SEQUENCE: 8

Arg Thr Ile Ser Tyr Ser Glu Ala Ala Gln Asn Leu Ser
1               5                   10

<210> SEQ ID NO 9
<211> LENGTH: 13
<212> TYPE: PRT
<213> ORGANISM: Artificial sequence
<220> FEATURE:
<223> OTHER INFORMATION: Synthetic peptide

<400> SEQUENCE: 9

Arg Thr Ile Ser Tyr Ser Glu Ala Gly Gln Asn Leu Ser
```

<210> SEQ ID NO 10
<211> LENGTH: 252
<212> TYPE: DNA
<213> ORGANISM: Actinobacillus actinomycetemcomitans

<400> SEQUENCE: 10

```
atgaatgtaa taagttattc tgcgtttcgt gcagaattgg caaccacact tgatcaggtg      60
gtagcagatc atagcccagt catgattacc agacaaaatg gcaaacacgc tgttgtaatg     120
agtttagaag atttcgcagc ttacgaagaa acggcttatt tattacgcag ccccaaaaat     180
agagagcgtt tattagcctc tattgaccag ctcaattcag gtaaaatcat cgaacgggaa     240
ctccaggaat ga                                                         252
```

<210> SEQ ID NO 11
<211> LENGTH: 255
<212> TYPE: DNA
<213> ORGANISM: Actinobacillus actinomycetemcomitans

<400> SEQUENCE: 11

```
atgattttag cttggacgga aaccgcctgg gaagattatc tttattggca gcaagttgat      60
aaaaagacgt tgttgcgcat taataaactt atccaaaata ttaccagatc acctttcgaa     120
ggcttaggca atcctaaacc tttaaaacat cagttatccg ggttttggtc tagaagaata     180
gataaagagc atcgtcttgt ataccaagta tcggatagcc atttaacgat tattcaatgc     240
cgctatcact actaa                                                      255
```

<210> SEQ ID NO 12
<211> LENGTH: 255
<212> TYPE: DNA
<213> ORGANISM: Agrobacterium tumefaciens

<400> SEQUENCE: 12

```
atggcgaatg tgcgatttac cgagttcagg cagaacttcg cgacccattt cgaccgggtt      60
ctggaaaccc gcgcgccatt gctcgtcacg cggcaaggca agaggcggt cgtggtgctt      120
gccgaaggag aatatgagag catgcaggaa acgctgcatc tcctgtccaa cccggcaaat     180
gcctcaaggc ttcgcgcgtc catgggcgaa cttgagcgcg gtgacaccat cgagcgggat     240
ccgaccgaag aatga                                                      255
```

<210> SEQ ID NO 13
<211> LENGTH: 270
<212> TYPE: DNA
<213> ORGANISM: Agrobacterium tumefaciens

<400> SEQUENCE: 13

```
atgaagctcg tctggacgct gagttcatgg gacgactatg agttctggca agaaccgat      60
gctcgcatgg tcgagaaaat aaacgatctt atccgaaatg ccaaacgcac gcccttgca    120
gggcttggga aaccggagcc tctgaagggc gatatggcag atattggtc tcggcggatt    180
accgccgagc atcggtttgt ctaccgtgta tccgggtccg gaagcgagca acggctggaa    240
gtcattcagt gccgcttcca ttaccaataa                                      270
```

<210> SEQ ID NO 14
<211> LENGTH: 246
<212> TYPE: DNA
<213> ORGANISM: Burkholderia cepacia

<400> SEQUENCE: 14

```
atgaacgtcc ttacttatag cgaggcgcgt gccggcttca agcaggcgat ggacgacgtc    60
tgccgcgatc acatacccat gctgatcacg aggcagacgg gcgaaaacgt ggtgatggtt   120
tcgctcgcgg atttcaatgc gatgcaggag accttgtatc tgttgagttc gtcgaagaac   180
gcccagcggc tcgcccgatc tatcgctcaa ctgaacgccg cggtgcgac tgcgcgtgaa   240
ctgctg                                                              246
```

<210> SEQ ID NO 15
<211> LENGTH: 252
<212> TYPE: DNA
<213> ORGANISM: Burkholderia cepacia

<400> SEQUENCE: 15

```
atgttcaccg acgacgcgtg ggacgattac ctgtattggc aagagaccga ccggaaggtc    60
gtgcgcaaga tcaacacgct gctggaggag tgccggcgcg atccttatcg cggtacgggg   120
aaaccggagg cgttgatggg cagcatgagc ggattgtggt ctcggcgtat cacgctggcc   180
gaccgtcttg tctacttgcc gcgagacgga agatctacg tgatcgcctt tcgcttccac   240
tacgactgct ga                                                       252
```

<210> SEQ ID NO 16
<211> LENGTH: 255
<212> TYPE: DNA
<213> ORGANISM: Coxiella burnetii

<400> SEQUENCE: 16

```
atgaacgtag ttacttttag cgaactcagg gcgcaactta aaaaaatctt ggatctttcc    60
gccgatcaac acgaacctgt cgtcgttaaa cggccaaata agaaaccat ggtcatttta   120
tctttacgcg actttgaggc tctaaaagaa acagcttatc tcttaagtaa cgaagctaat   180
gcggcccgtc ttcgtcagtc tatccgcagc ttaaaacaag gcaaggcaca aaaaaagaaa   240
ttaatggaag attaa                                                    255
```

<210> SEQ ID NO 17
<211> LENGTH: 276
<212> TYPE: DNA
<213> ORGANISM: Coxiella burnetii

<400> SEQUENCE: 17

```
atgcaaattt ccttcacgcc cgaagcctgg gaagattatt tatattggca aaaattcgac    60
aaaaaaatgc ttcgacgcat taatgaactc attaaggatg ctatgcacga gccttttcc   120
ggaaagggaa agccagaacc tttaaaattt gaattacaag gatattggtc aagacgatta   180
gatcaagaac atcgattggt ctacaaagtt ttagacgatt cgttaatgat tatcgccgca   240
agatttcact ataatcgcct taattctaaa aactga                             276
```

<210> SEQ ID NO 18
<211> LENGTH: 279
<212> TYPE: DNA
<213> ORGANISM: Escherichia coli

<400> SEQUENCE: 18

```
atgaactgta caaaagagga gattgacatg cgtacaatta gctacagcga agcgcgtcag    60
aatttgtcgg caacaatgat gaaagccgtt gaagatcatg ccccgatcct tattactcgt   120
```

```
cagaatggag aggcttgtgt tctgatgtca ctcgaagaat acaactcgct ggaagagacg    180
gcttatctac tgcgctcccc cgctaacgcc cggagattga tggactcaat cgatagcctg    240
aaatcaggca aggaacgga aaaggacatc attgagtga                             279

<210> SEQ ID NO 19
<211> LENGTH: 255
<212> TYPE: DNA
<213> ORGANISM: Escherichia coli

<400> SEQUENCE: 19
gtgaaactaa tctggtctga ggaatcatgg gacgattatc tgtactggca ggaaacagat     60
aagcgaattg ttaaaaagat caatgaactt atcaaagata cccgcagaac gccatttgaa    120
ggtaagggga agccagaacc cctgaaacat aatttgtcag gcttctggtc ccgacgcatt    180
acagaggagc accgtctggt atacgcggtt accgacgatt cactgctcat tgcagcgtgt    240
cgttatcatt attga                                                     255

<210> SEQ ID NO 20
<211> LENGTH: 270
<212> TYPE: DNA
<213> ORGANISM: Enterococcus faecium

<400> SEQUENCE: 20
atggaagcag tagcttattc aaatttccgc caaaatttac gtagttatat gaaacaagtt     60
aatgaggatg ctgaaacact tattgtaaca agtaaagatg tagaagatac agttgttgta    120
ttatcaaaaa gagattatga ttctatgcaa gaaacgttga gaacactttc taataattac    180
gtcatggaaa aaattcgtcg aggagatgaa caattctcca aggtgcatt taaaacacat    240 gacttaatcg aggttgaatc tgatgattaa                                     270

<210> SEQ ID NO 21
<211> LENGTH: 258
<212> TYPE: DNA
<213> ORGANISM: Enterococcus faecium

<400> SEQUENCE: 21
atgattaagg cttggtctga tgatgcttgg gatgattatc tttattggca tgagcaagga     60
aacaaaagca atataaaaaa gattaacaag ttaataaaag atatcgatcg ttccccttt    120 gctggattag aaaacctga gccattaaag catgatttat ctggaaaatg gtccagaaga    180
attacagatg aacatagact gatatataga gttgaaaatg aaacgatatt tatttattct    240
gcaaaagatc actattaa                                                  258

<210> SEQ ID NO 22
<211> LENGTH: 258
<212> TYPE: DNA
<213> ORGANISM: Francisella tularensis

<400> SEQUENCE: 22
atgcaaaccg ttaattattc aactttaga atgaactat

<210> SEQ ID NO 23
<211> LENGTH: 207
<212> TYPE: DNA
<213> ORGANISM: Francisella tularensis

<400> SEQUENCE: 23

```
atgatacttt cttggtcaac taatgcttgg gaagattatc tatattggca aagcatagat      60
aagaaaaagc taaaacggat taatttgcta atcaaagaca ttatgagaaa tcactttgag     120
ggattaggag agcctgaacc tttgaagcat aatttctctg gttattggtc tagacgaata     180
gacaaagaac atctgaataa tctataa                                         207
```

<210> SEQ ID NO 24
<211> LENGTH: 222
<212> TYPE: DNA
<213> ORGANISM: Klebsiella pneumoniae

<400> SEQUENCE: 24

```
atgagaacgg ttaactatag cgaagcccgg caaaatctgg ccgatgtgct ggaaagcgca      60
gtgacaggtg tacctgtgac cattacccgt cgtgggcata atctgcagt catcattagt     120 gcagaagagt ttgaacgcta ccaggcggcc agaatggatg atgagttcgc ggctatcatg     180
gcggttcatg gtgatgagat cagggagctt gcggataaat ga                        222
```

<210> SEQ ID NO 25
<211> LENGTH: 369
<212> TYPE: DNA
<213> ORGANISM: Klebsiella pneumoniae

<400> SEQUENCE: 25

```
atgacgctgc agattatctc agcggaagag ataatacagt ttcacgacag gctgctccgc      60
gtcacgcctg gcgttgccgg tatgcccgat ccggggcgtg ccgaagcgat aatgtatagg     120
gtgctaaaca aaattgaata tgaaggtgtg acagacgtgt ggcgactcgc tgcgatgcat     180
ctgctggcga tttctcgcgg tcatatattt aatgatggta ataagcgtac ggcactgttt     240
atcaccctgc ttttttaaa gcgaaatgga attatattgc cagcgaatcc agacttcgtc     300
ggcatgaccg tcgaggcagc agcagggcaa cttaccctgg aacagattgt cgcgcgtttg     360
cgtggatga                                                             369
```

<210> SEQ ID NO 26
<211> LENGTH: 276
<212> TYPE: DNA
<213> ORGANISM: Mycobacterium bovis

<400> SEQUENCE: 26

```
atgagcatca gtgcgagcga ggcgaggcag cgcctgtttc cactcatcga acaggtcaat      60
accgatcacc agccggtgcg gatcacctcc cgggccggcg atgcggtgct gatgtccgcc     120
gacgactacg acgcgtggca ggaaacggtc tatctgctgc gctcaccgga gaacgccagg     180
cggttgatgg aagcggttgc ccgggataag gctgggcact cggctttcac caagtctgta     240
gatgagctgc gggagatggc cggcggcgag gagtga                               276
```

<210> SEQ ID NO 27
<211> LENGTH: 258
<212> TYPE: DNA
<213> ORGANISM: Mycobacterium bovis

<400> SEQUENCE: 27

```
gtgagaagcg tcaacttcga tcccgatgcc tgggaggact tcttgttctg gctggccgct    60
gatcgcaaaa cggcccgtcg gatcacccgg ttgatcggag aaattcagcg tgatccgttc   120
agcgggatcg gcaaacccga gccgctccaa ggtgagttgt cgggatactg gtcgcgccgg   180
atcgacgacg aacaccggct agtgtatcga gcgggcgacg acgaagtcac gatgctgaag   240
gcccgatacc actactga                                                 258

<210> SEQ ID NO 28
<211> LENGTH: 276
<212> TYPE: DNA
<213> ORGANISM: Mycobacterium tuberculosis

<400> SEQUENCE: 28
atgagcatca gtgcgagcga ggcgaggcag cgcctgtttc cactcatcga acaggtcaat    60
accgatcacc agccggtgcg gatcacctcc cgggccggcg atgcggtgct gatgtccgcc   120
gacgactacg acgcgtggca ggaaacggtc tatctgctgc gctcaccgga gaacgccagg   180
cggttgatgg aagcggttgc ccgggataag gctgggcact cggctttcac caagtctgta   240
gatgagctgc gggagatggc cggcggcgag gagtga                             276

<210> SEQ ID NO 29
<211> LENGTH: 258
<212> TYPE: DNA
<213> ORGANISM: Mycobacterium tuberculosis

<400> SEQUENCE: 29
gtgagaagcg tcaacttcga tcccgatgcc tgggaggact tcttgttctg gctggccgct    60
gatcgcaaaa cggcccgtcg gatcacccgg ttgatcggag aaattcagcg tgatccgttc   120
agcgggatcg gcaaacccga gccgctccaa ggtgagttgt cgggatactg gtcgcgccgg   180
atcgacgacg aacaccggct ggtgtatcga gcgggcgacg acgaagtcac gatgctgaag   240
gcccgatacc actactga                                                 258

<210> SEQ ID NO 30
<211> LENGTH: 297
<212> TYPE: DNA
<213> ORGANISM: Neisseria europea A

<400> SEQUENCE: 30
ttggcagaat gtaatgtaca aataaatgta caattggaga acctatggga cgctatcact    60
tacagcactg ccagagccaa acttgccgac accatgaacc cgtttgcga taaccatgaa   120 cctatcataa tcacacgcaa cggagaacaa tccgttgtaa tgatgtcgct cgacgacttc   180
aaggcgctgg aggaaacctc ttacctgctc cgtagcccaa agaatgcgaa gcggctgctg   240
gaaagcatcg cagctcttga atcaggcaga ggcgaaacga gaagcctggc agagtga      297

<210> SEQ ID NO 31
<211> LENGTH: 255
<212> TYPE: DNA
<213> ORGANISM: Neisseria europea A

<400> SEQUENCE: 31
gtgaagctgg ttttctctga gcaggcctgg gaagactatt tgtactggca aaagacagac    60
cgaaaaaccg tacagcgaat cgatacgctg gtgaaagaga ttacaagaac accacacgag   120
ggtaccggca aacccgagcc actgaaacat gcgctgtcag gttattggtc acgccgtatc   180
aataacgagc accggatcgt ctataaaatt gcggatgact cgttgtttat tgctcaactg   240
```
agataccact actga                                              255

<210> SEQ ID NO 32
<211> LENGTH: 309
<212> TYPE: DNA
<213> ORGANISM: Neisseria europea B

<400> SEQUENCE: 32
gtgtatcttt tttatacttg tacaatttat tgtgcaaatg aggttgccat gaaggttgtt    60
acttattcgc atgcgcgtaa tgcgttaaag tctattttgg atgatgtcat tcaggatgct   120
gatgtaattg ttattagtcg tcgcgatgca gaaggtgatg ctgtggtgat gtcgctggat   180
agctataaca gcatcatgga aacattgcac ttaaccagta atccagcaaa tgccgcagcc   240
ttagccaagg caattgctca ggataaggca ggacaagcac aagaccaccc attgctttct   300
gccgattaa                                                           309

<210> SEQ ID NO 33
<211> LENGTH: 261
<212> TYPE: DNA
<213> ORGANISM: Neisseria europea B

<400> SEQUENCE: 33
gtgcgtgcca ttcgttttgt tcctgatgcg tgggaggctt acctttactg gcaagaccag    60
gataaaaaaa cgctcaggcg attgaattct ctgattactg ccgcttctcg tgatccattt   120
gttggtattg gcaaaccaga accactgcgg ggtgaattgt cgggttattg gtcaagacgt   180
atcgatgaaa ctaatcgttt ggtttatcgt gttactgatg ttgagttagt gattattgct   240
tgccgatttc actatgaata a                                             261

<210> SEQ ID NO 34
<211> LENGTH: 243
<212> TYPE: DNA
<213> ORGANISM: Neisseria europea C

<400> SEQUENCE: 34
atggcaatac taaacgcaac agaagcaaga gcgaggttgt acgccttaat tgatgaggcc    60
gcagaaacac accagcctat tgtgattaag ggaaaaaggt caagtgcggt gcttttatcg   120
gaggaagact ggaacgctat caacgagacg ctttacttgg tttctatccc gggaatgcgc   180
gaatccatta tggagggtat gaaaactgat gtggatgagt gcagtaggga attggattgg   240
taa                                                                 243

<210> SEQ ID NO 35
<211> LENGTH: 261
<212> TYPE: DNA
<213> ORGANISM: Neisseria europea C

<400> SEQUENCE: 35
atgtgggagc tgcgatatac ccatcaagcg caaaaggatg caaaaaagct ggcatcgtct    60
gggcttaaag ataaggcaga ggagttgtta gcggttgtga ggaataatcc gtaccaaacc   120 ccaccccct atgaaaagct ggttggtgat ttggctggag cctgttcacg ccgtatcaac   180
atccagcaca ggctcgtgta tcaggtgttg gagcgggaga ggatagtaaa ggttttgcgt   240
atgtggactc attatgtgta g                                             261

<210> SEQ ID NO 36

<211> LENGTH: 408
<212> TYPE: DNA
<213> ORGANISM: Nostoc sp. PCC 7120

<400> SEQUENCE: 36

```
atgtactgga ttaaatttga agtacacaa agggagcttt taatacttat gctttctaac      60
acttacactt acacacaagc acgagatcgt ttgtctgaat tatgcgacaa ggttacttca     120
gaacgtgatt ttgtagttat tacacgtcgg aatgctgaaa atgtcgcttt aatacctgtt    180
gacgagcttt cgagtctttt agaaactgct catcttttac gttccccacg taacgctgaa    240
cgtttgctaa gggctttaga tagagctaaa tcaggtgttg tggaatctca agtttggat     300
gatattcgta aggagttagg atttgaccaa aagaagagt cacaaaaacc aatcaaacga     360
agaagttcca gtaactccaa agcaaagaaa acagtgttt caacctga                  408
```

<210> SEQ ID NO 37
<211> LENGTH: 246
<212> TYPE: DNA
<213> ORGANISM: Nostoc sp. PCC 7120

<400> SEQUENCE: 37

```
gtgtttcaac ctgaattttt agaagactta gaattttggg tagaaactaa tcaacgagtt     60
gccttaaagg ctttggatct tgtcaaagag acttgccgag atccttttaa gggaaaaggc    120
aagcctgaac ctttaaaata tttagatcct gatacttggt ctcgtcgatt aacgcaagaa    180
catagaattg tataccttgt taaagacgat gaaataaatt ttttacaagc ccgctatcat    240
tattaa                                                                246
```

<210> SEQ ID NO 38
<211> LENGTH: 255
<212> TYPE: DNA
<213> ORGANISM: Pseudomonas fluorescence

<400> SEQUENCE: 38

```
atggacacta tcaactacac cacagctcgt gcgcacttgg ctgaaaccat ggatcgcgtg     60
aatgaagact gcgccccgct tctggtaacc cgacaaaaag gcgagcctgt agtgatgatg    120
tctctggccg aatacaacgc gctggaagaa acggcttatc tgctgcgttc tccggccaat    180
gccgagcgct tgatcaaatc aattggcgaa atgcgcgctg aaaagccaa agtcaggcaa    240
ctgattgaag aatga                                                     255
```

<210> SEQ ID NO 39
<211> LENGTH: 255
<212> TYPE: DNA
<213> ORGANISM: Pseudomonas fluorescence

<400> SEQUENCE: 39

```
atgaaaatcc agttcacgcc aacgggctgg gaagactact tatggtttca acaaaacgat     60
aaggccggtc tcaaacgaat caatcttttg atcaaagcga tccagcgcca acccttgaa    120
ggcttgggca aaccggagcc gctcaagcac aacatgagcg cttctggtc acggcggata    180
actgccgagc atcgcttggt ctatgcgatc gtagacggcg aaatctgcgt cataacttgc    240
agatttcact actga                                                     255
```

<210> SEQ ID NO 40
<211> LENGTH: 285
<212> TYPE: DNA
<213> ORGANISM: Pseudomonas putida

```
<400> SEQUENCE: 40
atgcacgtac tgacttttag ccaggctcgc gccgaactga agcagacaat ggatgatgtt    60
tgccgggacc atgagcccgc cgtaatcacg cgacagcgtg gcgaacccgt agtgatgatg   120
tctctggagg actacaacgg gatgaacgag accattcacc tgttgggatc gtccaaaaac   180
gcttcgcgct tgcgctcatc catcgctcag ctccgggacg gccaggcctt gacgaaggaa   240
ctggacctca atgagcaaga accagaagca gcggaacaag aatga                  285

<210> SEQ ID NO 41
<211> LENGTH: 255
<212> TYPE: DNA
<213> ORGANISM: Pseudomonas putida

<400> SEQUENCE: 41
gtgaagttca ccaaggaggg ctgggaggat tactgtcact ggcagaatgc cgacctcacc    60
atcctcggca acatcaaccg cctaattgac gtgtgcctac gcacccccta cacgggtatt   120
ggcaagcctg agccgctgaa aggcgattta tctggcttgt ggtcccgccg catcacccgt   180
gagcaccgcc tggtctactt cttcgaggcc ggtatgctca ccgttctgca atgccgctac   240
cactacgacg actaa                                                    255

<210> SEQ ID NO 42
<211> LENGTH: 279
<212> TYPE: DNA
<213> ORGANISM: Pseudomonas syringae

<400> SEQUENCE: 42
atgcaggttt tatcattcag ccaggctcgc gccggtttaa agcaagcgat ggatgatgtg    60
tgccgggacc atgagccagc actcatcaca cgcctgcgcg tgatcatgt agtcatgctt   120 tcccttgatg actacaactc gatgtcagaa accatgtacc tgctaggcac agaggccaat   180
gcgaagcacc tgcggcaatc cattgcgcag cacaaagccg aaaagccctt cgtaaaggaa   240
atttcactgg atgtcacagg gtcagaaaca gaagaataa                         279

<210> SEQ ID NO 43
<211> LENGTH: 249
<212> TYPE: DNA
<213> ORGANISM: Pseudomonas syringae

<400> SEQUENCE: 43
gtgcatttca ccctatcggg atgggatgat tacactcact ggaaggatgc cgatcaggca    60
atttccctgt caatagacag cctcattagc cagtgcctgc gtacgccgtt caaaggcacc   120
ggtaagccga gaccactgac cggcgattta accgggtact ggtcccgccg catcaccaaa   180
gagcatcgtc ttgtctactt ctatgagggc ggtgtactga cagtcatcgc gtgtcgccat   240
cattactag                                                           249

<210> SEQ ID NO 44
<211> LENGTH: 195
<212> TYPE: DNA
<213> ORGANISM: Rickettsia conorii

<400> SEQUENCE: 44
atgaactcaa ttagcggcac ttcatttaga aaaaacttaa gctctgtact aaataccgta    60
gaaaacgatc atgtcccctta tcttattaaa agaaagaatc ataagaatat tattctttta  120
```

```
accgaagaag aatatgaatc tacaaaagaa acattatatt tattatctaa tctggggcta    180
atgcgaatcg aataa                                                      195

<210> SEQ ID NO 45
<211> LENGTH: 234
<212> TYPE: DNA
<213> ORGANISM: Rickettsia conorii

<400> SEQUENCE: 45
acactagaat cagcggagga tttagcgtat tggaaaaaat acgatattaa aaatatgaa     60 cgtattaaac ttctaataaa aaatatccaa gaagcaccgg ttacaggtat aggtaagccc   120
gaacctttaa aacatatatt atcaggttta tggtcacgta gaattaacca cgaacataga   180
ctaatatatt ctgtcaatac taaacaaatt ataatatata attgtagctt tcat          234

<210> SEQ ID NO 46
<211> LENGTH: 228
<212> TYPE: DNA
<213> ORGANISM: Salmonella typhi

<400> SEQUENCE: 46
atgtttatgc gtacggttaa ctatagcgaa gcgcggcaaa atctggccga agtcctggaa    60
agtgcggtga cggggggggcc tgttaccatc acgcgtcgtg ggcataagtc cgcagtgatc   120
atcagcgccg aggagtttga gcgttatcag acggcgcgaa tggatgatga gtttgctgcc   180
attatggcgg ttcatggcaa tgagctcagg gagctggcgg ataaatga                228

<210> SEQ ID NO 47
<211> LENGTH: 369
<212> TYPE: DNA
<213> ORGANISM: Salmonella typhi

<400> SEQUENCE: 47
atgaccctac aacttatctc agcggaagag ataattcagt ttcacgacag gcttctccgc    60
gttacgcctg gtgtaacagg catgcctgat cctggccgcg cggaagcgct aatgtaccgg   120
gtactcaagc aaatcgaata tgaaggggtg accgacgtgt ggctgctggc ggcaatgcat   180
ttgctcgcta tatcccgtgg gcatatcttc aatgatggta acaaacgtac cgccttattt   240
attacgctgc tgttttttaaa gcgtaacggg atctcactcg ctgcgaatcc ggattttgtc   300
gatatgacag tcgatgcggc ggcagggcgg cttacgctgg agcaaattgc cgttcgctta   360
cgtgcctga                                                            369

<210> SEQ ID NO 48
<211> LENGTH: 252
<212> TYPE: DNA
<213> ORGANISM: Streptococcus aureus

<400> SEQUENCE: 48
atgattatta aaaattattc atacgctcga cagaatttaa aggcacttat gacaaaagta    60
aatgatgata gtgatatggt aactgtaaca tctactgatg ataaaaacgt agtaatcatg   120
tcagaatcag attataactc catgatggaa acactttacc tccaacagaa cccaaataat   180
gctgaacact agctcaatc aattgcagat ctagaacgtg ggaaaactat aacgaaagat   240
atagatgtat aa                                                        252

<210> SEQ ID NO 49
<211> LENGTH: 267
```

```
<212> TYPE: DNA
<213> ORGANISM: Streptococcus aureus

<400> SEQUENCE: 49
atggctaggt taaatattac gttttcgcct caagcctttg aagattataa gtattttcag        60
cagaacaata aaaaaatggt gaagaagatt aatgagttac ttaaaagtat tgacagaaat       120
ggtgcattgg aaggtatagg taagcctgaa aagttaaaat cgaatctgac tgggtattat       180
agtagacgta tcaatcacga acatagattg gtttatacag tagatgacaa tcatataaaa       240
atagcatcat gtaaatacca ttattaa                                           267

<210> SEQ ID NO 50
<211> LENGTH: 255
<212> TYPE: DNA
<213> ORGANISM: Streptococcus pneumoniae

<400> SEQUENCE: 50
atggaagcag tcctttactc aacattccga aatcatttaa aggactacat gaagaaggta        60
aatgatgaat ttgagccttt gacggtggtc aataaaaatc cagatgagga cattgtagtc       120
ctttcaaaga gtgagtggga tagtatccaa gaaaccctga gaattgctca aaataaggaa       180
ctttctgata aggttttgcg aggaatggct caagttcgtg ctggaagtac tcaggtccat       240
gttattgagg agtaa                                                        255

<210> SEQ ID NO 51
<211> LENGTH: 255
<212> TYPE: DNA
<213> ORGANISM: Streptococcus pneumoniae

<400> SEQUENCE: 51
atgctgctca agtttacaga agatgcctgg gcagattatt gctactggca aaatcaggat        60
aagaaaacgt taaaagaat caataaaacta atcaaggata ttcaacgtga tcccttaca       120 ggaataggta aaccagaacc actcaaatat gattaccaag gagcctggtc acggcgtatt       180
gatgcagaaa atcgcttgat ttatatgatg gatggagata gcgtggcttt cttgtccttt       240
aaagatcatt actaa                                                        255

<210> SEQ ID NO 52
<211> LENGTH: 264
<212> TYPE: DNA
<213> ORGANISM: Streptomyces coelicolor

<400> SEQUENCE: 52
atgtccatca ccgccagcga agcccgtcag aacctgttcc cgctgataga gcaggtcaac        60
gaggaccacg ccccggtgca catcacctcc cgcaagggga acgccgtgct catgtccgag       120
gaggacttca cggcgtggac ggagacggtg catctcctgc gctcgccgag gaacgcccgc       180
cgtctgctcg actccatcgc ggaggccgag gcgggcgacg cgactgagca cgacctgatc       240
gacccggacg cggagcgggc gtga                                              264

<210> SEQ ID NO 53
<211> LENGTH: 255
<212> TYPE: DNA
<213> ORGANISM: Streptomyces coelicolor

<400> SEQUENCE: 53
gtgaggatca ctttcacgtc ccacggctgg gaggactacg tccactgggc cgagagcgac        60
```

```
cggaaggtga ccaagcggat caacagactg atcgccgaca tcgcccgtga cccgttcaag        120
ggcgtcggca agccggagcc gctcaagggc gacctgtccg gctactggtc acggcgcatc        180
gacgacacgc accgtcttgt gtacaagccc accgatgacc agctggtcat cgtccaggcg        240
cgctaccact actga                                                         255

<210> SEQ ID NO 54
<211> LENGTH: 282
<212> TYPE: DNA
<213> ORGANISM: Streptomyces viridochromogenes

<400> SEQUENCE: 54
atgtcgataa accgcgagcg aagccgcaag gctctctttc cgctgatcaa gaaggtcaac         60
gacaatcacg aggccatcga gatcgtctcc aagcacggca acgccgtact cgtctcggcc        120
gaggattatg cagcgctgcg cgagggctcg tacctgctgc gctctccggc gaacgcccgt        180
cgactgctca aggcgtacga gaacgccctt gcccacgtca atgtgtcgga gcgggagctg        240
atcgatccgg attcggcgga cgctggttcg ggtgccgcgt ga                           282

<210> SEQ ID NO 55
<211> LENGTH: 255
<212> TYPE: DNA
<213> ORGANISM: Streptomyces viridochromogenes

<400> SEQUENCE: 55
gtgaggcttg tcttcgagga tcagggctgg gatgactaca cgtcctggct caagaacgac         60
cgcaagatgc tcgcccgcat caacaagctc atcgaggacg tcaggcgcga ccccttcacg        120
gggatcggca aaccccgagcc gctgaagtac cacttgccgg gggcgtggtc gcggcggatc        180
gacgacgaac accgcctcgt gtacctggtt acggacaagg agatcgtgat cctcgctgcc        240
cggtaccact actga                                                         255

<210> SEQ ID NO 56
<211> LENGTH: 303
<212> TYPE: DNA
<213> ORGANISM: Synechocystis sp. PCC 7942

<400> SEQUENCE: 56
ttggctaagt gctattgttg tacaacaagc tgtacaactc ctcggctcat gaaagttgtt         60
tccttcagtg acgccagaaa aaatctcaag actgtcttgg atgaagtcgt caacgacgct        120
gactacacga tcattactcg ccgcaatgcc gaggaagtcg tggtcatgtc cctcgactcc        180
ttcaatagcc tgatcgaaac cttccacctg ctcaaatccc ctgccaatgc tgctcaccta        240
caacgctcga tcgctcagta ccagcaaggt caaacagtcg agcgaaatct attagatgcg        300
taa                                                                      303

<210> SEQ ID NO 57
<211> LENGTH: 264
<212> TYPE: DNA
<213> ORGANISM: Synechocystis sp. PCC 7942

<400> SEQUENCE: 57
atgcgtaagc tggcttggac aaacgaggct tgggaagatt acctgtattg gcaagggcag         60
gacaagaaga cctcaaatcg catcaacaag ctcattaccg aaaccttgcg atcgcccttt        120 gagggggattg gtaagccaga agcgctcagg gagaacctga ctgggttttg gtcacgccgc        180
attgacgaca ccaatcgctt agtttacgca gtagcagatg actacctgac cattatttcc        240
```

```
tgtcgctacc actacagcga ttaa                                          264

<210> SEQ ID NO 58
<211> LENGTH: 264
<212> TYPE: DNA
<213> ORGANISM: Synechocystis sp. PCC 6803 A

<400> SEQUENCE: 58
atgaaagcaa ttacaaccac ccaagccaaa gatcatttgg atgaattaat taatgctgtc    60
atttctgatc tagaaccaac catcgttagc aacaatcaag gtcagcaggc ggtattaata   120
tcattggatg aatttaattc ttggcaagaa acccttaact tactctctaa tccaaccaac   180
gcagaacatt taatggcatc gattaagcaa gctgaaactg gacagatcat taagcaaaaa   240
ttaccagatt tattggaact gtga                                          264

<210> SEQ ID NO 59
<211> LENGTH: 261
<212> TYPE: DNA
<213> ORGANISM: Synechocystis sp. PCC 6803 A

<400> SEQUENCE: 59
gtgaaaatcg cctttaccga gctatcttgg catgattacc tctggtttca gcaaaatgat    60
aaaaaacttc tcaaaagaat taatttactc attaaggcaa ttgccaggga tccttttgat   120
ggtataggaa aaccagaacc actcaaagca aatctttccg gttactggtc gaggcgcatc   180
aattctgagc atcgtttggt gtacacgatt gctgatcgag atttactaat tatttcctgc   240
cgattccatt atcaaaggta a                                             261

<210> SEQ ID NO 60
<211> LENGTH: 264
<212> TYPE: DNA
<213> ORGANISM: Synechocystis sp. PCC 6803 B

<400> SEQUENCE: 60
atggaaacca ttaattatca acaattctct gaaaaactgc ccactttggt agaaaaaata    60
ggtaatgagc aagaacctct ctgtctagag cttccgaatt atttacgagc tgttattata   120
tctgagcaag attaccgtag tttgatggaa actgtttatc tgttgagtaa ccctgttaat   180
gctgaaaagt tattaactac cgctagtcga tcaattgatc aagctacatc gtggacaaaa   240
gtaaaaaatg acttaggact atga                                          264

<210> SEQ ID NO 61
<211> LENGTH: 261
<212> TYPE: DNA
<213> ORGANISM: Synechocystis sp. PCC 6803 B

<400> SEQUENCE: 61
atgaaggaag ttgttttaga ttcgcaggca attgaagata taaagtggtg gattcaacaa    60
gataaaaagt tagcgttaaa aatcatggaa ttaattgaga cgctaccaaa atcaccttt   120 gccggcaaag gaaaaccaga aaaacttcgt tttaatttgt caggttttg gccacggcgc   180 attactcaag agcatcgcct agtttacgaa gtcaccgatg atttcattcg tgttgtcagt   240
tgtcgttatc attaccgata g                                             261

<210> SEQ ID NO 62
<211> LENGTH: 243
<212> TYPE: DNA
```

<213> ORGANISM: Tiobacillus ferroxidant

<400> SEQUENCE: 62

```
atgtccaccc tcactgcaag cgaagcacgc gccaacctat atcggctcat tgaccaagcc      60
gctgagtcac atcagcccat ttatatcgcc ggaaagcgga caagtgcggt ccttctctcc     120
acggaagatt gggaagcaat ccaagaaaca ctatacctcc tttccgttcc gggcatgcgc     180
gaatctatca aggagggtat ggctgagccc cttagcaaga gcaatatgga cctcaagtgg     240
tga                                                                  243
```

<210> SEQ ID NO 63
<211> LENGTH: 252
<212> TYPE: DNA
<213> ORGANISM: Tiobacillus ferroxidant

<400> SEQUENCE: 63

```
gtggtctatt cgaaacacgc gcagaaggat gcgaagaagc tggcggctgc tggcttaaaa      60
aacaacgcaa tagaactcct ggccgttctt gccgccgatc catttcagaa cccgccaccc     120
tacgagaatc tcgtaggcga cctcgccggc gcgtattcac gacgcatcaa cattcagcat     180
cgtttggttt atgaagtctt tccaaaggag cgagtggttc gcgtgttgcg catgtggacg     240
cactatgagt ga                                                        252
```

<210> SEQ ID NO 64
<211> LENGTH: 252
<212> TYPE: DNA
<213> ORGANISM: Yersinia enterocolitica

<400> SEQUENCE: 64

```
atgagaacaa ttagttatag tgaagcgcgc cagaatttgt cgacaacgat ggtgcaaacg      60
gttgaggatc gagccccat cctcatcacc cgtcaaaatg ggacttcttg tgttcttatg     120
tcacttgaag aatatgaatc attggaagaa actgctatt tattgcgttc accagcaaac     180
gcgaagcact tgatggactc aattgaagag ttgagagcag gaaaaggaat tcaaagggaa     240
cttgaagcgt ga                                                        252
```

<210> SEQ ID NO 65
<211> LENGTH: 255
<212> TYPE: DNA
<213> ORGANISM: Yersinia enterocolitica

<400> SEQUENCE: 65

```
gtgaaaatta tattttccag ttgttcttgg gaggattatc tttattggca acaaacggat      60
aagaaaatcc tcaaacgcat taatgggtta gtaaaaaata ttcaaagaac gccatttgag     120
gtaaagggca aaccagaacc ccttaaacat aatctggcag ggttctggtc acggaggatg     180
acagaagagc acagacttgt ttatgaggtt ccggtgata atttattaat tgctgcttat     240
cgttactatt attga                                                     255
```

<210> SEQ ID NO 66
<211> LENGTH: 210
<212> TYPE: DNA
<213> ORGANISM: Yersinia enterocolitica

<400> SEQUENCE: 66

```
atgaatagca tcagttatac agccgcaaga aataatttag ccaaggtatt attggaagca      60
caaaagcagc ccgtagaaat cacgcgccgt gggcagagtg aggtctatat tatcagcaag     120
```

```
gctgattatg aggatttgat gaaagcaaag gtaaaggcac atattcaatt taaacatgca    180
gaaaccatta aagctcttgc tgatagatga                                     210
```

<210> SEQ ID NO 67
<211> LENGTH: 357
<212> TYPE: DNA
<213> ORGANISM: Yersinia enterocolitica

<400> SEQUENCE: 67

```
atgatatttt taacggcaaa tgatattgcg gagtttaacg cagaaattat ccctaacggc     60
aggcctgata atagtaagat tgaggctgta gccagccgcg tattaaatgc acatcattat    120
gacaacgtgg atgatgtata tcagttagcc gctatctact taattgccat tagtcgaggt    180 cacattttc ttgatgggaa caagcgcacg gcatttcaaa gcatggcgct gttccttggt     240
ataaatggcg tagacctgtg tgcaagcaat caactggaag aattaaccgt tgaagcagcg    300
caaggaaaaa ttggtgttga gcagataacg gaacagttac gcgagcttac cgagtaa       357
```

<210> SEQ ID NO 68
<211> LENGTH: 83
<212> TYPE: PRT
<213> ORGANISM: Actinobacillus actinomycetemcomitans

<400> SEQUENCE: 68

```
Met Asn Val Ile Ser Tyr Ser Ala Phe Arg Ala Glu Leu Ala Thr Thr
1               5                   10                  15

Leu Asp Gln Val Val Ala Asp His Ser Pro Val Met Ile Thr Arg Gln
            20                  25                  30

Asn Gly Lys His Ala Val Val Met Ser Leu Glu Asp Phe Ala Ala Tyr
        35                  40                  45

Glu Glu Thr Ala Tyr Leu Leu Arg Ser Pro Lys Asn Arg Glu Arg Leu
    50                  55                  60

Leu Ala Ser Ile Asp Gln Leu Asn Ser Gly Lys Ile Ile Glu Arg Glu
65                  70                  75                  80

Leu Gln Glu
```

<210> SEQ ID NO 69
<211> LENGTH: 84
<212> TYPE: PRT
<213> ORGANISM: Actinobacillus actinomycetemcomitans

<400> SEQUENCE: 69

```
Met Ile Leu Ala Trp Thr Glu Thr Ala Trp Glu Asp Tyr Leu Tyr Trp
1               5                   10                  15

Gln Gln Val Asp Lys Lys Thr Leu Leu Arg Ile Asn Lys Leu Ile Gln
            20                  25                  30

Asn Ile Thr Arg Ser Pro Phe Glu Gly Leu Gly Asn Pro Lys Pro Leu
        35                  40                  45

Lys His Gln Leu Ser Gly Phe Trp Ser Arg Arg Ile Asp Lys Glu His
    50                  55                  60

Arg Leu Val Tyr Gln Val Ser Asp Ser His Leu Thr Ile Ile Gln Cys
65                  70                  75                  80

Arg Tyr His Tyr
```

<210> SEQ ID NO 70
<211> LENGTH: 84
<212> TYPE: PRT
```

<213> ORGANISM: Agrobacterium tumefaciens

<400> SEQUENCE: 70

Met Ala Asn Val Arg Phe Thr Glu Phe Arg Gln Asn Phe Ala Thr His
1               5                   10                  15

Phe Asp Arg Val Leu Glu Thr Arg Ala Pro Leu Leu Val Thr Arg Gln
                20                  25                  30

Gly Lys Glu Ala Val Val Leu Ala Glu Gly Tyr Glu Ser Met
            35                  40                  45

Gln Glu Thr Leu His Leu Leu Ser Asn Pro Ala Asn Ala Ser Arg Leu
        50                  55                  60

Arg Ala Ser Met Gly Glu Leu Glu Arg Gly Asp Thr Ile Glu Arg Asp
65                  70                  75                  80

Pro Thr Glu Glu

<210> SEQ ID NO 71
<211> LENGTH: 89
<212> TYPE: PRT
<213> ORGANISM: Agrobacterium tumefaciens

<400> SEQUENCE: 71

Met Lys Leu Val Trp Thr Leu Ser Ser Trp Asp Asp Tyr Glu Phe Trp
1               5                   10                  15

Gln Arg Thr Asp Ala Arg Met Val Glu Lys Ile Asn Asp Leu Ile Arg
                20                  25                  30

Asn Ala Lys Arg Thr Pro Phe Ala Gly Leu Gly Lys Pro Glu Pro Leu
            35                  40                  45

Lys Gly Asp Met Ala Gly Tyr Trp Ser Arg Arg Ile Thr Ala Glu His
        50                  55                  60

Arg Phe Val Tyr Arg Val Ser Gly Ser Gly Ser Glu Gln Arg Leu Glu
65                  70                  75                  80

Val Ile Gln Cys Arg Phe His Tyr Gln
                85

<210> SEQ ID NO 72
<211> LENGTH: 82
<212> TYPE: PRT
<213> ORGANISM: Burkholderia cepacia

<400> SEQUENCE: 72

Met Asn Val Leu Thr Tyr Ser Glu Ala Arg Ala Gly Phe Lys Gln Ala
1               5                   10                  15

Met Asp Asp Val Cys Arg Asp His Ile Pro Met Leu Ile Thr Arg Gln
                20                  25                  30

Thr Gly Glu Asn Val Val Met Val Ser Leu Ala Asp Phe Asn Ala Met
            35                  40                  45

Gln Glu Thr Leu Tyr Leu Leu Ser Ser Ser Lys Asn Ala Gln Arg Leu
        50                  55                  60

Ala Arg Ser Ile Ala Gln Leu Asn Ala Gly Gly Ala Thr Ala Arg Glu
65                  70                  75                  80

Leu Leu

<210> SEQ ID NO 73
<211> LENGTH: 83
<212> TYPE: PRT
<213> ORGANISM: Burkholderia cepacia

<400> SEQUENCE: 73

Met Phe Thr Asp Asp Ala Trp Asp Asp Tyr Leu Tyr Trp Gln Glu Thr
1               5                   10                  15

Asp Arg Lys Val Val Arg Lys Ile Asn Thr Leu Leu Glu Glu Cys Arg
            20                  25                  30

Arg Asp Pro Tyr Arg Gly Thr Gly Lys Pro Glu Ala Leu Met Gly Ser
        35                  40                  45

Met Ser Gly Leu Trp Ser Arg Arg Ile Thr Leu Ala Asp Arg Leu Val
    50                  55                  60

Tyr Leu Pro Arg Asp Gly Lys Ile Tyr Val Ile Ala Phe Arg Phe His
65                  70                  75                  80

Tyr Asp Cys

<210> SEQ ID NO 74
<211> LENGTH: 84
<212> TYPE: PRT
<213> ORGANISM: Coxiella burnetii

<400> SEQUENCE: 74

Met Asn Val Val Thr Phe Ser Glu Leu Arg Ala Gln Leu Lys Lys Ile
1               5                   10                  15

Leu Asp Leu Ser Ala Asp Gln His Glu Pro Val Val Lys Arg Pro
            20                  25                  30

Asn Lys Glu Thr Met Val Ile Leu Ser Leu Arg Asp Phe Glu Ala Leu
        35                  40                  45

Lys Glu Thr Ala Tyr Leu Leu Ser Asn Glu Ala Asn Ala Ala Arg Leu
    50                  55                  60

Arg Gln Ser Ile Arg Ser Leu Lys Gln Gly Lys Ala Gln Lys Lys
65                  70                  75                  80

Leu Met Glu Asp

<210> SEQ ID NO 75
<211> LENGTH: 91
<212> TYPE: PRT
<213> ORGANISM: Coxiella burnetii

<400> SEQUENCE: 75

Met Gln Ile Ser Phe Thr Pro Glu Ala Trp Glu Asp Tyr Leu Tyr Trp
1               5                   10                  15

Gln Lys Phe Asp Lys Lys Met Leu Arg Arg Ile Asn Glu Leu Ile Lys
            20                  25                  30

Asp Ala Met His Glu Pro Phe Ser Gly Lys Gly Lys Pro Glu Pro Leu
        35                  40                  45

Lys Phe Glu Leu Gln Gly Tyr Trp Ser Arg Arg Leu Asp Gln Glu His
    50                  55                  60

Arg Leu Val Tyr Lys Val Leu Asp Asp Ser Leu Met Ile Ile Ala Ala
65                  70                  75                  80

Arg Phe His Tyr Asn Arg Leu Asn Ser Lys Asn
                85                  90

<210> SEQ ID NO 76
<211> LENGTH: 92
<212> TYPE: PRT
<213> ORGANISM: Escherichia coli

<400> SEQUENCE: 76

Met Asn Cys Thr Lys Glu Glu Ile Asp Met Arg Thr Ile Ser Tyr Ser
1               5                   10                  15

Glu Ala Arg Gln Asn Leu Ser Ala Thr Met Met Lys Ala Val Glu Asp
                20                  25                  30

His Ala Pro Ile Leu Ile Thr Arg Gln Asn Gly Glu Ala Cys Val Leu
            35                  40                  45

Met Ser Leu Glu Glu Tyr Asn Ser Leu Glu Glu Thr Ala Tyr Leu Leu
        50                  55                  60

Arg Ser Pro Ala Asn Ala Arg Arg Leu Met Asp Ser Ile Asp Ser Leu
65                  70                  75                  80

Lys Ser Gly Lys Gly Thr Glu Lys Asp Ile Ile Glu
                85                  90

<210> SEQ ID NO 77
<211> LENGTH: 84
<212> TYPE: PRT
<213> ORGANISM: Escherichia coli

<400> SEQUENCE: 77

Met Lys Leu Ile Trp Ser Glu Ser Trp Asp Asp Tyr Leu Tyr Trp
1               5                   10                  15

Gln Glu Thr Asp Lys Arg Ile Val Lys Ile Asn Glu Leu Ile Lys
                20                  25                  30

Asp Thr Arg Arg Thr Pro Phe Glu Gly Lys Gly Lys Pro Glu Pro Leu
            35                  40                  45

Lys His Asn Leu Ser Gly Phe Trp Ser Arg Ile Thr Glu Glu His
        50                  55                  60

Arg Leu Val Tyr Ala Val Thr Asp Asp Ser Leu Ile Ala Ala Cys
65                  70                  75                  80

Arg Tyr His Tyr

<210> SEQ ID NO 78
<211> LENGTH: 89
<212> TYPE: PRT
<213> ORGANISM: Enterococcus faecium

<400> SEQUENCE: 78

Met Glu Ala Val Ala Tyr Ser Asn Phe Arg Gln Asn Leu Arg Ser Tyr
1               5                   10                  15

Met Lys Gln Val Asn Glu Asp Ala Glu Thr Leu Ile Val Thr Ser Lys
                20                  25                  30

Asp Val Glu Asp Thr Val Val Val Leu Ser Lys Arg Asp Tyr Asp Ser
            35                  40                  45

Met Gln Glu Thr Leu Arg Thr Leu Ser Asn Asn Tyr Val Met Glu Lys
        50                  55                  60

Ile Arg Arg Gly Asp Glu Gln Phe Ser Lys Gly Ala Phe Lys Thr His
65                  70                  75                  80

Asp Leu Ile Glu Val Glu Ser Asp Asp
                85

<210> SEQ ID NO 79
<211> LENGTH: 85
<212> TYPE: PRT
<213> ORGANISM: Enterococcus faecium

<400> SEQUENCE: 79

Met Ile Lys Ala Trp Ser Asp Asp Ala Trp Asp Asp Tyr Leu Tyr Trp
1               5                   10                  15

His Glu Gln Gly Asn Lys Ser Asn Ile Lys Lys Ile Asn Lys Leu Ile

```
                20                  25                  30
Lys Asp Ile Asp Arg Ser Pro Phe Ala Gly Leu Gly Lys Pro Glu Pro
            35                  40                  45

Leu Lys His Asp Leu Ser Gly Lys Trp Ser Arg Arg Ile Thr Asp Glu
    50                  55                  60

His Arg Leu Ile Tyr Arg Val Glu Asn Glu Thr Ile Phe Ile Tyr Ser
65                  70                  75                  80

Ala Lys Asp His Tyr
                85

<210> SEQ ID NO 80
<211> LENGTH: 85
<212> TYPE: PRT
<213> ORGANISM: Francisella tularensis

<400> SEQUENCE: 80

Met Gln Thr Val Asn Tyr Ser Thr Phe Arg Asn Glu Leu Ser Asp Ser
1               5                   10                  15

Met Asp Arg Val Thr Lys Asn His Ser Pro Met Ile Val Thr Arg Gly
            20                  25                  30

Ser Lys Lys Glu Ala Val Val Met Ser Leu Glu Asp Phe Lys Ala
        35                  40                  45

Tyr Glu Glu Thr Ala Tyr Leu Met Arg Ser Met Asn Asn Tyr Lys Arg
    50                  55                  60

Leu Gln Asn Ser Ile Asp Glu Val Glu Ser Gly Leu Ala Ile Gln Lys
65                  70                  75                  80

Glu Leu Ile Glu Glu
                85

<210> SEQ ID NO 81
<211> LENGTH: 68
<212> TYPE: PRT
<213> ORGANISM: Francisella tularensis

<400> SEQUENCE: 81

Met Ile Leu Ser Trp Ser Thr Asn Ala Trp Glu Asp Tyr Leu Tyr Trp
1               5                   10                  15

Gln Ser Ile Asp Lys Lys Lys Leu Lys Arg Ile Asn Leu Leu Ile Lys
            20                  25                  30

Asp Ile Met Arg Asn His Phe Glu Gly Leu Gly Glu Pro Glu Pro Leu
        35                  40                  45

Lys His Asn Phe Ser Gly Tyr Trp Ser Arg Arg Ile Asp Lys Glu His
    50                  55                  60

Leu Asn Asn Leu
65

<210> SEQ ID NO 82
<211> LENGTH: 73
<212> TYPE: PRT
<213> ORGANISM: Klebsiella pneumoniae

<400> SEQUENCE: 82

Met Arg Thr Val Asn Tyr Ser Glu Ala Arg Gln Asn Leu Ala Asp Val
1               5                   10                  15

Leu Glu Ser Ala Val Thr Gly Val Pro Val Thr Ile Thr Arg Arg Gly
            20                  25                  30

His Lys Ser Ala Val Ile Ile Ser Ala Glu Glu Phe Glu Arg Tyr Gln
        35                  40                  45
```

```
Ala Ala Arg Met Asp Asp Glu Phe Ala Ala Ile Met Ala Val His Gly
        50                  55                  60

Asp Glu Ile Arg Glu Leu Ala Asp Lys
65                  70
```

<210> SEQ ID NO 83
<211> LENGTH: 122
<212> TYPE: PRT
<213> ORGANISM: Klebsiella pneumoniae

<400> SEQUENCE: 83

```
Met Thr Leu Gln Ile Ile Ser Ala Glu Glu Ile Ile Gln Phe His Asp
1               5                   10                  15

Arg Leu Leu Arg Val Thr Pro Gly Val Ala Gly Met Pro Asp Pro Gly
            20                  25                  30

Arg Ala Glu Ala Ile Met Tyr Arg Val Leu Asn Lys Ile Glu Tyr Glu
        35                  40                  45

Gly Val Thr Asp Val Trp Arg Leu Ala Ala Met His Leu Leu Ala Ile
    50                  55                  60

Ser Arg Gly His Ile Phe Asn Asp Gly Asn Lys Arg Thr Ala Leu Phe
65                  70                  75                  80

Ile Thr Leu Leu Phe Leu Lys Arg Asn Gly Ile Ile Leu Pro Ala Asn
                85                  90                  95

Pro Asp Phe Val Gly Met Thr Val Glu Ala Ala Ala Gly Gln Leu Thr
            100                 105                 110

Leu Glu Gln Ile Val Ala Arg Leu Arg Gly
        115                 120
```

<210> SEQ ID NO 84
<211> LENGTH: 91
<212> TYPE: PRT
<213> ORGANISM: Mycobacterium bovis

<400> SEQUENCE: 84

```
Met Ser Ile Ser Ala Ser Glu Ala Arg Gln Arg Leu Phe Pro Leu Ile
1               5                   10                  15

Glu Gln Val Asn Thr Asp His Gln Pro Val Arg Ile Thr Ser Arg Ala
            20                  25                  30

Gly Asp Ala Val Leu Met Ser Ala Asp Tyr Asp Ala Trp Gln Glu
        35                  40                  45

Thr Val Tyr Leu Leu Arg Ser Pro Glu Asn Ala Arg Arg Leu Met Glu
    50                  55                  60

Ala Val Ala Arg Asp Lys Ala Gly His Ser Ala Phe Thr Lys Ser Val
65                  70                  75                  80

Asp Glu Leu Arg Glu Met Ala Gly Gly Glu Glu
                85                  90
```

<210> SEQ ID NO 85
<211> LENGTH: 85
<212> TYPE: PRT
<213> ORGANISM: Mycobacterium bovis

<400> SEQUENCE: 85

```
Met Arg Ser Val Asn Phe Asp Pro Asp Ala Trp Glu Asp Phe Leu Phe
1               5                   10                  15

Trp Leu Ala Ala Asp Arg Lys Thr Ala Arg Arg Ile Thr Arg Leu Ile
            20                  25                  30
```

-continued

Gly Glu Ile Gln Arg Asp Pro Phe Ser Gly Ile Gly Lys Pro Glu Pro
         35                  40                  45

Leu Gln Gly Glu Leu Ser Gly Tyr Trp Ser Arg Arg Ile Asp Asp Glu
     50                  55                  60

His Arg Leu Val Tyr Arg Ala Gly Asp Asp Glu Val Thr Met Leu Lys
 65                  70                  75                  80

Ala Arg Tyr His Tyr
             85

<210> SEQ ID NO 86
<211> LENGTH: 91
<212> TYPE: PRT
<213> ORGANISM: Mycobacterium tuberculosis

<400> SEQUENCE: 86

Met Ser Ile Ser Ala Ser Glu Ala Arg Gln Arg Leu Phe Pro Leu Ile
 1               5                  10                  15

Glu Gln Val Asn Thr Asp His Gln Pro Val Arg Ile Thr Ser Arg Ala
             20                  25                  30

Gly Asp Ala Val Leu Met Ser Ala Asp Tyr Asp Ala Trp Gln Glu
         35                  40                  45

Thr Val Tyr Leu Leu Arg Ser Pro Glu Asn Ala Arg Arg Leu Met Glu
     50                  55                  60

Ala Val Ala Arg Asp Lys Ala Gly His Ser Ala Phe Thr Lys Ser Val
 65                  70                  75                  80

Asp Glu Leu Arg Glu Met Ala Gly Gly Glu Glu
             85                  90

<210> SEQ ID NO 87
<211> LENGTH: 85
<212> TYPE: PRT
<213> ORGANISM: Mycobacterium tuberculosis

<400> SEQUENCE: 87

Met Arg Ser Val Asn Phe Asp Pro Asp Ala Trp Glu Asp Phe Leu Phe
 1               5                  10                  15

Trp Leu Ala Ala Asp Arg Lys Thr Ala Arg Arg Ile Thr Arg Leu Ile
             20                  25                  30

Gly Glu Ile Gln Arg Asp Pro Phe Ser Gly Ile Gly Lys Pro Glu Pro
         35                  40                  45

Leu Gln Gly Glu Leu Ser Gly Tyr Trp Ser Arg Arg Ile Asp Asp Glu
     50                  55                  60

His Arg Leu Val Tyr Arg Ala Gly Asp Asp Glu Val Thr Met Leu Lys
 65                  70                  75                  80

Ala Arg Tyr His Tyr
             85

<210> SEQ ID NO 88
<211> LENGTH: 98
<212> TYPE: PRT
<213> ORGANISM: Neisseria europea A

<400> SEQUENCE: 88

Met Ala Glu Cys Asn Val Gln Ile Asn Val Gln Leu Glu Asn Leu Met
 1               5                  10                  15

Asp Ala Ile Thr Tyr Ser Thr Ala Arg Ala Lys Leu Ala Asp Thr Met
             20                  25                  30

Asn Arg Val Cys Asp Asn His Glu Pro Ile Ile Ile Thr Arg Asn Gly

```
                35                  40                  45
Glu Gln Ser Val Val Met Met Ser Leu Asp Asp Phe Lys Ala Leu Glu
        50                  55                  60

Glu Thr Ser Tyr Leu Leu Arg Ser Pro Lys Asn Ala Lys Arg Leu Leu
65                  70                  75                  80

Glu Ser Ile Ala Ala Leu Glu Ser Gly Arg Gly Glu Thr Arg Ser Leu
                85                  90                  95

Ala Glu

<210> SEQ ID NO 89
<211> LENGTH: 84
<212> TYPE: PRT
<213> ORGANISM: Neisseria europea A

<400> SEQUENCE: 89

Met Lys Leu Val Phe Ser Glu Gln Ala Trp Glu Asp Tyr Leu Tyr Trp
1               5                   10                  15

Gln Lys Thr Asp Arg Lys Thr Val Gln Arg Ile Asp Thr Leu Val Lys
            20                  25                  30

Glu Ile Thr Arg Thr Pro His Glu Gly Thr Gly Lys Pro Glu Pro Leu
        35                  40                  45

Lys His Ala Leu Ser Gly Tyr Trp Ser Arg Arg Ile Asn Asn Glu His
    50                  55                  60

Arg Ile Val Tyr Lys Ile Ala Asp Asp Ser Leu Phe Ile Ala Gln Leu
65                  70                  75                  80

Arg Tyr His Tyr

<210> SEQ ID NO 90
<211> LENGTH: 102
<212> TYPE: PRT
<213> ORGANISM: Neisseria europea B

<400> SEQUENCE: 90

Met Tyr Leu Phe Tyr Thr Cys Thr Ile Tyr Cys Ala Asn Glu Val Ala
1               5                   10                  15

Met Lys Val Val Thr Tyr Ser His Ala Arg Asn Ala Leu Lys Ser Ile
            20                  25                  30

Leu Asp Asp Val Ile Gln Asp Ala Asp Val Ile Val Ile Ser Arg Arg
        35                  40                  45

Asp Ala Glu Gly Asp Ala Val Val Met Ser Leu Asp Ser Tyr Asn Ser
    50                  55                  60

Ile Met Glu Thr Leu His Leu Thr Ser Asn Pro Ala Asn Ala Ala Ala
65                  70                  75                  80

Leu Ala Lys Ala Ile Ala Gln Asp Lys Ala Gly Gln Ala Gln Asp His
                85                  90                  95

Pro Leu Leu Ser Ala Asp
            100

<210> SEQ ID NO 91
<211> LENGTH: 86
<212> TYPE: PRT
<213> ORGANISM: Neisseria europea B

<400> SEQUENCE: 91

Met Arg Ala Ile Arg Phe Val Pro Asp Ala Trp Glu Ala Tyr Leu Tyr
1               5                   10                  15

Trp Gln Asp Gln Asp Lys Lys Thr Leu Arg Arg Leu Asn Ser Leu Ile
```

```
                    20                  25                  30
Thr Ala Ala Ser Arg Asp Pro Phe Val Gly Ile Gly Lys Pro Glu Pro
                35                  40                  45
Leu Arg Gly Glu Leu Ser Gly Tyr Trp Ser Arg Arg Ile Asp Glu Thr
 50                  55                  60
Asn Arg Leu Val Tyr Arg Val Thr Asp Val Glu Leu Val Ile Ile Ala
 65                  70                  75                  80
Cys Arg Phe His Tyr Glu
                85

<210> SEQ ID NO 92
<211> LENGTH: 80
<212> TYPE: PRT
<213> ORGANISM: Neisseria europea C

<400> SEQUENCE: 92

Met Ala Ile Leu Asn Ala Thr Glu Ala Arg Ala Arg Leu Tyr Ala Leu
 1               5                  10                  15
Ile Asp Glu Ala Ala Glu Thr His Gln Pro Ile Val Ile Lys Gly Lys
                20                  25                  30
Arg Ser Ser Ala Val Leu Leu Ser Glu Glu Asp Trp Asn Ala Ile Asn
                35                  40                  45
Glu Thr Leu Tyr Leu Val Ser Ile Pro Gly Met Arg Glu Ser Ile Met
 50                  55                  60
Glu Gly Met Lys Thr Asp Val Asp Glu Cys Ser Arg Glu Leu Asp Trp
 65                  70                  75                  80

<210> SEQ ID NO 93
<211> LENGTH: 86
<212> TYPE: PRT
<213> ORGANISM: Neisseria europea C

<400> SEQUENCE: 93

Met Trp Glu Leu Arg Tyr Thr His Gln Ala Gln Lys Asp Ala Lys Lys
 1               5                  10                  15
Leu Ala Ser Ser Gly Leu Lys Asp Lys Ala Glu Glu Leu Leu Ala Val
                20                  25                  30
Val Arg Asn Asn Pro Tyr Gln Thr Pro Pro Tyr Glu Lys Leu Val
                35                  40                  45
Gly Asp Leu Ala Gly Ala Cys Ser Arg Arg Ile Asn Ile Gln His Arg
 50                  55                  60
Leu Val Tyr Gln Val Leu Glu Arg Glu Ile Val Lys Val Leu Arg
 65                  70                  75                  80
Met Trp Thr His Tyr Val
                85

<210> SEQ ID NO 94
<211> LENGTH: 135
<212> TYPE: PRT
<213> ORGANISM: Nostoc sp. PCC 7120

<400> SEQUENCE: 94

Met Tyr Trp Ile Lys Phe Glu Ser Thr Gln Arg Glu Leu Leu Ile Leu
 1               5                  10                  15
Met Leu Ser Asn Thr Tyr Thr Tyr Thr Gln Ala Arg Asp Arg Leu Ser
                20                  25                  30
Glu Leu Cys Asp Lys Val Thr Ser Glu Arg Asp Phe Val Val Ile Thr
                35                  40                  45
```

```
Arg Arg Asn Ala Glu Asn Val Ala Leu Ile Pro Val Asp Glu Leu Ser
     50                  55                  60

Ser Leu Leu Glu Thr Ala His Leu Leu Arg Ser Pro Arg Asn Ala Glu
 65                  70                  75                  80

Arg Leu Leu Arg Ala Leu Asp Arg Ala Lys Ser Gly Val Val Glu Ser
                 85                  90                  95

Gln Ser Leu Asp Asp Ile Arg Lys Glu Leu Gly Phe Asp Gln Lys Glu
                100                 105                 110

Glu Ser Gln Lys Pro Ile Lys Arg Arg Ser Ser Ser Asn Ser Lys Ala
            115                 120                 125

Lys Lys Asn Ser Val Ser Thr
        130                 135

<210> SEQ ID NO 95
<211> LENGTH: 81
<212> TYPE: PRT
<213> ORGANISM: Nostoc sp. PCC 7120

<400> SEQUENCE: 95

Met Phe Gln Pro Glu Phe Leu Glu Asp Leu Glu Phe Trp Val Glu Thr
  1               5                  10                  15

Asn Gln Arg Val Ala Leu Lys Ala Leu Asp Leu Val Lys Glu Thr Cys
             20                  25                  30

Arg Asp Pro Phe Lys Gly Lys Gly Lys Pro Glu Pro Leu Lys Tyr Leu
         35                  40                  45

Asp Pro Asp Thr Trp Ser Arg Arg Leu Thr Gln Glu His Arg Ile Val
     50                  55                  60

Tyr Leu Val Lys Asp Asp Glu Ile Asn Phe Leu Gln Ala Arg Tyr His
 65                  70                  75                  80

Tyr

<210> SEQ ID NO 96
<211> LENGTH: 84
<212> TYPE: PRT
<213> ORGANISM: Pseudomonas fluorescence

<400> SEQUENCE: 96

Met Asp Thr Ile Asn Tyr Thr Thr Ala Arg Ala His Leu Ala Glu Thr
  1               5                  10                  15

Met Asp Arg Val Asn Glu Asp Cys Ala Pro Leu Leu Val Thr Arg Gln
             20                  25                  30

Lys Gly Glu Pro Val Val Met Met Ser Leu Ala Glu Tyr Asn Ala Leu
         35                  40                  45

Glu Glu Thr Ala Tyr Leu Leu Arg Ser Pro Ala Asn Ala Glu Arg Leu
     50                  55                  60

Ile Lys Ser Ile Gly Met Arg Ala Gly Lys Ala Lys Val Arg Gln
 65                  70                  75                  80

Leu Ile Glu Glu

<210> SEQ ID NO 97
<211> LENGTH: 84
<212> TYPE: PRT
<213> ORGANISM: Pseudomonas fluorescence

<400> SEQUENCE: 97

Met Lys Ile Gln Phe Thr Pro Thr Gly Trp Glu Asp Tyr Leu Trp Phe
  1               5                  10                  15
```

-continued

Gln Gln Asn Asp Lys Ala Gly Leu Lys Arg Ile Asn Leu Leu Ile Lys
        20                  25                  30

Ala Ile Gln Arg Gln Pro Phe Glu Gly Leu Gly Lys Pro Glu Pro Leu
            35                  40                  45

Lys His Asn Met Ser Gly Phe Trp Ser Arg Arg Ile Thr Ala Glu His
        50                  55                  60

Arg Leu Val Tyr Ala Ile Val Asp Gly Glu Ile Cys Val Ile Thr Cys
65                  70                  75                  80

Arg Phe His Tyr

<210> SEQ ID NO 98
<211> LENGTH: 94
<212> TYPE: PRT
<213> ORGANISM: Pseudomonas putida

<400> SEQUENCE: 98

Met His Val Leu Thr Phe Ser Gln Ala Arg Ala Glu Leu Lys Gln Thr
1               5                   10                  15

Met Asp Asp Val Cys Arg Asp His Glu Pro Ala Val Ile Thr Arg Gln
            20                  25                  30

Arg Gly Glu Pro Val Val Met Met Ser Leu Glu Asp Tyr Asn Gly Met
        35                  40                  45

Asn Glu Thr Ile His Leu Leu Gly Ser Ser Lys Asn Ala Ser Arg Leu
    50                  55                  60

Arg Ser Ser Ile Ala Gln Leu Arg Asp Gly Gln Ala Leu Thr Lys Glu
65                  70                  75                  80

Leu Asp Leu Asn Glu Gln Glu Pro Glu Ala Ala Glu Gln Glu
                85                  90

<210> SEQ ID NO 99
<211> LENGTH: 84
<212> TYPE: PRT
<213> ORGANISM: Pseudomonas putida

<400> SEQUENCE: 99

Met Lys Phe Thr Lys Glu Gly Trp Glu Asp Tyr Cys His Trp Gln Asn
1               5                   10                  15

Ala Asp Leu Thr Ile Leu Gly Asn Ile Asn Arg Leu Ile Asp Val Cys
            20                  25                  30

Leu Arg Thr Pro Phe Thr Gly Ile Gly Lys Pro Glu Pro Leu Lys Gly
            35                  40                  45

Asp Leu Ser Gly Leu Trp Ser Arg Arg Ile Thr Arg Glu His Arg Leu
    50                  55                  60

Val Tyr Phe Phe Glu Ala Gly Met Leu Thr Val Leu Gln Cys Arg Tyr
65                  70                  75                  80

His Tyr Asp Asp

<210> SEQ ID NO 100
<211> LENGTH: 92
<212> TYPE: PRT
<213> ORGANISM: Pseudomonas syringae

<400> SEQUENCE: 100

Met Gln Val Leu Ser Phe Ser Gln Ala Arg Ala Gly Leu Lys Gln Ala
1               5                   10                  15

Met Asp Asp Val Cys Arg Asp His Glu Pro Ala Leu Ile Thr Arg Leu
            20                  25                  30

```
Arg Gly Asp His Val Val Met Leu Ser Leu Asp Asp Tyr Asn Ser Met
            35                  40                  45

Ser Glu Thr Met Tyr Leu Leu Gly Thr Glu Ala Asn Ala Lys His Leu
 50                  55                  60

Arg Gln Ser Ile Ala Gln His Lys Ala Gly Lys Ala Phe Val Lys Glu
 65                  70                  75                  80

Ile Ser Leu Asp Val Thr Gly Ser Glu Thr Glu Glu
                85                  90
```

<210> SEQ ID NO 101
<211> LENGTH: 82
<212> TYPE: PRT
<213> ORGANISM: Pseudomonas syringae

<400> SEQUENCE: 101

```
Met His Phe Thr Leu Ser Gly Trp Asp Asp Tyr Thr His Trp Lys Asp
 1               5                  10                  15

Ala Asp Gln Ala Ile Ser Leu Ser Ile Asp Ser Leu Ile Ser Gln Cys
                20                  25                  30

Leu Arg Thr Pro Phe Lys Gly Thr Gly Lys Pro Arg Pro Leu Thr Gly
            35                  40                  45

Asp Leu Thr Gly Tyr Trp Ser Arg Arg Ile Thr Lys Glu His Arg Leu
 50                  55                  60

Val Tyr Phe Tyr Glu Gly Gly Val Leu Thr Val Ile Ala Cys Arg His
 65                  70                  75                  80

His Tyr
```

<210> SEQ ID NO 102
<211> LENGTH: 64
<212> TYPE: PRT
<213> ORGANISM: Rickettsia conorii

<400> SEQUENCE: 102

```
Met Asn Ser Ile Ser Gly Thr Ser Phe Arg Lys Asn Leu Ser Ser Val
 1               5                  10                  15

Leu Asn Thr Val Glu Asn Asp His Val Pro Tyr Leu Ile Lys Arg Lys
                20                  25                  30

Asn His Lys Asn Ile Ile Leu Leu Thr Glu Glu Tyr Glu Ser Thr
            35                  40                  45

Lys Glu Thr Leu Tyr Leu Leu Ser Asn Leu Gly Leu Met Arg Ile Glu
 50                  55                  60
```

<210> SEQ ID NO 103
<211> LENGTH: 78
<212> TYPE: PRT
<213> ORGANISM: Rickettsia conorii

<400> SEQUENCE: 103

```
Thr Leu Glu Ser Ala Glu Asp Leu Ala Tyr Trp Lys Lys Tyr Asp Ile
 1               5                  10                  15

Lys Lys Tyr Glu Arg Ile Lys Leu Leu Ile Lys Asn Ile Gln Glu Ala
                20                  25                  30

Pro Val Thr Gly Ile Gly Lys Pro Glu Pro Leu Lys His Ile Leu Ser
            35                  40                  45

Gly Leu Trp Ser Arg Arg Ile Asn His Glu His Arg Leu Ile Tyr Ser
 50                  55                  60

Val Asn Thr Lys Gln Ile Ile Ile Tyr Asn Cys Ser Phe His
```

65                  70                  75

<210> SEQ ID NO 104
<211> LENGTH: 75
<212> TYPE: PRT
<213> ORGANISM: Salmonella typhi

<400> SEQUENCE: 104

Met Phe Met Arg Thr Val Asn Tyr Ser Glu Ala Arg Gln Asn Leu Ala
1               5                   10                  15

Glu Val Leu Glu Ser Ala Val Thr Gly Gly Pro Val Thr Ile Thr Arg
            20                  25                  30

Arg Gly His Lys Ser Ala Val Ile Ile Ser Ala Glu Glu Phe Glu Arg
        35                  40                  45

Tyr Gln Thr Ala Arg Met Asp Asp Glu Phe Ala Ala Ile Met Ala Val
    50                  55                  60

His Gly Asn Glu Leu Arg Glu Leu Ala Asp Lys
65                  70                  75

<210> SEQ ID NO 105
<211> LENGTH: 122
<212> TYPE: PRT
<213> ORGANISM: Salmonella typhi

<400> SEQUENCE: 105

Met Thr Leu Gln Leu Ile Ser Ala Glu Glu Ile Ile Gln Phe His Asp
1               5                   10                  15

Arg Leu Leu Arg Val Thr Pro Gly Val Thr Gly Met Pro Asp Pro Gly
            20                  25                  30

Arg Ala Glu Ala Leu Met Tyr Arg Val Leu Lys Gln Ile Glu Tyr Glu
        35                  40                  45

Gly Val Thr Asp Val Trp Leu Leu Ala Ala Met His Leu Leu Ala Ile
    50                  55                  60

Ser Arg Gly His Ile Phe Asn Asp Gly Asn Lys Arg Thr Ala Leu Phe
65                  70                  75                  80

Ile Thr Leu Leu Phe Leu Lys Arg Asn Gly Ile Ser Leu Ala Ala Asn
                85                  90                  95

Pro Asp Phe Val Asp Met Thr Val Asp Ala Ala Ala Gly Arg Leu Thr
            100                 105                 110

Leu Glu Gln Ile Ala Val Arg Leu Arg Ala
        115                 120

<210> SEQ ID NO 106
<211> LENGTH: 83
<212> TYPE: PRT
<213> ORGANISM: Streptococcus aureus

<400> SEQUENCE: 106

Met Ile Ile Lys Asn Tyr Ser Tyr Ala Arg Gln Asn Leu Lys Ala Leu
1               5                   10                  15

Met Thr Lys Val Asn Asp Asp Ser Asp Met Val Thr Val Thr Ser Thr
            20                  25                  30

Asp Asp Lys Asn Val Val Ile Met Ser Glu Ser Asp Tyr Asn Ser Met
        35                  40                  45

Met Glu Thr Leu Tyr Leu Gln Gln Asn Pro Asn Asn Ala Glu His Leu
    50                  55                  60

Ala Gln Ser Ile Ala Asp Leu Glu Arg Gly Lys Thr Ile Thr Lys Asp
65                  70                  75                  80

Ile Asp Val

<210> SEQ ID NO 107
<211> LENGTH: 88
<212> TYPE: PRT
<213> ORGANISM: Streptococcus aureus

<400> SEQUENCE: 107

```
Met Ala Arg Leu Asn Ile Thr Phe Ser Pro Gln Ala Phe Glu Asp Tyr
1               5                   10                  15

Lys Tyr Phe Gln Gln Asn Asn Lys Lys Met Val Lys Lys Ile Asn Glu
            20                  25                  30

Leu Leu Lys Ser Ile Asp Arg Asn Gly Ala Leu Glu Gly Ile Gly Lys
        35                  40                  45

Pro Glu Lys Leu Lys Ser Asn Leu Thr Gly Tyr Tyr Ser Arg Arg Ile
50                  55                  60

Asn His Glu His Arg Leu Val Tyr Thr Val Asp Asp Asn His Ile Lys
65                  70                  75                  80

Ile Ala Ser Cys Lys Tyr His Tyr
                85
```

<210> SEQ ID NO 108
<211> LENGTH: 84
<212> TYPE: PRT
<213> ORGANISM: Streptococcus pneumoniae

<400> SEQUENCE: 108

```
Met Glu Ala Val Leu Tyr Ser Thr Phe Arg Asn His Leu Lys Asp Tyr
1               5                   10                  15

Met Lys Lys Val Asn Asp Glu Phe Glu Pro Leu Thr Val Val Asn Lys
            20                  25                  30

Asn Pro Asp Glu Asp Ile Val Val Leu Ser Lys Ser Glu Trp Asp Ser
        35                  40                  45

Ile Gln Glu Thr Leu Arg Ile Ala Gln Asn Lys Glu Leu Ser Asp Lys
    50                  55                  60

Val Leu Arg Gly Met Ala Gln Val Arg Ala Gly Ser Thr Gln Val His
65                  70                  75                  80

Val Ile Glu Glu
```

<210> SEQ ID NO 109
<211> LENGTH: 84
<212> TYPE: PRT
<213> ORGANISM: Streptococcus pneumoniae

<400> SEQUENCE: 109

```
Met Leu Leu Lys Phe Thr Glu Asp Ala Trp Ala Asp Tyr Cys Tyr Trp
1               5                   10                  15

Gln Asn Gln Asp Lys Lys Thr Leu Lys Arg Ile Asn Lys Leu Ile Lys
            20                  25                  30

Asp Ile Gln Arg Asp Pro Phe Thr Gly Ile Gly Lys Pro Glu Pro Leu
        35                  40                  45

Lys Tyr Asp Tyr Gln Gly Ala Trp Ser Arg Arg Ile Asp Ala Glu Asn
    50                  55                  60

Arg Leu Ile Tyr Met Met Asp Gly Asp Ser Val Ala Phe Leu Ser Phe
65                  70                  75                  80

Lys Asp His Tyr
```

<210> SEQ ID NO 110
<211> LENGTH: 87
<212> TYPE: PRT
<213> ORGANISM: Streptomyces coelicolor

<400> SEQUENCE: 110

Met Ser Ile Thr Ala Ser Glu Ala Arg Gln Asn Leu Phe Pro Leu Ile
1               5                   10                  15

Glu Gln Val Asn Glu Asp His Ala Pro Val His Ile Thr Ser Arg Lys
            20                  25                  30

Gly Asn Ala Val Leu Met Ser Glu Glu Asp Phe Thr Ala Trp Thr Glu
        35                  40                  45

Thr Val His Leu Leu Arg Ser Pro Arg Asn Ala Arg Arg Leu Leu Asp
    50                  55                  60

Ser Ile Ala Glu Ala Glu Ala Gly Asp Ala Thr Glu His Asp Leu Ile
65                  70                  75                  80

Asp Pro Asp Ala Glu Arg Ala
                85

<210> SEQ ID NO 111
<211> LENGTH: 84
<212> TYPE: PRT
<213> ORGANISM: Streptomyces coelicolor

<400> SEQUENCE: 111

Met Arg Ile Thr Phe Thr Ser His Gly Trp Glu Asp Tyr Val His Trp
1               5                   10                  15

Ala Glu Ser Asp Arg Lys Val Thr Lys Arg Ile Asn Arg Leu Ile Ala
            20                  25                  30

Asp Ile Ala Arg Asp Pro Phe Lys Gly Val Gly Lys Pro Glu Pro Leu
        35                  40                  45

Lys Gly Asp Leu Ser Gly Tyr Trp Ser Arg Arg Ile Asp Asp Thr His
    50                  55                  60

Arg Leu Val Tyr Lys Pro Thr Asp Asp Gln Leu Val Ile Val Gln Ala
65                  70                  75                  80

Arg Tyr His Tyr

<210> SEQ ID NO 112
<211> LENGTH: 93
<212> TYPE: PRT
<213> ORGANISM: Streptomyces viridochromogenes

<400> SEQUENCE: 112

Met Ser Ile Asn Arg Glu Arg Ser Arg Lys Ala Leu Phe Pro Leu Ile
1               5                   10                  15

Lys Lys Val Asn Asp Asn His Glu Ala Ile Glu Ile Val Ser Lys His
            20                  25                  30

Gly Asn Ala Val Leu Val Ser Ala Glu Asp Tyr Ala Ala Leu Arg Glu
        35                  40                  45

Gly Ser Tyr Leu Leu Arg Ser Pro Ala Asn Ala Arg Arg Leu Leu Lys
    50                  55                  60

Ala Tyr Glu Asn Ala Leu Ala His Val Asn Val Ser Glu Arg Glu Leu
65                  70                  75                  80

Ile Asp Pro Asp Ser Ala Asp Ala Gly Ser Gly Ala Ala
                85                  90

<210> SEQ ID NO 113

```
<211> LENGTH: 84
<212> TYPE: PRT
<213> ORGANISM: Streptomyces viridochromogenes

<400> SEQUENCE: 113

Met Arg Leu Val Phe Glu Asp Gln Gly Trp Asp Asp Tyr Thr Ser Trp
1               5                   10                  15

Leu Lys Asn Asp Arg Lys Met Leu Ala Arg Ile Asn Lys Leu Ile Glu
            20                  25                  30

Asp Val Arg Arg Asp Pro Phe Thr Gly Ile Gly Lys Pro Glu Pro Leu
        35                  40                  45

Lys Tyr His Leu Pro Gly Ala Trp Ser Arg Arg Ile Asp Asp Glu His
50                  55                  60

Arg Leu Val Tyr Leu Val Thr Asp Lys Glu Ile Val Ile Leu Ala Ala
65                  70                  75                  80

Arg Tyr His Tyr

<210> SEQ ID NO 114
<211> LENGTH: 100
<212> TYPE: PRT
<213> ORGANISM: Synechocystis sp. PCC 7942

<400> SEQUENCE: 114

Met Ala Lys Cys Tyr Cys Cys Thr Thr Ser Cys Thr Thr Pro Arg Leu
1               5                   10                  15

Met Lys Val Val Ser Phe Ser Asp Ala Arg Lys Asn Leu Lys Thr Val
            20                  25                  30

Leu Asp Glu Val Val Asn Asp Ala Asp Tyr Thr Ile Ile Thr Arg Arg
        35                  40                  45

Asn Ala Glu Glu Val Val Val Met Ser Leu Asp Ser Phe Asn Ser Leu
50                  55                  60

Ile Glu Thr Phe His Leu Leu Lys Ser Pro Ala Asn Ala Ala His Leu
65                  70                  75                  80

Gln Arg Ser Ile Ala Gln Tyr Gln Gln Gly Gln Thr Val Glu Arg Asn
                85                  90                  95

Leu Leu Asp Ala
            100

<210> SEQ ID NO 115
<211> LENGTH: 87
<212> TYPE: PRT
<213> ORGANISM: Synechocystis sp. PCC 7942

<400> SEQUENCE: 115

Met Arg Lys Leu Ala Trp Thr Asn Glu Ala Trp Glu Asp Tyr Leu Tyr
1               5                   10                  15

Trp Gln Gly Gln Asp Lys Lys Thr Leu Asn Arg Ile Asn Lys Leu Ile
            20                  25                  30

Thr Glu Thr Leu Arg Ser Pro Phe Glu Gly Ile Gly Lys Pro Glu Ala
        35                  40                  45

Leu Arg Glu Asn Leu Thr Gly Phe Trp Ser Arg Arg Ile Asp Asp Thr
50                  55                  60

Asn Arg Leu Val Tyr Ala Val Ala Asp Asp Tyr Leu Thr Ile Ile Ser
65                  70                  75                  80

Cys Arg Tyr His Tyr Ser Asp
                85
```

<210> SEQ ID NO 116
<211> LENGTH: 87
<212> TYPE: PRT
<213> ORGANISM: Synechocystis sp. PCC 6803 A

<400> SEQUENCE: 116

Met Lys Ala Ile Thr Thr Gln Ala Lys Asp His Leu Asp Glu Leu
1               5                   10                  15

Ile Asn Ala Val Ile Ser Asp Leu Glu Pro Thr Ile Val Ser Asn Asn
                20                  25                  30

Gln Gly Gln Gln Ala Val Leu Ile Ser Leu Asp Glu Phe Asn Ser Trp
            35                  40                  45

Gln Glu Thr Leu Tyr Leu Leu Ser Asn Pro Thr Asn Ala Glu His Leu
        50                  55                  60

Met Ala Ser Ile Lys Gln Ala Glu Thr Gly Gln Ile Ile Lys Gln Lys
65                  70                  75                  80

Leu Pro Asp Leu Leu Glu Leu
                85

<210> SEQ ID NO 117
<211> LENGTH: 86
<212> TYPE: PRT
<213> ORGANISM: Synechocystis sp. PCC 6803 A

<400> SEQUENCE: 117

Met Lys Ile Ala Phe Thr Glu Leu Ser Trp His Asp Tyr Leu Trp Phe
1               5                   10                  15

Gln Gln Asn Asp Lys Lys Leu Leu Lys Arg Ile Asn Leu Leu Ile Lys
                20                  25                  30

Ala Ile Ala Arg Asp Pro Phe Asp Gly Ile Gly Lys Pro Glu Pro Leu
            35                  40                  45

Lys Ala Asn Leu Ser Gly Tyr Trp Ser Arg Arg Ile Asn Ser Glu His
        50                  55                  60

Arg Leu Val Tyr Thr Ile Ala Asp Arg Asp Leu Leu Ile Ile Ser Cys
65                  70                  75                  80

Arg Phe His Tyr Gln Arg
                85

<210> SEQ ID NO 118
<211> LENGTH: 87
<212> TYPE: PRT
<213> ORGANISM: Synechocystis sp. PCC 6803 B

<400> SEQUENCE: 118

Met Glu Thr Ile Asn Tyr Gln Gln Phe Ser Glu Lys Leu Pro Thr Leu
1               5                   10                  15

Val Glu Lys Ile Gly Asn Glu Gln Glu Pro Leu Cys Leu Glu Leu Pro
                20                  25                  30

Asn Tyr Leu Arg Ala Val Ile Ser Glu Gln Asp Tyr Arg Ser Leu
            35                  40                  45

Met Glu Thr Val Tyr Leu Leu Ser Asn Pro Val Asn Ala Glu Lys Leu
        50                  55                  60

Leu Thr Thr Ala Ser Arg Ser Ile Asp Gln Ala Thr Ser Trp Thr Lys
65                  70                  75                  80

Val Lys Asn Asp Leu Gly Leu
                85

<210> SEQ ID NO 119

```
<211> LENGTH: 86
<212> TYPE: PRT
<213> ORGANISM: Synechocystis sp. PCC 6803 B

<400> SEQUENCE: 119
```

Met Lys Glu Val Val Leu Asp Ser Gln Ala Ile Glu Asp Ile Lys Trp
1               5                   10                  15

Trp Ile Gln Gln Asp Lys Lys Leu Ala Leu Lys Ile Met Glu Leu Ile
            20                  25                  30

Glu Thr Leu Pro Lys Ser Pro Phe Ala Gly Lys Gly Lys Pro Glu Lys
        35                  40                  45

Leu Arg Phe Asn Leu Ser Gly Phe Trp Pro Arg Ile Thr Gln Glu
    50                  55                  60

His Arg Leu Val Tyr Glu Val Thr Asp Asp Phe Ile Arg Val Val Ser
65                  70                  75                  80

Cys Arg Tyr His Tyr Arg
                85

```
<210> SEQ ID NO 120
<211> LENGTH: 80
<212> TYPE: PRT
<213> ORGANISM: Tiobacillus ferroxidant

<400> SEQUENCE: 120
```

Met Ser Thr Leu Thr Ala Ser Glu Ala Arg Ala Asn Leu Tyr Arg Leu
1               5                   10                  15

Ile Asp Gln Ala Ala Glu Ser His Gln Pro Ile Tyr Ile Ala Gly Lys
            20                  25                  30

Arg Thr Ser Ala Val Leu Leu Ser Thr Glu Asp Trp Glu Ala Ile Gln
        35                  40                  45

Glu Thr Leu Tyr Leu Leu Ser Val Pro Gly Met Arg Glu Ser Ile Lys
    50                  55                  60

Glu Gly Met Ala Glu Pro Leu Ser Lys Ser Asn Met Asp Leu Lys Trp
65                  70                  75                  80

```
<210> SEQ ID NO 121
<211> LENGTH: 83
<212> TYPE: PRT
<213> ORGANISM: Tiobacillus ferroxidant

<400> SEQUENCE: 121
```

Met Val Tyr Ser Lys His Ala Gln Lys Asp Ala Lys Lys Leu Ala Ala
1               5                   10                  15

Ala Gly Leu Lys Asn Asn Ala Ile Glu Leu Leu Ala Val Leu Ala Ala
            20                  25                  30

Asp Pro Phe Gln Asn Pro Pro Tyr Glu Asn Leu Val Gly Asp Leu
        35                  40                  45

Ala Gly Ala Tyr Ser Arg Arg Ile Asn Ile Gln His Arg Leu Val Tyr
    50                  55                  60

Glu Val Phe Pro Lys Glu Arg Val Val Arg Val Leu Arg Met Trp Thr
65                  70                  75                  80

His Tyr Glu

```
<210> SEQ ID NO 122
<211> LENGTH: 83
<212> TYPE: PRT
<213> ORGANISM: Yersinia enterocolitica

<400> SEQUENCE: 122
```

-continued

Met Arg Thr Ile Ser Tyr Ser Glu Ala Arg Gln Asn Leu Ser Thr Thr
1 5 10 15

Met Val Gln Thr Val Glu Asp Arg Ala Pro Ile Leu Ile Thr Arg Gln
20 25 30

Asn Gly Thr Ser Cys Val Leu Met Ser Leu Glu Glu Tyr Glu Ser Leu
35 40 45

Glu Glu Thr Ala Tyr Leu Leu Arg Ser Pro Ala Asn Ala Lys His Leu
50 55 60

Met Asp Ser Ile Glu Glu Leu Arg Ala Gly Lys Gly Ile Gln Arg Glu
65 70 75 80

Leu Glu Ala

<210> SEQ ID NO 123
<211> LENGTH: 84
<212> TYPE: PRT
<213> ORGANISM: Yersinia enterocolitica

<400> SEQUENCE: 123

Met Lys Ile Ile Phe Ser Ser Cys Ser Trp Glu Asp Tyr Leu Tyr Trp
1 5 10 15

Gln Gln Thr Asp Lys Lys Ile Leu Lys Arg Ile Asn Gly Leu Val Lys
20 25 30

Asn Ile Gln Arg Thr Pro Phe Glu Val Lys Gly Lys Pro Glu Pro Leu
35 40 45

Lys His Asn Leu Ala Gly Phe Trp Ser Arg Arg Met Thr Glu Glu His
50 55 60

Arg Leu Val Tyr Glu Val Ser Gly Asp Asn Leu Leu Ile Ala Ala Tyr
65 70 75 80

Arg Tyr Tyr Tyr

<210> SEQ ID NO 124
<211> LENGTH: 69
<212> TYPE: PRT
<213> ORGANISM: Yersinia enterocolitica

<400> SEQUENCE: 124

Met Asn Ser Ile Ser Tyr Thr Ala Ala Arg Asn Asn Leu Ala Lys Val
1 5 10 15

Leu Leu Glu Ala Gln Lys Gln Pro Val Glu Ile Thr Arg Arg Gly Gln
20 25 30

Ser Glu Val Tyr Ile Ile Ser Lys Ala Asp Tyr Glu Asp Leu Met Lys
35 40 45

Ala Lys Val Lys Ala His Ile Gln Phe Lys His Ala Glu Thr Ile Lys
50 55 60

Ala Leu Ala Asp Arg
65

<210> SEQ ID NO 125
<211> LENGTH: 118
<212> TYPE: PRT
<213> ORGANISM: Yersinia enterocolitica

<400> SEQUENCE: 125

Met Ile Phe Leu Thr Ala Asn Asp Ile Ala Glu Phe Asn Ala Glu Ile
1 5 10 15

Ile Pro Asn Gly Arg Pro Asp Asn Ser Lys Ile Glu Ala Val Ala Ser
20 25 30

```
Arg Val Leu Asn Ala His His Tyr Asp Asn Val Asp Asp Val Tyr Gln
            35                  40                  45

Leu Ala Ala Ile Tyr Leu Ile Ala Ile Ser Arg Gly His Ile Phe Leu
    50                  55                  60

Asp Gly Asn Lys Arg Thr Ala Phe Gln Ser Met Ala Leu Phe Leu Gly
65                  70                  75                  80

Ile Asn Gly Val Asp Leu Cys Ala Ser Asn Gln Leu Glu Glu Leu Thr
                85                  90                  95

Val Glu Ala Ala Gln Gly Lys Ile Gly Val Glu Gln Ile Thr Glu Gln
            100                 105                 110

Leu Arg Glu Leu Thr Glu
        115

<210> SEQ ID NO 126
<211> LENGTH: 20
<212> TYPE: DNA
<213> ORGANISM: Artificial sequence
<220> FEATURE:
<223> OTHER INFORMATION: Antisense sequence for YefM antitoxin

<400> SEQUENCE: 126
ggatcggggc atgatcttca                                              20

<210> SEQ ID NO 127
<211> LENGTH: 21
<212> TYPE: DNA
<213> ORGANISM: Artificial sequence
<220> FEATURE:
<223> OTHER INFORMATION: SiRNA oligonucleotide

<400> SEQUENCE: 127
gccguugaag aucaugcccu t                                            21

<210> SEQ ID NO 128
<211> LENGTH: 21
<212> TYPE: DNA
<213> ORGANISM: Artificial sequence
<220> FEATURE:
<223> OTHER INFORMATION: SiRNA oligonucleotide

<400> SEQUENCE: 128
gggcaugauc uucaacggct t                                            21

<210> SEQ ID NO 129
<211> LENGTH: 17
<212> TYPE: PRT
<213> ORGANISM: Artificial sequence
<220> FEATURE:
<223> OTHER INFORMATION: Synthetic peptide

<400> SEQUENCE: 129

Arg Thr Ile Ser Tyr Ser Glu Ala Arg Gln Asn Leu Ser Ala Thr Met
1               5                   10                  15
Met

<210> SEQ ID NO 130
<211> LENGTH: 13
<212> TYPE: PRT
<213> ORGANISM: Artificial sequence
<220> FEATURE:
<223> OTHER INFORMATION: Synthetic peptide

<400> SEQUENCE: 130
```

-continued

```
Ala Pro Ile Leu Ile Thr Arg Gln Asn Gly Glu Ala Cys
1               5                   10

<210> SEQ ID NO 131
<211> LENGTH: 16
<212> TYPE: PRT
<213> ORGANISM: Artificial sequence
<220> FEATURE:
<223> OTHER INFORMATION: Synthetic peptide

<400> SEQUENCE: 131

Met Asp Ser Ile Asp Ser Leu Lys Ser Gly Lys Gly Thr Glu Lys Asp
1               5                   10                  15

<210> SEQ ID NO 132
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 132
ataatgataa cgacacgctg                                                20
```

ANTIBACTERIAL AGENTS AND METHODS OF IDENTIFYING AND UTILIZING SAME

RELATED APPLICATIONS

This application is a National Phase Application of PCT Patent Application No. PCT/IL2004/000898 having International Filing Date of Sep. 27, 2004, which claims the benefit of U.S. Provisional Patent Application No. 60/507,488 filed on Oct. 2, 2003 and U.S. Provisional Patent Application No. 60/550,334 filed on Mar. 8, 2004. The contents of the above Applications are all incorporated herein by reference.

FIELD AND BACKGROUND OF THE INVENTION

The present invention relates to methods of identifying antibacterial agents and more particularly, to novel antibacterial agents which are capable of preventing or disrupting binding between antitoxin and toxin polypeptides of bacterial cells.

Presently, treatment of infections caused by pathogenic bacteria relies predominantly on the administration of antibiotics. Antibiotics currently being used against bacterial pathogens include β-lactams (e.g., penicillin and cephalosporin) and glycopeptides (e.g., vancomycin and teichoplanin), which act to inhibit the final step in peptidoglycan synthesis, quinolones, which inhibit bacterial DNA replication, inhibitors of bacterial RNA polymerase such as rifampin, and aminoglycosides (e.g., kanamycin and gentamycin). Other well-known antibiotics include inhibitors of enzymes participating in production of tetrahydrofolate (e.g., sulfonamides).

Despite being successful in controlling or eliminating bacterial infections, widespread use of antibiotics both in human medicine and as a feed supplement in poultry and livestock production has led to drug resistance in many pathogenic bacteria (McCormick J. B., Curr Opin Microbiol 1:125-129, 1998) and as such, the effectiveness of such antibiotics has greatly diminished in the last decade.

The rapid and widespread development of resistance in pathogenic bacteria is illustrated by the fact that presently almost half of the clinical strains of *Haemophilus ducreyi*, the causative agent of chancroid, carry genes which confer resistance to amoxicillin, ampicillin and a series of other β-lactams (Prachayasittikul et al., Southeast Asian J Trop Med Public Health 31:80-84, 2000). Likewise, the incidence of resistance towards tetracyclines among clinical strains of *Salmonella typhimurium* has increased from zero in 1948 to 98% by 1998 (Teuber M., Cell Mol Life Sci 30:755-763, 1999).

The economic impact of managing infections caused by antibiotic-resistant bacteria is substantial, and current costs are estimated to be more than $4 billion annually [Harrison and Lederberg (ed.), Antimicrobial resistance: issues and options. National Academy Press, Washington, D.C. pp. 1-7, 1998]. Furthermore, as resistance spreads among bacteria, there is grave concern that antibiotics treatment will become increasingly less effective and, in some cases, completely ineffective.

This rapidly increasing appearance of bacterial resistance to antibiotics has driven researchers to search for new agents that possess activity against antibacterial drug-resistant strains. Although several approaches can be utilized to achieve this goal, the most generalized would be the discovery and clinical development of an agent that acts on a new target which has not yet experienced selective pressure in the clinical setting. Such a target should be essential to the growth and survival of bacteria and be sufficiently different from similar macromolecules present in the human host (Goldman and Gange, Curr Med Chem 7:801-820, 2000).

The Toxin-antitoxin complex of bacteria includes a pair of polypeptides that is encoded by bacterial plasmids and chromosomes. It is postulated that in bacteria these polypeptides function to induce programmed cell death or growth inhibition in response to starvation or other adverse conditions (Hayes, Science 301:1496-1499, 2003). The antitoxins neutralize the cognate toxins by forming tight complexes therewith. The antitoxins are unstable due to degradation by cellular proteases (e.g., Lon or Clp), whereas toxins are stable polypeptides. Toxin-antitoxin pair examples include the pemI-pemK genes of plasmid R100, the phd-doc genes of phage P1, and the ccdA-ccdB genes, of plasmid F (Couturier et al., Trends Microbiol. 6:269-275, 1998; Engelberg-Kulka and Glaser, Annu. Rev. Microbiol 53:43-70, 1999; Jensen and K Gerdes, Mol. Microbiol. 17:205-210, 1995). Toxin-antitoxin pairs are thought to increase the stability of extrachromosomal elements by selectively killing plasmid-free cells, resulting in the proliferation of plasmid-harboring cells in the population (Holcík and Iyer, Microbiology 143:3403-3416, 1997; and Grady and Hayes, Mol. Microbiol. 47:1491-1432, 2003). Several toxin-antitoxin encoding gene analogues have been identified on the *E. coli* K-12 chromosome, such as mazE-mazF (also known as chpAI-chpAK), sof-gef, kicA-kicB, relB-relE, chpBI-chpBK and yefM-yoeB (Grady and Hayes, Mol. Microbiol. 47:1491-1432, 2003; Aizenman et al., Proc. Natl. Acad. Sci. USA 93:6059-6063, 1996; Feng et al., Mol. Gen. Genet. 243:136-147, 1994; Gotfredsen and Gerdes, Mol. Microbiol. 29:1065-1076, 1998; Masuda et al., J. Bacteriol. 175:6850-6856, 1993, and Poulsen et al., Mol. Microbiol. 3:1463-1472, 1989).

Although the use of toxin encoding polynucleotides for inducing bacterial cell death has been recently suggested (Westwater et al., Antimicrobial Agents and Chemotherapy 47: 1301-1307, 2003), the prior art does not teach or suggest prevention or disruption of toxin-antitoxin binding for the purpose of inducing death in bacterial cells.

While reducing the present invention to practice, the present inventors have identified the site of interaction between bacterial toxin and antitoxin polypeptides thus enabling for the first time to identify or design novel antibiotics which target this site of interaction and thus enable bacterial cell killing.

SUMMARY OF THE INVENTION

According to one aspect of the present invention there is provided a method of identifying a molecule capable of inducing death of a bacterial cell. The method includes (i) exposing toxin and antitoxin polypeptides of a toxin-antitoxin pair produced by the bacterial cell to a plurality of molecules; and (ii) identifying a molecule of the plurality of molecules capable of preventing or disrupting binding between the antitoxin and the toxin polypeptides.

According to another aspect of the present invention there is provided a method of treating an infection of bacteria in a subject. The method includes preventing or disrupting binding between a toxin and an antitoxin polypeptides of a toxin-antitoxin pair produced in the bacteria.

According to yet another aspect of the present invention there is provided a pharmaceutical composition for treating an infection of bacteria which includes an effective amount of an agent capable of preventing or disturbing binding between a toxin and an antitoxin polypeptides of a toxin-antitoxin pair produced in the bacteria.

According to still another aspect of the present invention there is provided a method of identifying toxin and antitoxin polypeptides of a toxin-antitoxin pair. The method includes (i) identifying bacterial polynucleotide sequences at least partially homologous to polynucleotide sequences encoding known bacterial toxin and antitoxin polypeptides to thereby obtain a plurality of toxin and antitoxin encoding sequences; and (ii) determining a chromosomal position of each of the plurality of sequences, wherein toxin and antitoxin encoding sequences which are chromosomally positioned at a distance from each other which is no greater than a predetermined value encode a toxin-antitoxin pair.

According to further features in preferred embodiments of the invention described below, exposing toxin and antitoxin polypeptides of a toxin-antitoxin pair produced by the bacterial cell to a plurality of molecules is effected by administering the plurality of molecules to bacteria expressing the toxin and antitoxin polypeptides.

According to still further features in the described preferred embodiments, the antitoxin polypeptide is an unfolded polypeptide.

According to still further features in the described preferred embodiments, the antitoxin polypeptide includes an amino acid sequence selected from the group consisting of SEQ ID NOs. 68, 70, 72, 74, 76, 78, 80, 82, 84, 86, 88, 90, 92, 94, 96, 98, 100, 102, 104, 106, 108, 110, 112, 114, 116, 118, 120, 122 and 124.

According to still further features in the described preferred embodiments, the antitoxin polypeptide is encoded by a polynucleotide sequence selected from the group consisting of SEQ ID NOs. 10, 12, 14, 16, 18, 20, 22, 24, 26, 28, 30, 32, 34, 36, 38, 40, 42, 44, 46, 48, 50, 52, 54, 56, 58, 60, 62, 64 and 66.

According to still further features in the described preferred embodiments, the toxin polypeptide includes an amino acid sequence selected from the group consisting of SEQ ID NOs. 69, 71, 73, 75, 77, 79, 81, 83, 85, 87, 89, 91, 93, 95, 97, 99, 101, 103, 105, 107, 109, 111, 113, 115, 117, 119, 121, 123 and 125.

According to still further features in the described preferred embodiments the toxin polypeptide is encoded by a polynucleotide sequence selected from the group consisting of SEQ ID NOs. 11, 13, 15, 17, 19, 21, 23, 25, 27, 29, 31, 33, 35, 37, 39, 41, 43, 45, 47, 49, 51, 53, 55, 57, 59, 61, 63, 65 and 67.

According to still further features in the described preferred embodiments, preventing or disrupting binding between the toxin and the antitoxin polypeptides is effected by providing to the subject an agent selected from the group consisting of (i) a compound which specifically binds to the antitoxin or to the toxin; (ii) an antisense polynucleotide capable of specifically hybridizing with an mRNA transcript encoding the antitoxin; (iii) a ribozyme which specifically cleaves transcripts encoding the antitoxin; and (iv) a small interfering RNA (siRNA) molecule which specifically cleaves the antitoxin transcripts.

According to still further features in the described preferred embodiments the compound is selected from the group consisting of a peptide, a polynucleotide, a polysaccharide, a small organic compound and a non-biological compound.

According to still further features in the described preferred embodiments the compound which specifically binds to the antitoxin is an antibody or an antibody fragment.

According to still further features in the described preferred embodiments the bacteria are pathogenic bacteria.

According to still further features in the described preferred embodiments the subject is a mammal.

According to still further features in the described preferred embodiments the subject is a human.

According to still further features in the described preferred embodiments the peptide is derived from the toxin or from the antitoxin.

According to still further features in the described preferred embodiments the peptide includes an amino acid sequence selected from group consisting of SEQ ID NOs: 7-9.

According to still further features in the described preferred embodiments, the agent is a polynucleotide capable of specifically hybridizing with an mRNA transcript encoding the antitoxin.

According to still further features in the described preferred embodiments, the agent is a ribozyme which specifically cleaves transcripts encoding the antitoxin.

According to still further features in the described preferred embodiments, the agent is a small interfering RNA (siRNA) molecule which specifically cleaves the antitoxin transcripts.

According to still further features in the described preferred embodiments, the predetermined value is ranging between 10 base pair to 150 base pair.

The present invention successfully addresses the shortcomings of the presently known configurations by providing methods of identifying novel antibacterial agents which are capable of preventing or disrupting binding between antitoxin and toxin polypeptides of bacterial cells and pharmaceutical compositions comprising these agents for treating bacterial infections.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
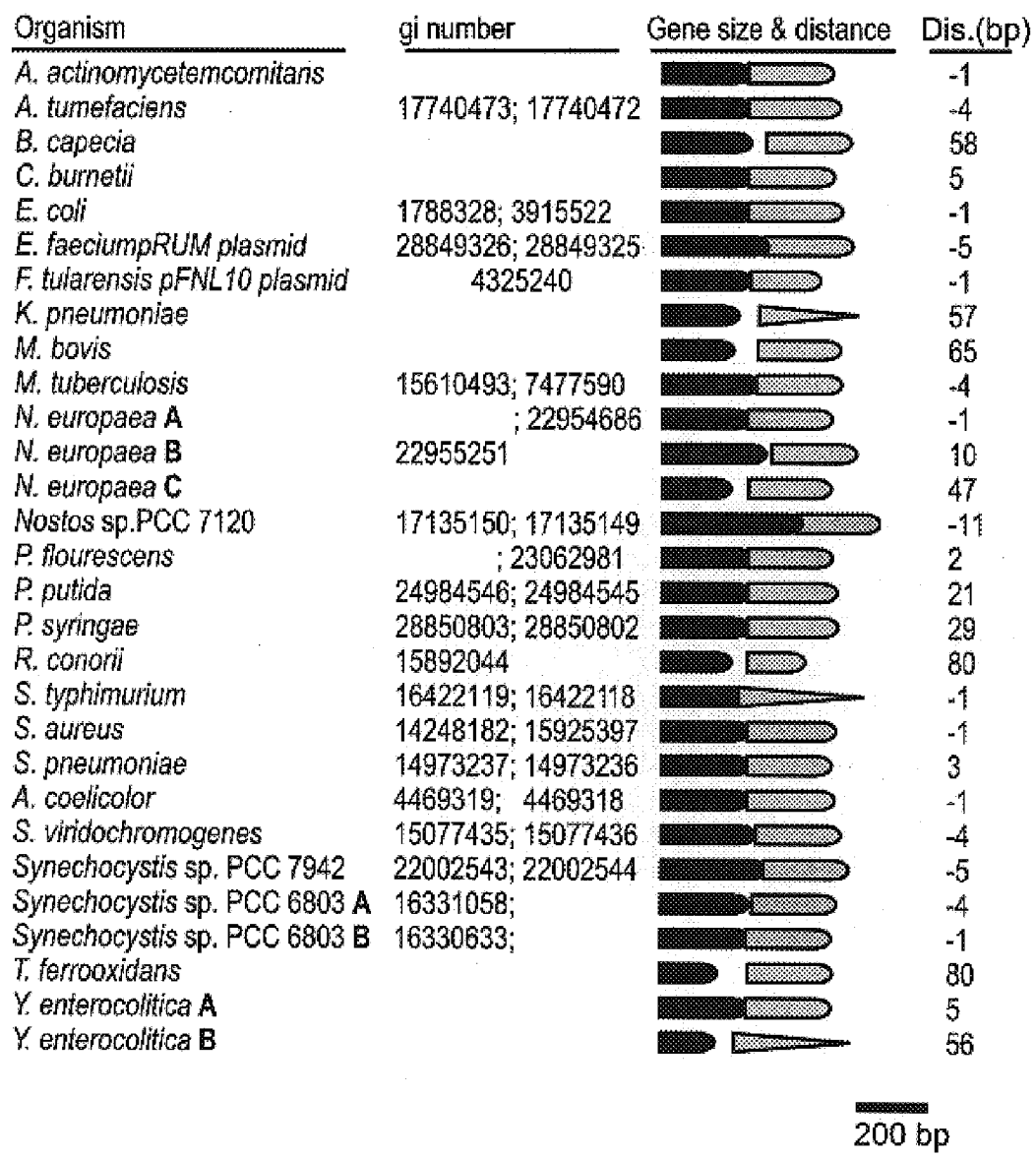

FIG. 1 illustrates yoeB and yefM pair homologue sequences identified in different bacterial genomes. These homologue sequences were separated by less than 100 base pairs in their respective bacterial genomes and thus were selected for further analysis. The black half-ovals represent yefM homologues and the gray half-ovals represent yoeB homologue sequences. The sharp gray arrowheads represent doc homologue sequences. Missing gi numbers indicate annotated open reading frames (ORFs).

Figure 2A:
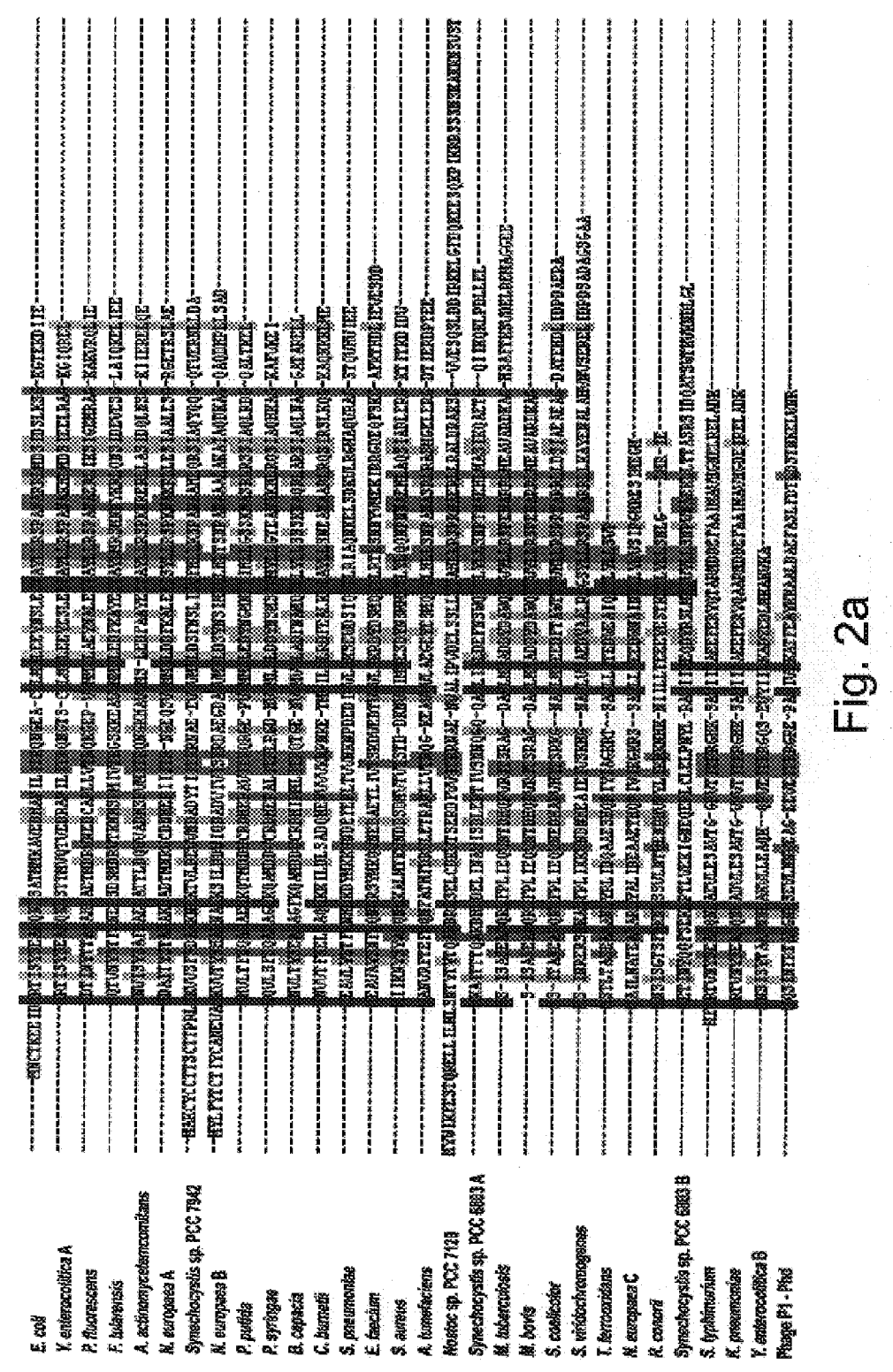

FIG. 2A illustrates a multiple sequence alignment of YefM polypeptide homologues. The alignment list includes 30 sequences from 25 different bacteria (different homologues which exist in the same bacteria are presented in alphabetical order). Polypeptide sections having sequence identity of ≧80%, ≧60% and ≧40% are colored in dark, medium and light blue background, respectively. The identity percentage values were determined by using a BLOSUM62 matrix.

Figure 2B:
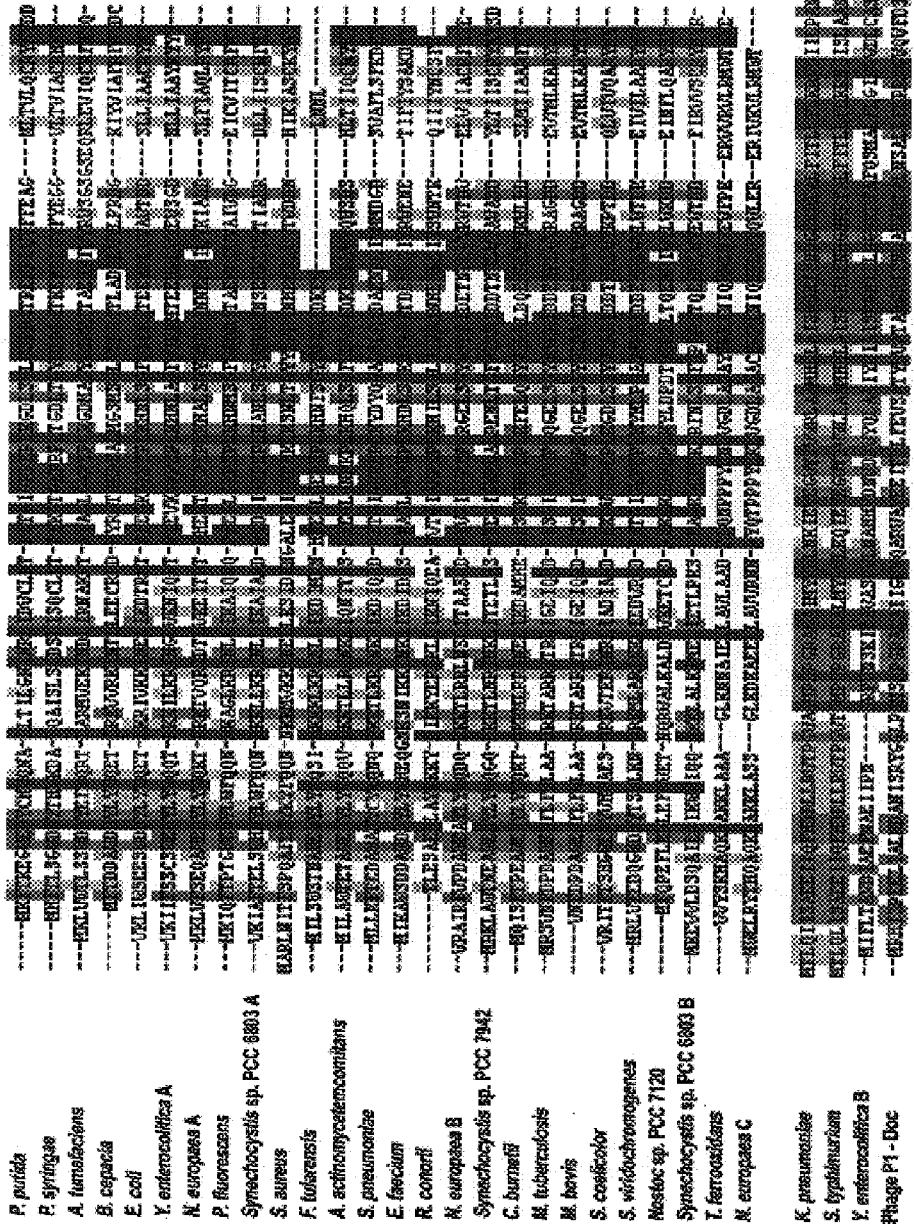

FIG. 2B illustrates a multiple sequence alignment of YoeB polypeptide homologues. Polypeptide sections having sequence identity of ≧80%, ≧60% and ≧40% are colored in dark, medium and light blue background, respectively. The identity percentage values were determined by using a BLOSUM62 matrix. The upper alignment list illustrates 26 amino acid sequences obtained from 22 different bacteria, all showing substantial homology to the YoeB polypeptide. The lower alignment list illustrates three Doc homologue sequences.

Figure 3A:
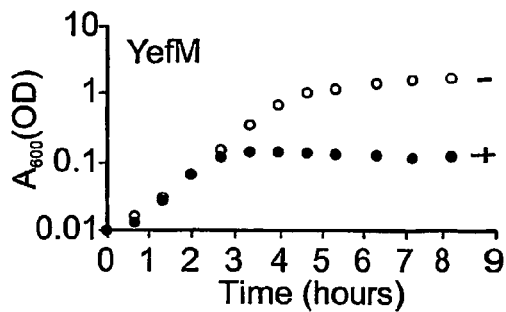
Figure 3B:
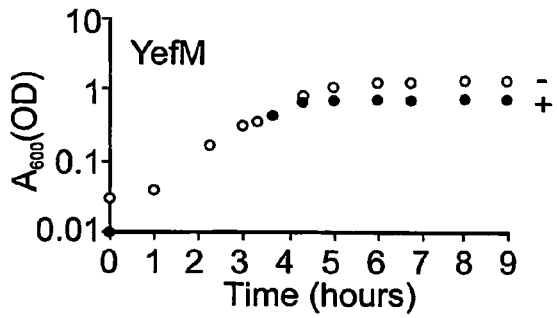
Figure 3C:
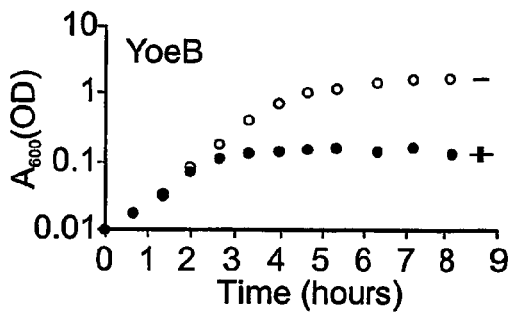
Figure 3D:
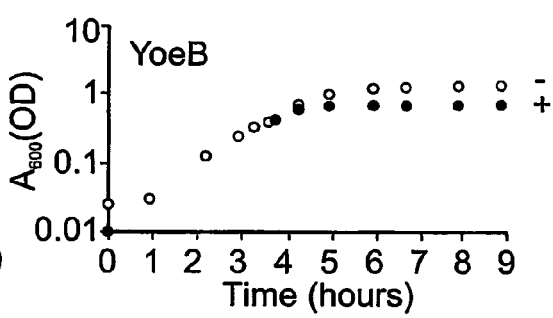
Figure 3E:
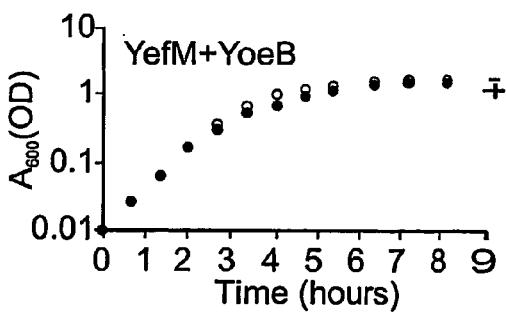
Figure 3F:
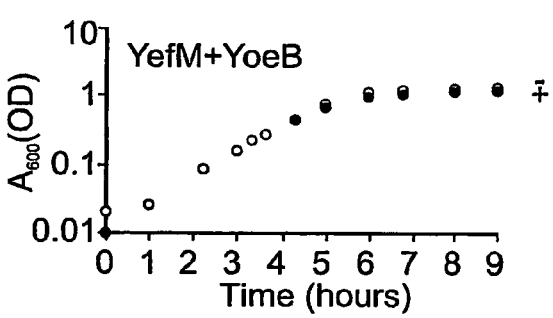
Figure 3G:
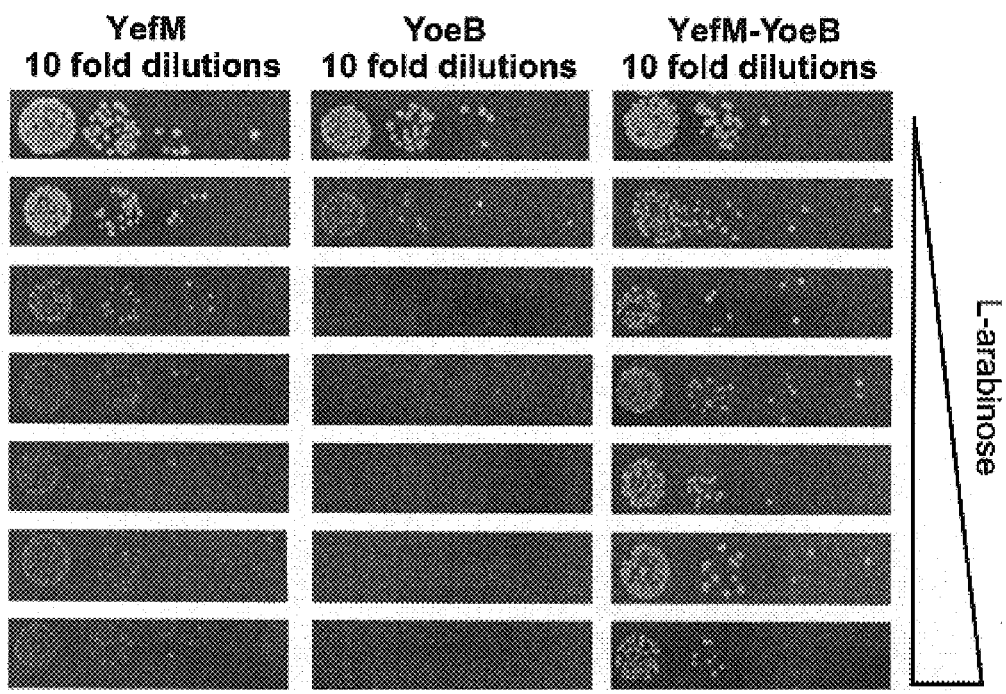

FIGS. 3A-G illustrate the function of the YoeB and YefM polypeptides as a toxin-antitoxin pair in vivo. Bacteria (*E. coli* strain TOP10) expressing YefM only (FIGS. 3A and 3D), expressing YoeB only (FIGS. 3B and 3E), or expressing YoeB and YefM combined (FIGS. 3C and 3F), were grown in LB-Amp at 37° C. Transcription of the polypeptides was induced by supplementing 0.2% L-arabinose (full circles) to the stationary growth phase at time zero (FIGS. 3A-C), or at the logarithmic growth phase, when cultures reached an $OD_{600}$ of 0.45 (FIGS. 3D-F). As a negative control, parallel cultures were supplemented with 0.2% glucose (open circles). FIG. 3G illustrates the effect of overexpressing YefM alone, YoeB alone, or YoeB and YefM combined, on bacterial colony formation. Bacterial suspension droplets were added, in serial ten-fold dilutions, onto solid media supplemented with different concentrations of L-arabinose (0%, 0.0005%, 0.005%, 0.02%, 0.05%, 0.1%, and 0.2%) and incubated at 37° C. for 20 hours. Cultures missing L-arabinose were supplemented with 0.2% glucose. The resulting colony formation of bacteria expressing YoeB alone was inversely proportional to L-arabinose concentrations, while colony formation of bacteria expressing YoeB and YefM combined was unaffected by the L-arabinose concentration.

Figure 4A:
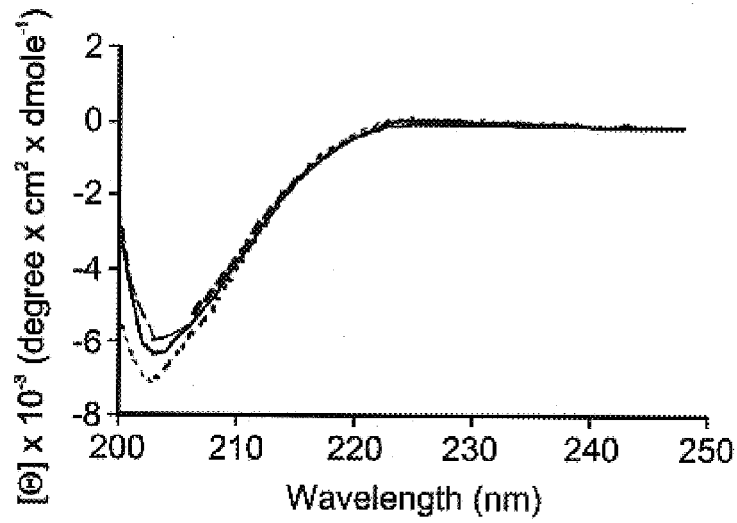
Figure 4B:
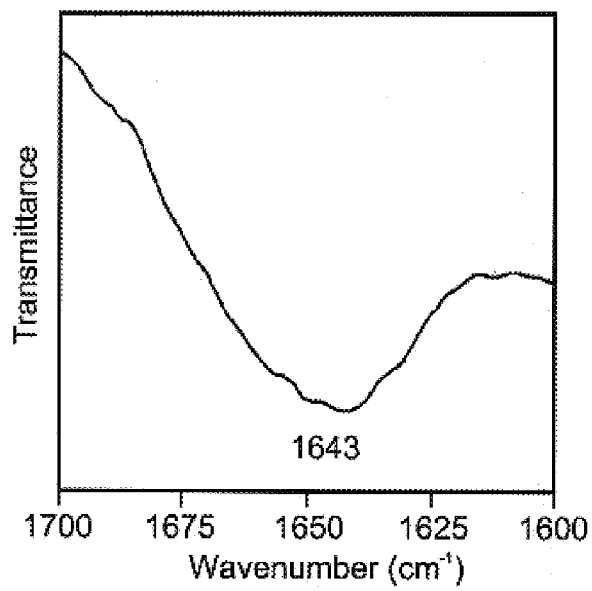
Figure 4C:
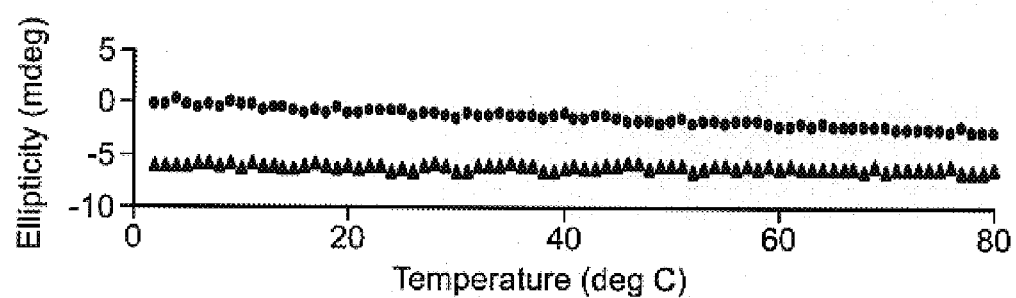
Figure 4D:
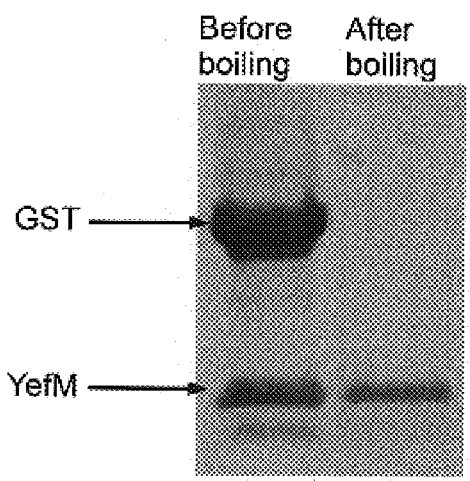

FIGS. 4A-D illustrate the native unfolded state of the YefM antitoxin polypeptide. FIG. 4A shows spectra of far UV circular-dichroism (CD) of YefM in PBS (pH 7.3) at 25° C. ( - - - ), 37° C. (———), and 42° C. (— —), indicating a random coil structure. FIG. 4B illustrates spectra of Fourier Transform Infrared of the YefM polypeptide having a minimum transmittance at wave-number of 1643 $cm^{-1}$ indicating a random coil structure. FIG. 4C illustrates the thermal stability of YefM at 2° C. to 80° C. temperature range. The thermal stability of YefM was determined by monitoring CD ellipticity at 217 nm (triangles) and 222 nm (circles) as a function of temperature. FIG. 4D shows an SDS-PAGE analysis illustrating solubility of the YefM polypeptide which survived a boiling treatment. The left lane illustrates SDS-PAGE of YefM-GST sample following cleavage. The right lane illustrates an SDS-PAGE of the supernatant of the same sample following boiling for 10 minutes and centrifugation.

Figure 5A:
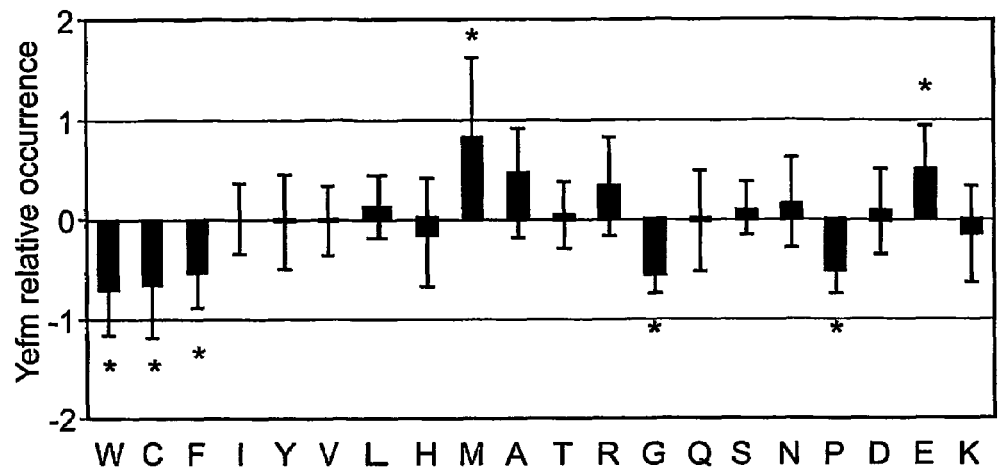

FIG. 5A illustrates the relative occurrence of amino acids in YefM family of polypeptides, in relation to the general occurrence of amino acids in polypeptide compositions [based on NCBI proteins database (22)]. Error bars represent standard deviations and the asterisks indicate statistically significant differences at $P<0.001$. This figure illustrates that the YefM family of polypeptides are uniquely enriched in the amino acids M and E and uniquely depleted in the amino acids W, C, P, F and G.

Figure 5B:
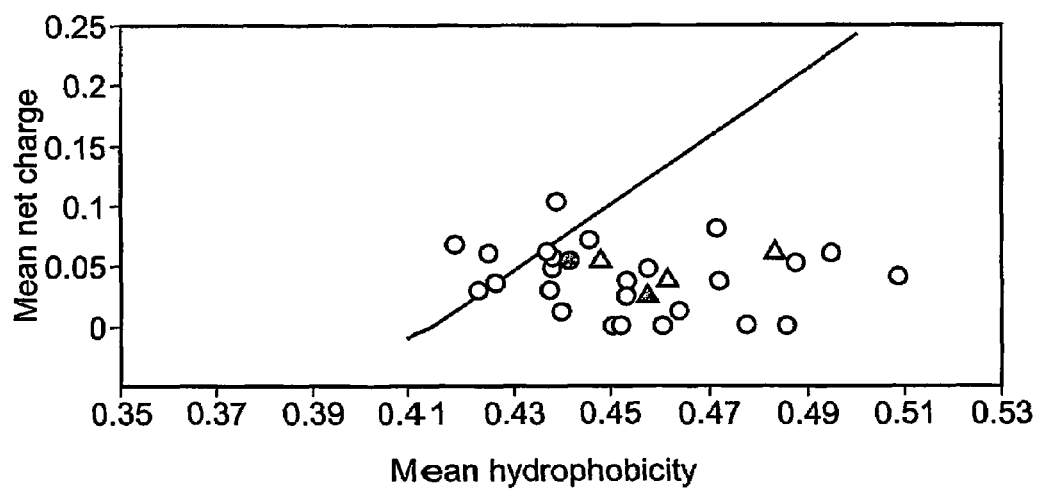

FIG. 5B illustrates the calculated net charge and hydrophobicity of polypeptide homologues of YefM (circles) and Phd (triangles). The solid line represents Uversky et al. model (3) separating presumptive unfolded polypeptides (upper left area) from folded polypeptides (bottom right area).

Figure 6A:
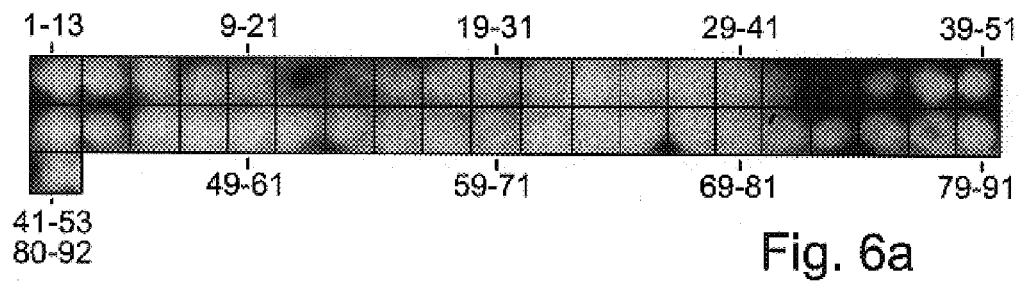
Figure 6B:
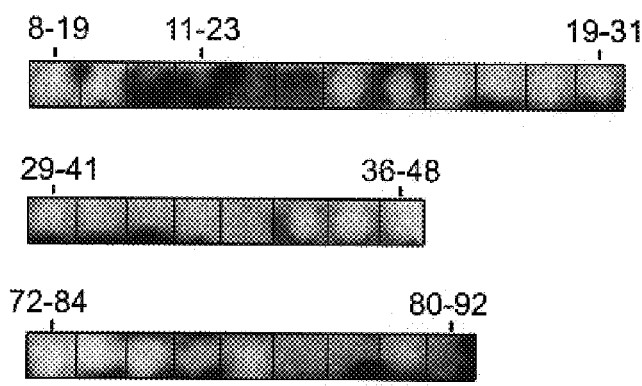
Figure 6C:
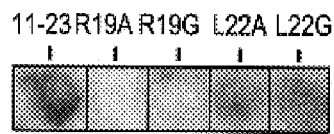

FIGS. 6A-C are peptide array analyses identifying a YefM derivative which contains the antitoxin binding determinant.

FIG. 6A illustrates an array of tridecamer peptides corresponding to consecutive overlapping sequences of 92 amino acids of the YefM polypeptide (two amino-acids shift between peptides). A YoeB-GST bound to the membrane is positively identified in $YefM_{11-23}$-$YefM_{15-27}$, $YefM_{33-45}$, $YefM_{75-87}$ and $YefM_{77-89}$ peptides. FIG. 6B illustrates a similar array of peptides corresponding to consecutive overlapping sequences of $YefM_{8-31}$, $YefM_{29-48}$, and $YefM_{72-92}$ (single amino-acid shift between peptide), indicating that the best binding of YoeB-GST was to $YefM_{11-23}$. FIG. 6C illustrates of $YefM_{11-23}$ analogs having single amino acid replacements. $YefM_{11-23}$ analogs having arginine in position 19 of the $YefM_{11-23}$ sequence, which was replaced with either alanine or glycine, were unable to bind YoeB-GST.

Figure 7A:
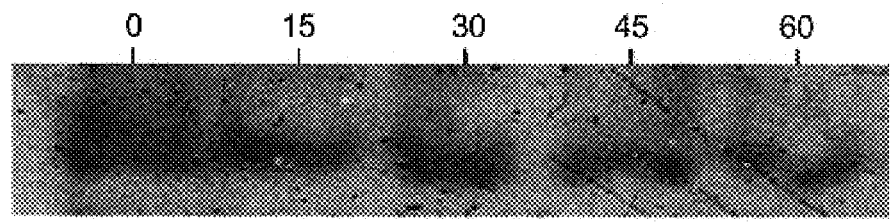
Figure 7B:
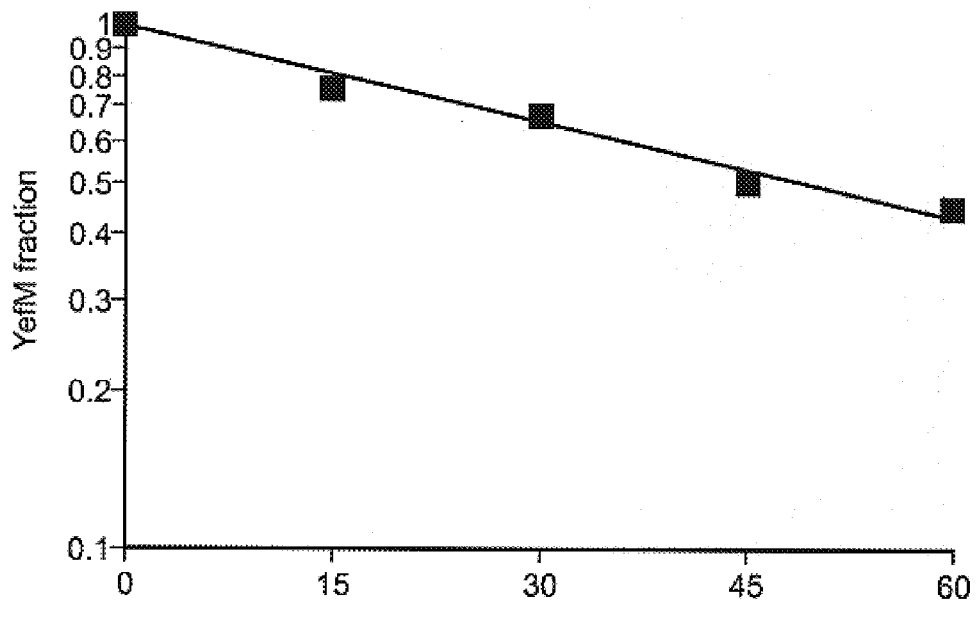

FIGS. 7A-B illustrate the instability of the YefM antitoxin in vivo. Expression of YefM in *E. coli* TOP10 was briefly induced then repressed Following repression, samples taken sequentially at different time intervals were analyzed for YefM expression by western blot analysis (FIG. 7A) and by densitometer (FIG. 7B), indicating a half-life of about one hour for this polypeptide.

Figure 8:
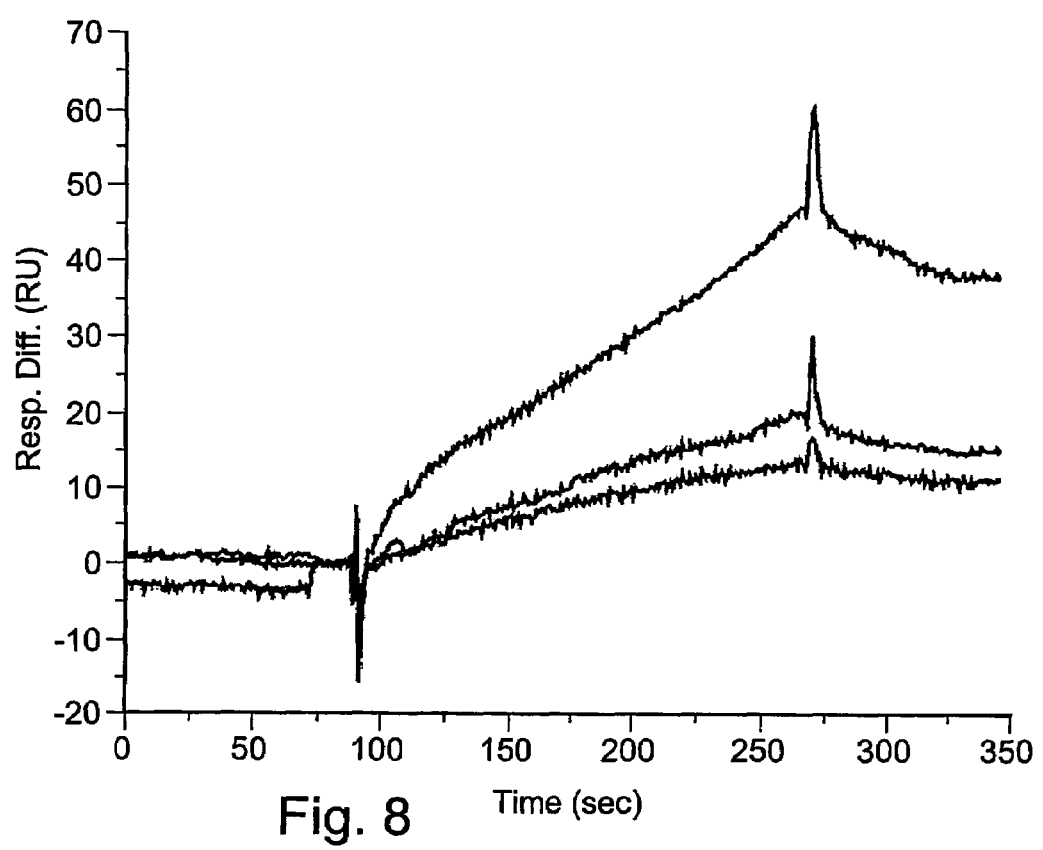

FIG. 8 is a surface plasmon resonance (SPR) analysis illustrating binding of GST-YoeB fusion polypeptide to the $YefM_{11-23}$ peptide which contains the YefM binding determinant. SPR sensorgrams show the change in binding response (in RU) upon injection of 12.5, 25 and 50 nM of GST-YoeB in 50 mM Tris-HCl (pH 7.2) running buffer over the $YefM_{11-23}$ peptide.

Figure 9A:
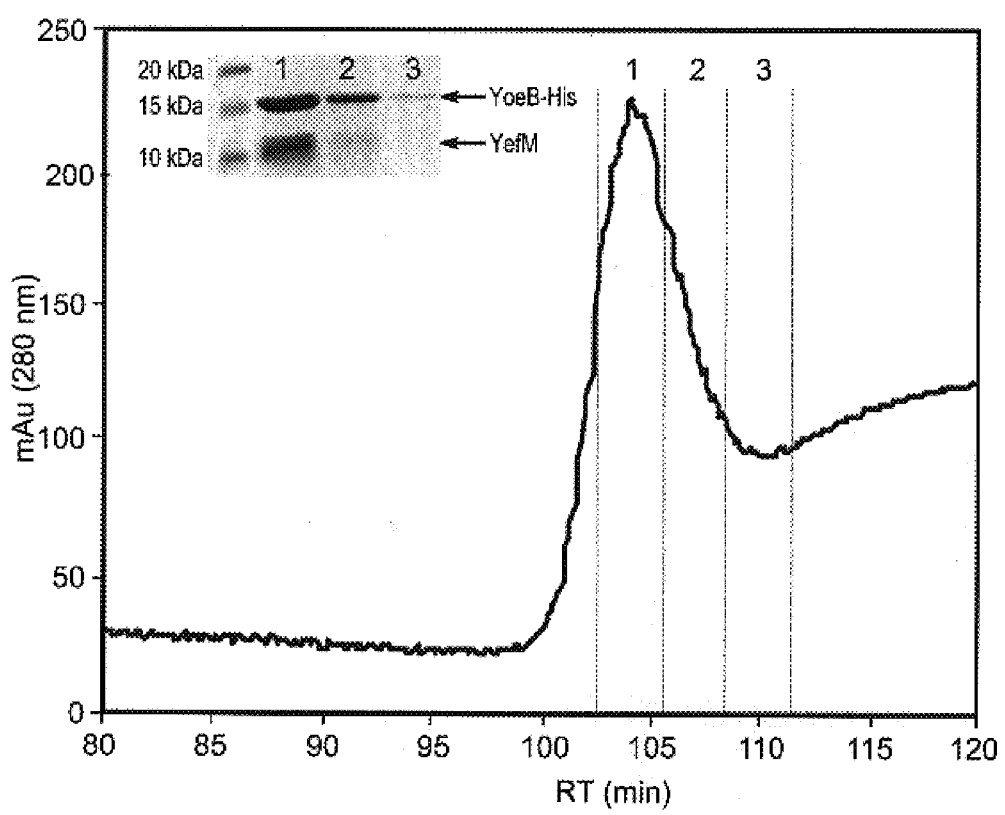
Figure 9B:
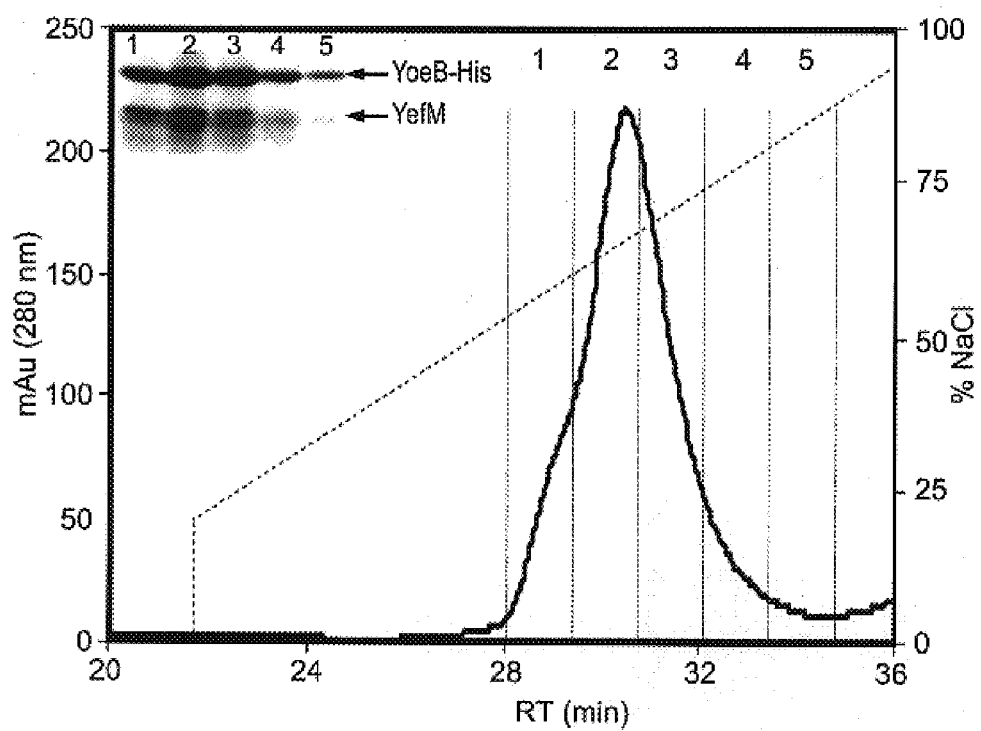
Figure 9C:
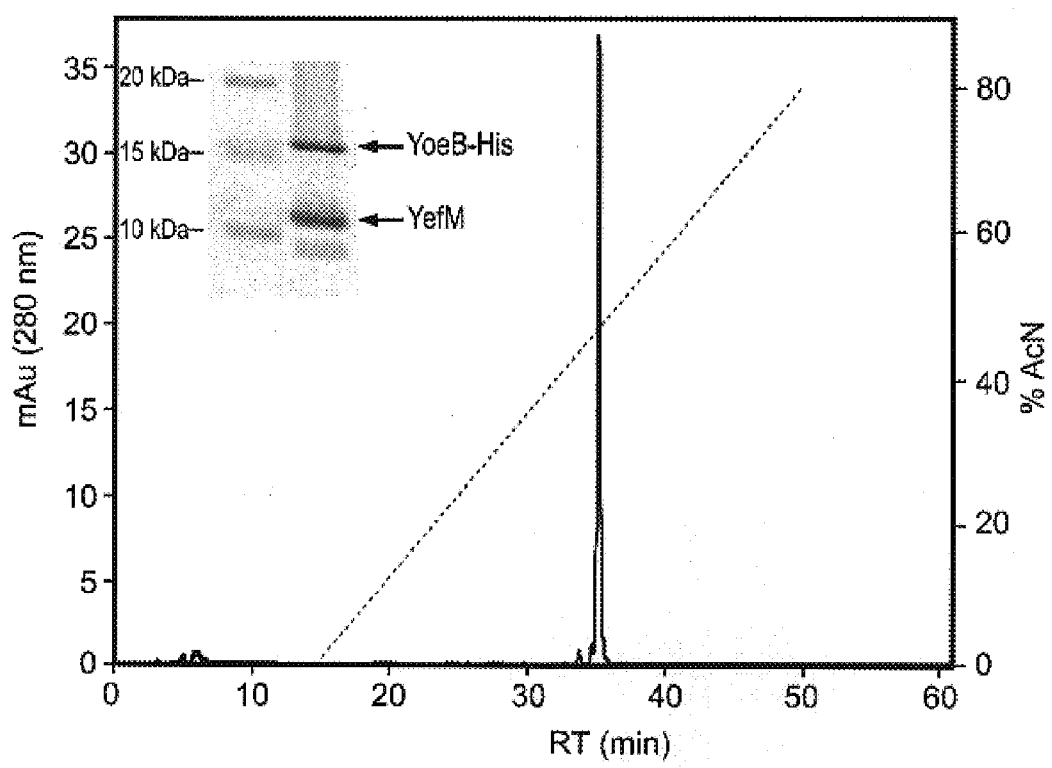

FIGS. 9A-C illustrate chromatography analyses indicating a tight binding between YoeB-His and YefM. FIG. 9A shows a co-elution of YefM and YoeB-His in a nickel affinity column chromatography. FIG. 9B shows a co-elution of YefM and YoeB-His resulting from an anion-exchange column developed with NaCl gradient FIG. 9C shows a co-elution of YefM and YoeB-His resulting from a $C_{18}$ HPLC reverse-phase column developed with acetonitrile gradient.

Figure 10A:
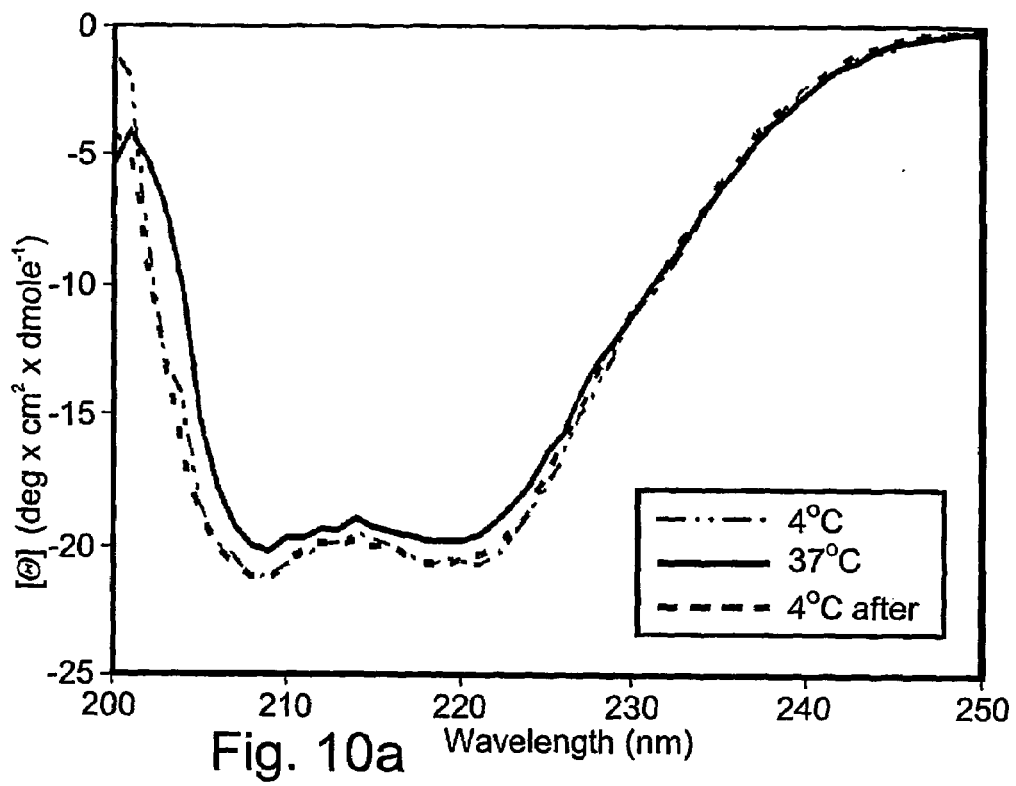
Figure 10B:
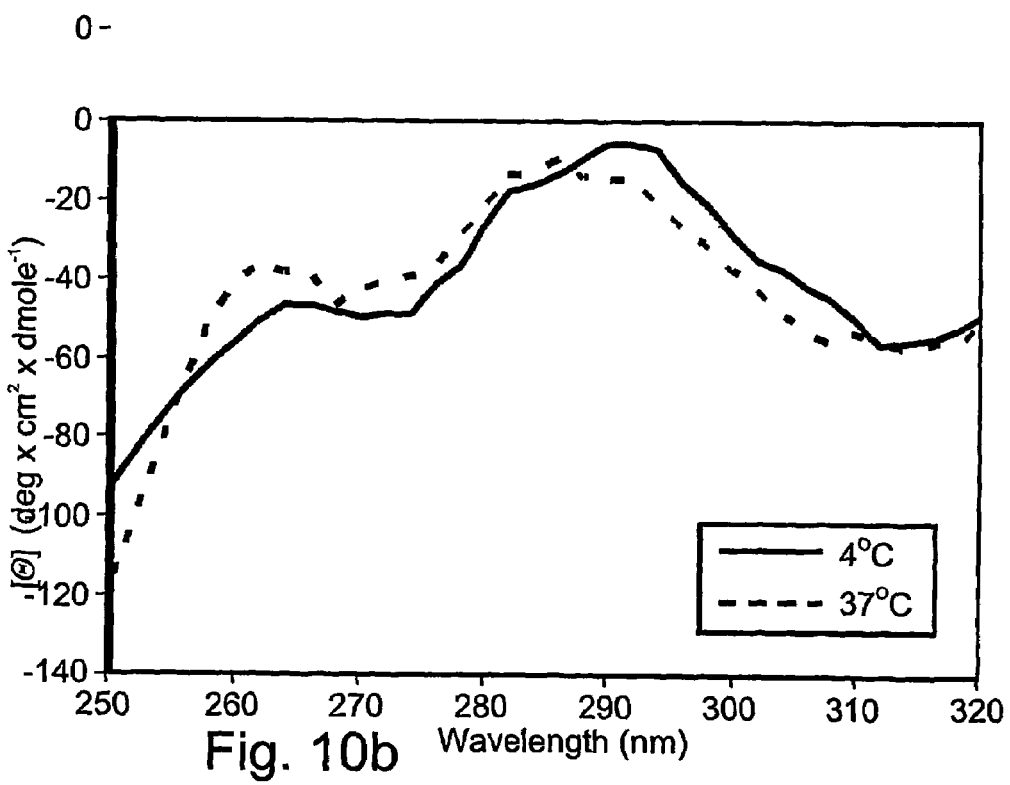
Figure 10C:
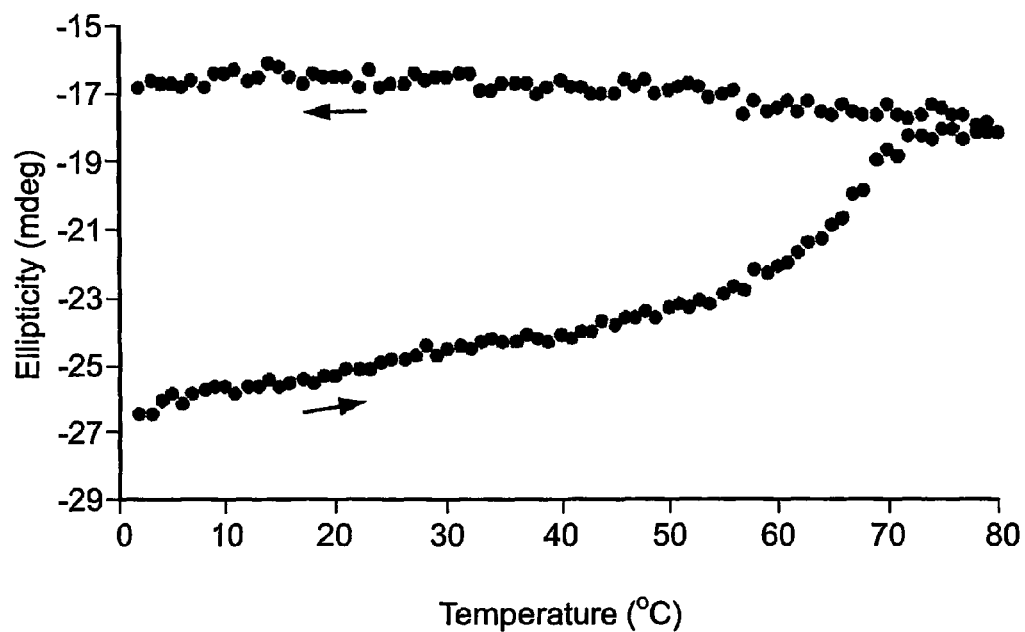

FIGS. 10A-C illustrate the structure and stability of the YoeB toxin FIG. 10A shows spectra of far UV circular-dichroism (CD) of 2.5 μM YoeB-His monitored at 4° C., 37° C. and 4° C. after 37° C., indicating a predominant α-helical structure. FIG. 10B shows spectra of Near-UV CD of 10 μM YoeB-His monitored at 4° C. and 37° C., indicating that no structural changes of the polypeptide occurred within that temperature range. FIG. 10C illustrates the thermal stability of YoeB-His at thermal melt and return range of 2⇌80° C. The thermal stability of YoeB-His was determined by monitoring CD ellipticity at 222 nm as a function of temperature.

Figure 11A:
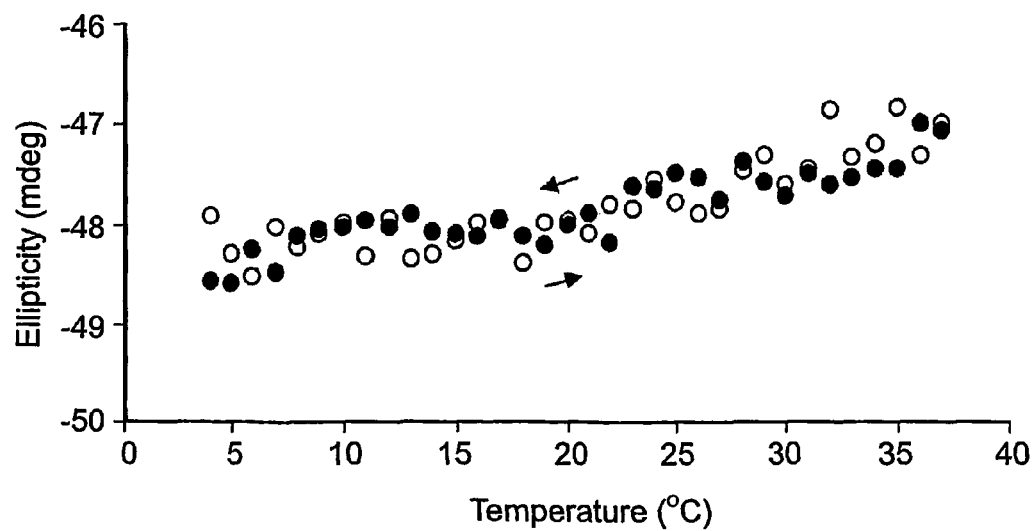
Figure 11B:
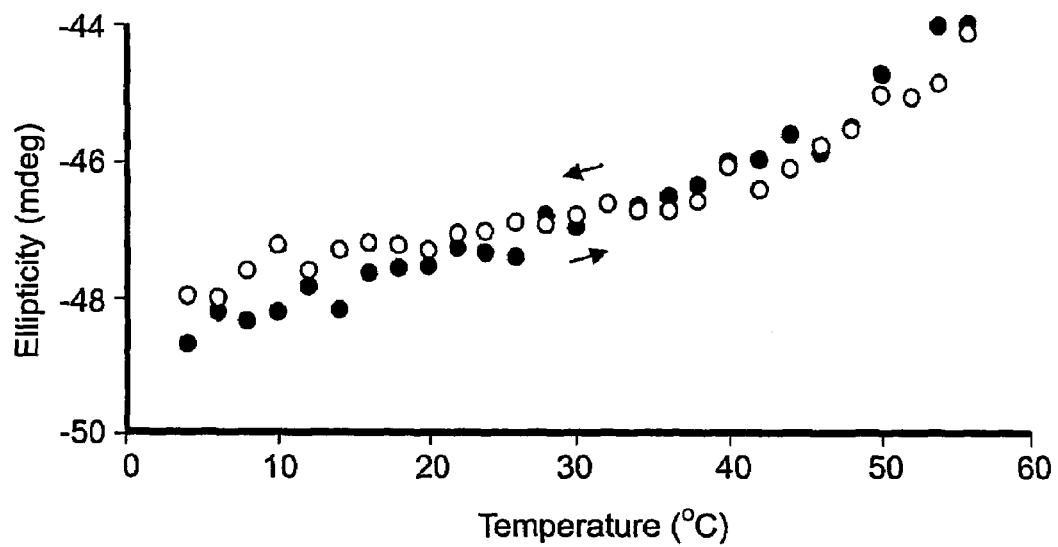
Figure 11C:
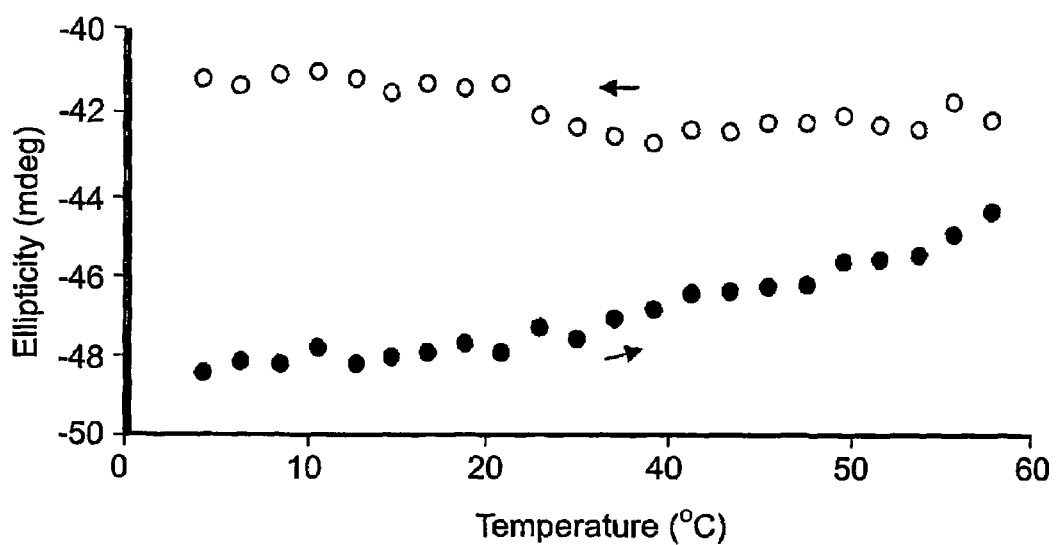

FIGS. 11A-C illustrate the thermal melting point of YoeB. FIG. 11A illustrates the CD ellipticity of YoeB-His as a function of temperature at 2⇌37° C. FIG. 11B illustrates the CD ellipticity of YoeB-His as a function of temperature at 2⇌56° C. FIG. 11C illustrates the CD ellipticity of YoeB-His as a function of temperature at 2⇌60° C., indicating that YoeB undergoes thermal denaturation at approximately 60° C.

DESCRIPTION OF THE PREFERRED EMBODIMENTS

The present invention is of methods of identifying agents capable of preventing or disrupting binding between antitoxin and toxin polypeptides in bacterial cells, and of pharmaceutical compositions which include such agents and their use for treating bacterial infections.

The principles and operation of the present invention may be better understood with reference to the drawings, examples and accompanying descriptions.

Before explaining at least one embodiment of the invention in detail, it is to be understood that the invention is not limited in its application to the details of construction and the arrangement of the components set forth in the following description or illustrated in the drawings and the examples. The invention is capable of other embodiments or of being practiced or carried out in various ways. Also, it is to be understood that the phraseology and terminology employed herein is for the purpose of description and should not be regarded as limiting.

As is discussed hereinabove, toxin-antitoxin polypeptide pairs are often present in bacterial cells. Although their function in such cells is not clear, it has been conclusively shown that antitoxin polypeptides bind to their cognate toxins to thereby neutralizing their cytotoxic activity in bacterial cells.

Using bioinformatic tools, the present inventors uncovered that homologues of the YoeB-YefM toxin-antitoxin pair exist in a wide range of bacteria, including several pathogenic bacteria Biochemical analysis has revealed that the YefM antitoxin is an unfolded polypeptide in its native state within bacterial cells. Further analysis using an isolated peptide derivative of YefM (YefM$_{11-23}$; set forth in SEQ ID NO: 7) identified the determinant sequence of YefM which is involved in YoeB toxin binding; surprisingly, an alteration of just one amino acid of the YefM$_{11-23}$ is sufficient to completely abolish this binding (see in Examples 1-6 hereinbelow). It was thus concluded that binding between the YoeB toxin and the YefM antitoxin polypeptides relies upon a highly specific recognition which can be readily prevented or disrupted.

Thus, according to one aspect of the present invention, there is provided a method of treating a bacterial infection in a subject, such as a mammal, preferably, a human.

The method is effected by preventing or disrupting binding between toxin and antitoxin polypeptides of toxin-antitoxin pairs produced in the bacteria responsible for infection.

The bacteria can be any bacteria which produces a toxin-antitoxin pair. Preferably, the bacteria are *Enterococcus faecium, Klebsiella pneumoniae, Mycobacterium tuberculosis, Salmonella typhimarium, Streptococcus pmeomoniae, Yersinia enterocolitica* and *E. coli.*

The toxin-antitoxin pair can be any pair of polypeptides encoded by a plasmid or chromosome of the bacteria responsible for the infection Specific examples of toxin-antitoxin pairs are provided in Table 1 and in the Examples section hereinbelow.

The phrase "preventing or disrupting" used herein refers to precluding binding between toxin and antitoxin polypeptides, or to disassociating a complex formed therefrom. As further described hereinbelow, such prevention or disruption can be effected by reducing expression of the antitoxin, or by reducing the antitoxin-toxin binding capacity.

Preventing or disrupting binding of a toxin-antitoxin pair can be effected using any one of several approaches.

In one approach, disrupting binding of a toxin-antitoxin pair is effected by providing to the subject an agent which specifically binds to the antitoxin, or, preferably, to the antitoxin binding determinant.

The binding determinant sequence of the antitoxin can be identified using techniques well known in the art including, but not limited to, peptide array analysis and surface plasmon-resonance analysis. Example 6 illustrates the isolation of a peptide derivative of the YefM antitoxin which includes the YefM antitoxin binding determinant (set forth in SEQ ID NO: 7). It will be appreciated that such characterization of the antitoxin binding determinant enables identification or design of a compound capable of preventing or disrupting the binding between toxin and antitoxin polypeptides. For example, using this determinant sequence, one of ordinary skill in the art can screen compound libraries for compounds which are capable of specifically binding this determinant and thus capable of preventing toxin-antitoxin binding.

An agent which specifically binds to the antitoxin binding determinant can be, for example, a peptide, a polynucleotide, a carbohydrate, a small organic molecule, or a non-biological compound.

The phrase "non-biological compound" used herein refers to an organic or an inorganic compound which is not naturally present in living organisms.

A peptide which specifically binds to the antitoxin binding determinant itself can be a toxin derivative which includes the toxin binding determinant sequence (the portion of the toxin molecule which participates the antitoxin-toxin binding). In cases where the antitoxin binding determinant is isolated, the toxin, binding determinant sequence can be readily identified using, for example, the peptide array analysis procedure described in Example 6 (by using toxin derivative peptides to form the array and a labeled antitoxin derivative as a probe).

Alternatively, a peptide, a polynucleotide, a carbohydrate, a small organic molecule, or a non-biological compound which specifically binds to the antitoxin binding determinant can be identified by using standard rational drug design methods or high throughput screening of combinatorial libraries, as described hereinbelow.

Disrupting binding between members of a toxin-antitoxin pair may also be effected by providing to the subject an agent (e.g., peptide) which specifically binds the toxin in a manner which interrupts toxin-antitoxin binding while at the same time does not substantially affect toxin activity. Toxin sequence regions (toxin binding determinants) which can be targeted by such an agent and agents which specifically bind thereto can be identified using methodology similar to that described above with respect to identifying antitoxin binding determinant sequences and agents which specifically bind thereto.

The agent identified capable of binding to the antitoxin or toxin binding determinant of infectious bacteria can be administered to the subject in need orally, intravenously, intraperitoneally, intramuscularly, subcutaneously, intracavity, or transdermally. A peptide or polynucleotide agent is preferably administered encapsulated in a suitable carrier, such as a liposome. Suitable encapsulated carriers may be prepared using methods such as described, for example, in U.S. Pat. Nos. 6,610,478, 6,309,669, 5,013,556 and 4,925,673 and by Clarenc et al. Anti-Cancer Drug Design, 8:81-94, 1993; Felgner, Advanced Drug Delivery Reviews, 5:163-187, 1990; and Wang et al., Biochem. 28:9508-9514, 1989.

Delivery of a polynucleotide agent to target infecting bacteria may also be effected by utilizing a recombinant nonlytic phage, such as M13 (Westwater et al., Antimicrobial Agents and Chemotherapy 47: 1301-1307, 2003).

Delivery of carbohydrates, small organic molecules, or non-biological compounds to target infecting bacteria in the subject may be effected using methods well known in the art such as described, for example, by Johnson et al., eds. (Drug Delivery Systems, Chichester, England: Ellis Horwood Ltd., 1987). Additional methods of formulating and administrating pharmaceutical compositions are described hereinbelow.

Another agent which can be used to specifically inhibit toxin-antitoxin binding is an antibody or an antibody fragment.

Preferably, the antibody or antibody fragment specifically binds at least one epitope of the antitoxin binding determinant. As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

The phrase "antibody or an antibody fragment" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) F(ab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (see for example, Harlow and Lane, Antibodies: A Laboratory Manual, Cold Spring Harbor Laboratory, New York, 1988).

Antibody fragments according to the present invention can be prepared by proteolytic hydrolysis of the antibody or by expression in $E.$ $coli$ or mammalian cells (e.g. Chinese hamster ovary cell culture or other protein expression systems) of DNA encoding the fragment Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, in U.S. Pat. Nos. 4,036,945 and 4,331,647, and references contained therein, which patents are hereby incorporated by reference in their entirety. See also Porter, R. R. (Biochem. J. 73: 119-126, 1959). Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. (Proc. Natl Acad. Sci. USA 69:2659-2662, 1972). Alternatively, the variable chains can be linked by an intermolecular disulfide bond or cross-linked by chemicals such as glutaraldehyde.

Preferably, the Fv fragments comprise VH and VL chains connected by a peptide linker. These single-chain antigen binding proteins (scFv) are prepared by constructing a structural gene comprising DNA sequences encoding the VH and VL domains connected by an oligonucleotide. The structural gene is inserted into an expression vector, which is subsequently introduced into a host cell such as $E.$ $coli.$ The recombinant host cells synthesize a single polypeptide chain with a linker peptide bridging the two V domains. Methods for producing scFv are described, for example, by Whitlow and Filpula (Methods 2: 97-105, 1991), Bird et al. (Science 242: 423-426, 1988), Pack et al. (Bio/Technology 11:1271-1277, 1993) and in U.S. Pat. No. 4,946,778.

Another form of an antibody fragment is a peptide coding for a single complementarity-determining region (CDR). CDR peptides ("minimal recognition units") can be obtained by constructing genes encoding the CDR of an antibody of interest Such genes are prepared, for example, by using the polymerase chain reaction to synthesize the variable region from RNA of antibody-producing cells. See, for example, Larrick and Fry (Methods, 2: 106-110, 1991).

Humanized forms of non-human (e.g., murine) antibodies are chimeric molecules of immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region Fc), typically that of a human immunoglobulin (Jones et al., Nature, 321: 522-525, 1986; Riechmann et al., Nature, 332:323-329, 1988; and Presta, Curr. Op. Struct. Biol., 2:593-596, 1992).

Methods for humanizing non-human antibodies or antibody fragments are well known in the art Generally, a humanized antibody has one or more amino acid residues introduced into it from a source which is non-human. These non-human amino acid residues are often referred to as import residues, which are typically taken from an import variable domain. Humanization can be essentially performed following the method of Jones et al. (Nature, 321:522-525, 1986), Riechmann et al. (Nature 332:323-327, 1985), and Verhoeyen et al. (Science, 239:1534-1536, 1988), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies or antibody fragments can also be produced using various techniques known in the art, including phage display libraries (Hoogenboom and Winter, J. Mol. Biol., 227:381, 1991; Marks et al., J. Mol. Biol., 222:581, 1991). The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern Rev. Immunol. 13, 65-93 (1995).

The antibody or antibody fragment of the present invention can be delivered to the target infecting bacteria in the subject using methods known in the art. Preferably, the antibody or antibody fragment is administered contained in a microparticle or microencapsulated carrier such as described, for example, in U.S. Pat. Nos. 6,610,478, 6,309,669, 5,013,556 and 4,925,673 and by Clarenc et al. Anti-Cancer Drug Design, 8:81-94, 1993; Felgner, Advanced Drug Delivery Reviews, 5:163-187, 1990; and Wang et al., Biochem. 28:9508-9514, 1989.

Preventing or disrupting binding of a toxin-antitoxin pair may also be effected by providing to the subject an antisense polynucleotide capable of specifically hybridizing with an mRNA transcript encoding the antitoxin.

Design of antisense molecules which can be used to efficiently hybridize with an mRNA transcript encoding the antitoxin must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 93540 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Several clinical trials have demonstrated safety, feasibility and activity of antisense oligonucleotides. For example, antisense oligonucleotides suitable for the treatment of cancer have been successfully used [Holmund et al., Curr Opin Mol Ther 1:372-85 (1999)], while treatment of hematological malignancies via antisense oligonucleotides targeting c-myb gene, p53 and Bcl-2 had entered clinical trials and had been shown to be tolerated by patients [Gerwitz Curr Opin Mol Ther 1:297-306 (1999)].

An example of using antisense molecules to treat bacterial infection is described in U.S. Pat. No. 6,677,153. Accordingly, oligomers antisense to bacterial 16S or 23S rRNA are capable of selectively modulating the biological activity thereof and thus can be used as antibacterial agents.

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation. A suitable antisense sequence according to the teaching of the present invention can be, for example, the antisense to YefM antitoxin set forth in SEQ ID NO: 126.

Preventing or disrupting binding of a toxin-antitoxin pair may also be effected by providing a small interfering RNA (siRNA) molecule which specifically cleaves the antitoxin transcripts.

RNA interference is a two step process. The first step, which is termed as the initiation step, input dsRNA is digested into 21-23 nucleotide (nt) small interfering RNAs (siRNA), probably by the action of Dicer, a member of the RNase III family of dsRNA-specific ribonucleases, which processes (cleaves) dsRNA (introduced directly or via a transgene or a virus) in an ATP-dependent manner. Successive cleavage events degrade the RNA to 19-21 bp duplexes (siRNA), each with 2-nucleotide 3' overhangs [Hutvagner and Zamore Curr. Opin Genetics and Development 12:225-232 (2002); and Bernstein Nature 409:363-366 (2001)].

In the effector step, the siRNA duplexes bind to a nuclease complex to from the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr. Opin. Genetics and Development 12:225-232 (2002); Hammond et al. (2001) Nat. Rev. Gem 2:110-119 (2001); and Sharp Genes. Dev. 15:485-90 (2001)]. Although the mechanism of cleavage is still to be elucidated, research indicates that each RISC contains a single siRNA and an RNase [Hutvagner and Zamore Curr. Opin. Genetics and Development 12:225-232 (2002)].

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC [Hammond et al. Nat Rev. Gen. 2:110-119 (2001), Sharp Genes. Dev. 15:485-90 (2001); Hutvagner and Zamore Curr. Opin. Genetics and Development 12:225-232 (2002)]. For more information on RNAi see the following reviews Tuschl ChemBiochem. 2:239-245 (2001); Cullen Nat. Immunol. 3:597-599 (2002); and Brantl Biochem. Biophys. Act. 1575: 15-25 (2002).

Synthesis of RNAi molecules suitable for use with the present invention can be effected as follows. First, the target antitoxin mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www.ambion.com/techlib/tn/91/912.html).

Second, potential target sites are compared to an appropriate genomic database (e.g., human, mouse, rat etc.) using any sequence alignment software, such as the BLAST software available from the NCBI server (www.ncbi.nlm.nih.gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene. Suitable siRNA molecules according to the teaching of the preset invention include, for example, the siRNA to the YefM antitoxin set forth in SEQ ID NOs: 127-128.

Preventing or disrupting binding of a toxin-antitoxin pair may also be effected by providing a DNAzyme molecule capable of specifically cleaving an mRNA transcript or DNA sequence of the antitoxin. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each This type of DNAzyme can effectively cleave its substrate RNA at purine:pyrimidine junctions (Santoro, S. W. & Joyce, G. F. Proc. Natl, Acad Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al., 20002, Abstract 409, Ann Meeting Am Soc Gen Ther www.asgt.org. In another application, DNAzymes complementary to ber-ab1 oncogenes were successful in inhibiting the oncogenes expression in leukemia cells, and lessening relapse rates in autologous bone marrow transplant in cases of CML and ALL.

Preventing or disrupting binding of a toxin-antitoxin pair may also be effected by providing a ribozyme which specifically cleaves transcripts encoding the antitoxin.

Ribozymes are being increasingly used for the sequence-specific inhibition of gene expression by the cleavage of mRNAs encoding polypeptides of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms has demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

Essentially, binding of any toxin-antitoxin pair of any bacterium can be prevented or disrupted using the above described agents and methodology. Table 1 below provides examples of several toxin-antitoxin pairs which can be targeted by the present invention.

TABLE 1

Target bacterial toxin-antitoxin pairs

| Bacterial species or strain * | Antitoxin | | Toxin | |
|---|---|---|---|---|
| | Amino-acid SEQ ID NO | Polynucleotide SEQ ID NO | Amino-acid SEQ ID NO | Polynucleotide SEQ ID NO |
| *Actinobacillus actinomycetemcomitans* | 68 | 10 | 69 | 11 |
| *Agrobacterium tumefaciens* | 70 | 12 | 71 | 13 |
| *Burkholderia cepacia* | 72 | 14 | 73 | 15 |
| *Coxiella burnetii* | 74 | 16 | 75 | 17 |
| *Escherichia coli* (YefM/YoeB) | 76 | 18 | 77 | 19 |
| Enterococcus facecium pRUM plasmid | 78 | 20 | 79 | 21 |
| *Francisella tularensis* pFNL10 plasmid (Phd) | 80 | 22 | 81 | 23 |
| Klebsiella pneumoniae | 82 | 24 | 83 | 25 |
| *Mycobacterium bovis* | 84 | 26 | 85 | 27 |
| Mycobacterium tuberculosis | 86 | 28 | 87 | 29 |
| *Neisseria europea* A | 88 | 30 | 89 | 31 |
| *Neisseria europea* B | 90 | 32 | 91 | 33 |
| *Neisseria europea* C | 92 | 34 | 93 | 35 |
| *Nostoc* sp. PCC 7120 | 94 | 36 | 95 | 37 |
| *Pseudomonas fluorescence* | 96 | 38 | 97 | 39 |
| *Pseudomonas putida* | 98 | 40 | 99 | 41 |
| *Pseudomonas syringae* | 100 | 42 | 101 | 43 |
| *Rickettsia conorii* | 102 | 44 | 103 | 45 |
| Salmonella typhimarium | 104 | 46 | 105 | 47 |
| Streptococcus aureus | 106 | 48 | 107 | 49 |
| *Streptococcus pneumoniae* | 108 | 50 | 109 | 51 |
| *Streptomyces coelicolor* | 110 | 52 | 111 | 53 |
| *Streptomyces viridochromogenes* | 112 | 54 | 113 | 55 |
| *Synechocystis* sp. PCC 7942 | 114 | 56 | 115 | 57 |
| *Synechocystis* sp. PCC 6803 A | 116 | 58 | 117 | 59 |
| *Synechocystis* sp. PCC 6803 B | 118 | 60 | 119 | 61 |
| *Tiobacillus ferroxidant* | 120 | 62 | 121 | 63 |
| Yersinia enterocolitica A | 122 | 64 | 123 | 65 |
| Yersinia enterocolitica B | 124 | 66 | 125 | 67 |

* species which appear in bold are major human pathogens

As is mentioned hereinabove, an agent which specifically binds to the antitoxin binding determinant, such as a peptide or a non-biological compound can be identified using rational drug design methods, following guidance such as described, for example, by Halperin et al., Proteins 47: 409-43, 2002; Gohlke and Klebe Curr Opin Struct Biol. 11: 231-235, 2001; Zeng J., Comb Chem High Throughput Screen. 3: 355-62, 2000; and RACHEL: Theory of drug design, http://www.newdrugdesign.com/Rachel_Theory.htm#Software). 3D chemical structure databases can be screened by using a suitable software such as, for example, ISIS (MDL Information Systems, San Leandro, http://www.molinfo.com), MACCS-3D (Martin, Y. C., J. Med. Chem. 35, 2145-2154, 1992), The Cambridge Structural Database (CSD; http://www.ccdc.cam.ac.uk/prods/csd/csd.html), Fine Chemical Database (reviewed in Rusinko A., 1993. Chem Des Auto. News 8, 44-47), and the NCBI's Molecular Modeling DataBase: MMDB; http://www.ncbi.nlm.nih.gov/Structure/MMDB/mmdb.shtml.

Alternatively, an agent which specifically binds to the antitoxin binding determinant (herein refers to as the "target sequence"), such as a peptide, a polynucleotide, a carbohydrate, or a non-biological compound can be identified by high throughput screening of combinatorial libraries.

The term "library" used herein refers to a collection of chemical or biological entities which can be screened simultaneously for a property of interest.

The phrase "combinatorial library" used herein refers to a library in which the individual members are either systematic or random combinations of a limited set of basic elements, the properties of each member being dependent on the choice and location of the elements incorporated into it.

A peptide library may be prepared by either biological or non-biological synthesis methods. In a biological synthesis method, a gene encoding the peptides of interest is expressed in a host cell such that the peptides are displayed either on the surface of the cell or on the outer coat of phage produced by the cell. For example, a phage libraries can be constructed according to the protocols (Construction of Random Peptide Libraries in Bacteriophage M13 in Phage Display of Peptides and Proteins: A Laboratory Manual. Edited by B. Kay, J. Winter and J. McCafferty. Academic Press 1996).

In order to achieve diversity, the gene must be randomized at those codons corresponding to variable residues of the peptide. It thus is not a single DNA, but rather a DNA mixture, which is introduced into the host cell culture, so that each cell has the potential, depending on which DNA it receives, of expressing any of the many possible peptide sequences of the library. The gene may be randomized by using a mixture of nucleotides rather than a pure nucleotide during appropriate synthetic cycles. The synthesis cycles may add one base at a time, or an entire codon. Examples of suitable procedures for constructing libraries of peptides generated by gene expression are described in Marks et al., J Mol Biol, 222:581-597, 1991; Lam et al., Nature, 354:82-84, 1991; Colas et al., Nature, 380:548-550, 1996; Lu, Bio/Technology, 13:366-372, 1990; and Smith, Science, 228:1315-1317, 1985.

The peptide library may also be prepared nonbiologically by stepwise addition of amino acids. During the cycles which incorporate variable residues, the activated amino acid is chosen randomly from an amino acid mixture. Preferably, the synthesis is carried out on a solid surface, such as a pin or bead (Geyesen et al., Proc Natl Acad Sci USA 81: 3998-4002, 1984), or bead (Lam et al., Nature 354: 82-84, 1991).

The peptide library may be attached to a polysome using a procedure such as described, for example, in U.S. Pat. Nos. 5,643,768 and 5,658,754; Gersuk, et al., Biochem. Biophys. Res. Comm. 232:578, 1997; and Mattheakis et al., Proc. Nat. Acad. Sci. USA, 91:9022-9026, 1994.

If the peptide library is on a solid phase, then preferably the target sequence is tagged. Suitable tags includes, but not limited to, enzymes such as galactosidase, luciferase, orglutathione-S-transferase (GST) and green fluorescent protein (GFP). Other tags can be incorporated via recombinant techniques include substrate sites for enzymes such as protein kinase A which allows for the rapid and efficient labeling of the target sequence with $^{32}P$. Less desirable, but still feasible, is the radio labeling of the recombinant protein, e.g., in vivo with $^{14}C$ or $^{3}H$ labeled amino acids or in vitro with $^{125}I$.

If the peptide library is in solution, the target sequence may be immobilized on chromatographic media either directly [e.g., by using AFFIGEL matrix (BioRad)], or indirectly. In indirect immobilization, the target sequence is noncovalently conjugated to the support by using an affinity reagent. For example, histidine-tagged target sequence may be immobilized on QIAGEN nickel binding resin, or a GST-tagged target sequence may be immobilized on glutathione SEPHAROSE chromatography matrix (Pharmacia). Subsequently, the immobilized target sequence is used to separate out peptides with desired activity by using methods such as described, for example, by Cantley et al. Trends Biochem. Sci. 20: 470-475, 1995; and Zhou and Cantley, Methods Enzymol 254: 523-535, 1995; Zhou and Cantley, Cell 72: 767-778, 1993.

In screening phage libraries, the target sequence is preferably immobilized on a solid support and screened using a procedure such as described, for example, by Devlin et al. (Science 249: 404-406, 1990) and Scott and Smith (Gene 128: 59-65, 1993).

Additionally, or alternatively to peptides, the agent which specifically binds to the target sequence can be a polynucleotide (aptamer). Target sequence-binding aptamers can be isolated using screening methods such as described, for example, in U.S. Pat. Nos. 5,270,163; 5,475,096; 5,567,588; 5,595,877; 5,637,459; 5,683,867; and 5,705,337 and by Colas et al. (Nature 380: 548-550, 1996) and Ellington and Szobtak (Nature 246: 818, 1990). For example, the starting libraries for a DNA library may be defined sequences on each end of 10 to 30 bases flaking a random core of 10 to 100 bases. Primers complementary to the defined sequences on each end are used to amplify the library and one would have a tag (such as biotin). Following amplification, the double stranded DNA is bound to a matrix (streptavidin agarose) and denatured to release ssDNA. To isolate the ligand, the target sequence is incubated with a starting library of single stranded DNA (ssDNA) and the aptamers are allowed to bind. Target-sequence and aptamer complexes are then bound onto nitrocellulose or nylon membranes and the unbound ssDNA molecules are discarded. The aptamers bound onto the target sequence are then eluted by one of several methods well known in the art (e.g., pH shock, phenol extraction, SDS treatment or heat), precipitated with ethanol and then preferably amplified by PCR to synthesize a new pool for an additional round of selection.

This process is preferably repeated 1 to 20 times. The number of repetitions is determined by monitoring the enrichment for binders after each round or after every other round of selection. This could be accomplished in several ways. The most often used approach is to radioactively label a small percentage of the library and monitor the fraction of the library retained on the filter after each round. An alternative method is to use a primer in the amplification reaction which would allow the aptamer to be detected. Two examples of this are rhodamine and digoxigenin. Rhodamine is detected directly by fluorescence and DIG is detected by an antibody which is either directly or indirectly coupled to an enzymatic or fluorescence readout. Using a labeled primer would allow the detection of aptamer binding to target in a standard ELISA format in which the target sequence is immobilized in the well of a plate, the aptamer is added and allowed to bind and is then detected using one of the methods mentioned hereinabove. Once a sufficient level of enrichment has been attained, the final pool is amplified and cloned into a plasmid which allows for the rapid sequencing of the inserts.

Additionally, or alternatively to peptides and polynucleotides, the agent which specifically binds to the target sequence can be a carbohydrate or a small organic molecule. Libraries of carbohydrates and small organic molecules may be prepared and screened for target sequence binding activity using methods such as described, for example, by Eichler et al. (Med Res Rev. 15:481-96, 1995).

Additionally, or alternatively the agent which specifically binds to the target sequence can be a non-biological compound. Libraries of non-biological compounds may be generated and screened for target sequence binding activity using methods such as described in details in U.S. Pat. No. 6,617, 114.

Agents identified capable of preventing or disrupting binding of toxin-antitoxin pairs in bacterial cells can be evaluated in vitro for their capacity to induce death in bacteria expressing the toxin-antitoxin pairs.

Thus, according to another aspect of the present invention, there is provided a method of identifying a molecule capable of inducing death of a bacterial cell. The method includes exposing toxin and antitoxin polypeptides of a toxin-antitoxin pair produced by the bacterial cell to a plurality of molecules followed by identifying a molecule which is capable of preventing or disrupting binding between the antitoxin and the toxin polypeptides, thereby identifying the molecule capable of inducing death of the bacterial cell.

Preferably, exposing is effected by administering the plurality of molecules to bacteria expressing the toxin and antitoxin polypeptides, followed by determining growth of the bacteria exposed to the plurality of molecules and selecting at least one of the bacteria exhibiting a reduction in growth as compared with similar bacteria not exposed to the plurality of molecules. Preferably, the bacteria are genetically modified and cultured to overexpress the toxin-antitoxin pair, using a procedure such as described, for example, in Example 3 of the Examples section hereinbelow.

An agent identified capable of preventing or disrupting binding of toxin-antitoxin pairs in bacteria, can be used in therapy per se or as part (active ingredient) of a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a bone tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. One route of administration which is suited for the pharmaceutical compositions of the present invention is sub-periosteal injection, as described in U.S. Pat. No. 6,525,030 to Erikkson. For transmucosal administration, penetrants appropriate to the barrier to be permeated are used in the formulation Such penetrants are generally known in the art.

For oral administration, the pharmaceutical composition can be formulated readily by combining the active compounds with pharmaceutically acceptable carriers well known in the art Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP) if desired, disintegrating agents may be added, such as cross-linked polyvinyl pyrrolidone, agar, or alginic acid or a salt thereof such as sodium alginate. As used herein, the term "oral administration" includes administration of the pharmaceutical compound to any oral surface, including the tongue, gums, palate, or other buccal surfaces. Addition methods of oral administration include provision of the pharmaceutical composition in a mist, spray or suspension compatible with tissues of the oral surface.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (e.g. antisense oligonucleotide) effective to prevent, alleviate or ameliorate symptoms of a disorder (e.g., mammary tumor progression) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in an animal model, such as the murine Neu model [Muller et al., Cell 54, 105-115 (1988)], to achieve a desired concentration or titer.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to levels of the active ingredient which are sufficient to, for example, retard tumor progression in the case of blastic metastases (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, presented in a pack or dispenser device, such as an FDA approved kit, which may contain one or more unit dosage forms containing the active ingredient. The pack may, for example, comprise metal or plastic foil, such as a blister pack The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

Hence, the present invention provides methods of identifying novel antibacterial agents capable of preventing or disrupting antitoxin-toxin binding in bacterial cells, pharmaceutical compositions comprising these agents and their use in treating bacterial infections.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology. A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

Identification of YefM and YoeB Homologue Genomic Sequences in Bacteria

Materials and Methods:

Genomic sequences related to the yefM and yoeB genes of E. coli (SEQ ID NO: 18 and 19, respectively) were identified by a pair-constrained analysis using TBLASTN and PSI-BLAST searches (20) of non-redundant microbial genomes database at NCBI (http://www.ncbi.nlm.nih.gov/BLAST/). Putative yefM and yoeB homologue sequences were obtained and examined for constituting a toxin-antitoxin gene-pair module in the chromosome. Low homology unpaired sequences were discarded and pairs of genomic sequences positioned at distance of less than 100 bp were regarded as putative toxin-antitoxin systems.

Results:

Genomic sequence pairs related to yefM and yoeB were identified in 29 bacterial strains representing 13 different genera and 25 different species (FIG. 1). It is thereby demonstrated that toxin-antitoxin systems are common and widespread among bacteria and that such systems can be identified by using bioinformatical tools such as a pair-constrained analysis of genomic sequence databases.

Example 2

Sequence Alignment of YefM and YoeB Polypeptide Homologues

Materials and Methods:

Multiple alignments of translated sequences of the YefM and YoeB homologues identified in Example 1 above, were produced by CLASTAL W (21) with default settings and edited using JALVIEW editor.

Results:

Alignments of the YoeB polypeptide homologues FIG. 2B) revealed a substantially higher level of homology than was observed within the YefM and Phd family of polypeptides FIG. 2A). The relatively high degree of conservation within the YoeB homologues is well consistent with a toxic activity that explicitly targets a specific cellular determinants and that requires a well-defined fold such as a key-lock or induced fit recognition. On the other hand, the relatively low degree of conservation of YefM and Phd homologues is consistent with a polypeptide missing a clear structural recognition and/or catalytic activity that otherwise requires a defined configuration. It should be appreciated that YefM and Phd polypeptides could be irregularly conjugated to a Doc-like or YoeB-like toxins, two families of toxins that could not be aligned and do not share any substantial homology. It is, however, consistent with a family of polypeptides which is essentially designed to be recognized as a damaged polypeptide and does not represent an interactive or catalytic scaffold.

Example 3

Characterizing YoeB and YefM Polypeptides as a Toxin-Antitoxin Pair

Materials and Methods:

Cloning YefM, YoeB and YefM-YoeB encoding sequences into pBAD-TOPO expression vector: The encoding sequences were produced by PCR using the chromosomal DNA of E. coli strain K-12/MC1061 as a template. The YefM encoding sequence was amplified with the primers set forth in SEQ ID NOs: 1-2. The YoeB encoding sequence was amplified with the primers set forth in SEQ ID NOs: 3-4. The YefM and YoeB pair encoding sequence was amplified using the primers of SEQ ID NOs: 1 and 4. The PCR products were inserted into the pBAD-TOPO vector to generate pBAD-yefM, pBAD-yoeB, and pBAD-yefMyoeB constructs using the pBAD-TOPO TA cloning kit (Invitrogen). The generated constructs were introduced to E. coli strain TOP10.

Growth rate analysis: E. coli TOP10 bacteria transformed with pBAD-yefM, pBAD-yoeB, and pBAD-yefMyoeB were cultured in LB broth supplemented with 100 µg/ml ampicillin (LB-Amp) and incubated at 37° C. overnight. Following incubation, cultures were diluted in fresh LB-Amp and their optical density was adjusted to approximately 0.01 ($A_{600}$). Each culture was then divided into two equal volumes. One volume was supplemented with 0.2% L-arabinose to induce expression of the target gene and the second volume was supplemented with 0.2% D-glucose to suppress expression. All cultures were incubated at 37° C. and 200 rpm for up to 9 hours. Cell density was estimated periodically by optical absorbance at 600 nm. The effect of target gene induction on bacterial growth during the logarithmic growth phase was determined as described above with the exception that cultures were divided and supplemented with 0.2% L-arabinose, or 0.2% D-glucose at the time they had reached optical density of approximately 0.45 ($A_{600}$).

Colony formation analysis: E. coli TOP10 bacteria harboring pBAD-yefM, pBAD-yoeB, or pBAD-yefMyoeB, were cultured in LB-Amp and incubated at 37° C. overnight Following incubation the cultures were diluted to an $A_{600}$ of 0.01 in a fresh LB-Amp and incubated at 37° C. until an absorbance of 0.5 at $A_{600}$ was reached. The cultures were then diluted in ten-fold dilutions steps and applied as 5 µl droplets on LB-Amp agar plates containing L-arabinose at a concentration gradient of 0.2%, 0.1%, 0.05%, 0.02%, 0.005% and 0.0005%. An LB-Amp agar plate containing 0.2% glucose was used as a negative control. All plates were incubated at 37° C. for at least 20 hours.

Results:

Growth of bacteria overexpressing YoeB or YefM alone was substantially reduced as compared with the control (FIG. 3B). On the other hand, growth of bacteria overexpressing both YefM and YoeB remained normal (FIG. 3C). Similar results were observed when the expression of YoeB and YefM was induced during the logarithmic growth phase of the bacteria (FIGS. 3D-F). In addition, an overexpression of either YeoB or YefM alone inhibited bacterial colony formation, while, on the other hand, colony formation was unaffected when both YoeB and YefM polypeptides were overexpressed (FIG. 3G).

These results clearly indicate that YoeB and YefM polypeptides behave as a toxin-antitoxin pair.

Example 4

Biophysical Characterization of YefM Antitoxin

Materials and Methods:
Cloning, expression and purification of YefM from *E. coli*: The DNA fragment containing yefM coding sequence flanked by primer-encoded BsrGI and HindIII sites, was produced by a polymerase chain reaction (PCR) using *E. coli* K-12 MC1061 strain chromosome as template and oligonucleotide primers set forth in SEQ ID NOs: 5 and 2. The PCR product was digested with BsrGI and HindIII enzymes (New England Biolabs), cloned into the BsrGI and HindIII restriction sites of a pET42a expression vector (Novagen) in fusion to glutathione s-transferase (GST) and transformed into *E. coli* BL21(DE3) pLysS (Novagen). Transformed bacteria were cultured in 2YT broth at 37° C. and 200 rpm to an optical density ($A_{600}$) of approximately 0.4. Polypeptide expression was induced by the addition of IPTG (2 mM). One hour following induction cells were harvested and re-suspended in a solution comprising phosphate buffer saline (pH 7.3), 140 mM NaCl, 2.7 mM KCl, 10 mM $Na_2HPO_4$, 1.8 mM $KH_2PO_4$), protease inhibitor cocktail as recommended (Sigma), and 0.5 mM PMSF. The suspended cells were lysed via three passages through a French-press cell (1400 psi) and the insoluble material was removed by centrifugation for 20 min at 20,000×g at 4° C., followed by filtration through a 0.45 µm membrane. The lysate supernatant was applied onto a 1 ml glutathione sepharose column (Amersham Pharmacia Biotech) pre-pre-equilibrated with PBS (pH 7.3). The YefM-GST fusion protein was eluted using 10 ml of a solution comprising 50 mM Tris-HCl (pH 8.0) and 10 mM glutathione. YefM was separated from GST by incubation at 37° C. in the presence factor Xa protease (Novagen; 16 units of protease per 1 mg YefM fusion). Following 14 hours incubation, the protease reaction was terminated by the addition of 1 mM PMSF.

Two different methods were applied for YefM purification. In one method, GST and linker polypeptide (~40 kDa) was separated from YefM (~11 kDa) using a Sepharose HR 10/30 (FPLC) gel filtration column (Amersham-Pharmacia Biotech) and a FPLC instrument (Pharmacia LBK). Polypeptides were eluted with PBS (pH 7.3), 0.8 ml/min, and a peak that included the ~11 kDa YefM polypeptides was collected after 13 min. Fractions containing the YefM polypeptide were completely purified using 1 µmol of immobilized glutathione agarose (Sigma) agitated for 16 hours at room temperature. At this point, the purity of YefM was greater than 95% (estimated by Coomassie staining of SDS-PAGE).

In another purification method, the YefM and GST mixture was divided into 0.5 ml aliquots, boiled for 10 minutes and then centrifuged at 14,000 rpm for 10 minutes. The supernatants, containing purified YefM, were collected and united.

The YefM concentration was estimated based on tyrosine absorbance in 0.1M KOH was used. Polypeptide concentrations were calculated using the extinction coefficients of 2391 $M^{-1}$ $cm^{-1}$ (293.2 nm in 0.1 M KOH) for single tyrosine.

The molecular mass of YefM was verified by matrix-assisted laser desorption ionization time-of-flight (MALDI-TOF) mass spectrometry using a voyager-DE STR Biospectrometry workstation (Applied Biosystems) and using α-Cyano-4-hydroxycinnamic acid as the matrix.

Circular Dichroism (CD): CD spectra were obtained by using an AVIV 202 spectrapolarimeter equipped with temperature-controlled sample holder and a 5 mm path length cuvette. Mean residual ellipticity, [θ], was calculated as, $$[\theta]=[100\times\theta\times m]/[c\times L]$$

where θ is the observed ellipticity, m is the mean residual weight, c is the concentration in mg/ml, and L is the path length in centimeters.

All experiments were performed in PBS (pH 7.3) at polypeptide concentration of 10 µM. For thermal denaturation experiments, samples were equilibrated at each temperature for 0.5 min and CD ellipticity at 222 nm and 217 nm was averaged for 1 min.

Fourier Transform Infrared Spectroscopy (FTIR): Spectra were recorded using a Nicolet Nexus 470 FT-IR spectrometer with a DTGS detector. A sample of 1 µg of lyophilized YefM, suspended in 30 µl PBS in $D_2O$ (pH 7.3), was dispensed on a $CaF_2$ plate. Spectrometer measurements were taken using a 4 $cm^{-1}$ resolution and 2,000 scans averaging and the transmittance minima values were determined by the OMNIC analysis program (Nicolet).

Amino acid composition and charge-hydrophobicity values analysis: The occurrence rate of each amino acid in the YefM family of polypeptides ($P_{Mi}$) was determined by averaging its 30 frequencies in 30 YefM homologue sequences. The general amino acid occurrence rates ($P_{Gi}$) were compiled by the Rockerfeller authors using the NCBI database (22). The relative differences between the occurrence rates of amino acids in YefM polypeptides and in general polypeptides was evaluated as ($P_{Mi}-P_{Gi}$)/$P_{Gi}$. The variances of these ratios were calculated as: Var($P_{Mi}$)/($P_{Gi}$)$^2$. The overall hydrophobicity and net charge values of YefM family of polypeptides were calculated and plotted according to Uversky et al. (3).

YefM stability analysis: Overnight culture of *E. coli* carrying the pBAD-yefM plasmid was grown at 37° C./200 rpm in LB broth to stationary phase ($OD_{600}$=1.4). YefM expression was then induced for 10 min with 0.2% L-arabinose and subsequently treated with 200 µg/ml rifampicin and 0.2% glucose to repress further expression from pBAD promoter. Aliquots of 2 ml were removed before and at 15 min intervals after repression, and the cellular YefM polypeptide was quantitatively analyzed by western blot Densitometer assessment of YefM was effected using Imagescanner (Amersham Biosciences) and the ImageMaster 1D prime (ver. 3.01) program (Amersham Biosciences).

Results:
A far UV circular dichroism (CD) spectra of the purified YefM polypeptide (in both purification methods) at increasing temperatures (25, 37 and 42° C.) is illustrated in FIG. 4A. The spectra indicate a typical random-coil pattern, according to Jenness et al. (25), with a minimum in the vicinity of 200 nm with only slight changes in spectra due to temperature increase. An FTIR spectrum of the purified YefM at room temperature is illustrated in FIG. 4B. The spectrum shows a transmittance minimum at 1643 $cm^{-1}$ which is indicative of a random-coil structure according to Haris and Chapman (26). Thermal denaturation curve further indicates a consistent predominant random-coil structure of YefM which is maintained at 2° C. to 80° C. range (FIG. 4C). The unfolded state of YefM is further supported by its extraordinary solubility during boiling (FIG. 4D).

In order to get insight into the structural stability of the YefM in its native state within cells, a short expression of YefM was effected followed by its full repression under stationary growth Analysis of YefM levels in *E. coli*, before and after repression at different intervals, revealed that native YefM has an in vivo half-life of approximately one hour (FIG. 7), which is characteristic to an antitoxin.

These results clearly indicate that YefM is an unfolded and unstable polypeptide in vivo.

Example 5

Biophysical Characterization of YoeB Toxin

Materials and Methods:

Cloning, expression and purification of YoeB from *E. coli*: The DNA fragment containing yefM-yoeB coding sequence was produced by a polymerase chain reaction (PCR) using *E. coli* K-12 MC1061 strain chromosome as template and oligonucleotide primers set forth in SEQ ID NOs: 5 and 132. The PCR product was cloned into the pTrcHis2 expression vector (Invitrogen) in fusion to myc-epitope and his-tag, to generate pTMB. The plasmid was transformed into *E. coli* TOP10 strain (Invitrogen). Transformed bacteria were cultured in 2YT broth at 37° C. and 200 rpm to an optical density ($A_{600}$) of approximately 0.4. Polypeptide expression was induced by the addition of IPTG (2 mM). Following one hour induction, cells were harvested and re-suspended in a Buffer A (phosphate buffer saline, pH 8.0; 50 mM $Na_2HPO_4$—NaOH; 0.3 M NaCl; and 0.5 mM PMSF). The suspended cells were lysed via three passages through a French-press cell (1400 psi) and the insoluble material was removed by centrifugation for 20 min at 20,000×g at 4° C., followed by filtration through a 0.45 µm membrane. The lysate supernatant was applied onto a Ni-CAM HC resin (Sigma) packed in a XG 16/20 FPLC column (Amersham Biosciences) pre-equilibrated with Buffer A. Following column wash, polypeptides were eluted with buffer A and 250 mM imidazole solution, in a single broad peak representing the purified YoeB-His (in a small number of fractions) or YoeB-His together with YefM (in most fractions). When eluted alone, YoeB-His purity was at least 90% as estimated by SDS-PAGE Coomasssie-blue staining.

Eluted YefM and YoeB-His complex was applied to HiPrep 16/10 Q XL column and, pre-equilibrated with Buffer B (20 mM Tris-HCl, pH 8.0). Elution was performed with developing NaCl gradient from 0.02 to 1 M in buffer B. The YefM: YoeB-His complex was eluted at approximately 650 mM NaCl. The complex was also separated using an analytic reverse-phase $C_{18}$ column (Vydac) with increasing gradient of 0 to 80% acetonitrile and 0.1% trifluoracetic acid. YefM and YoeB-His polypeptides were eluted in a single peak in approximate 50% acetonitrile. In all above cases, elution was monitored at $A_{280}$.

The identity of YefM and YoeB-His was verified using protein spots isolation from Coomassie blue stained gels and was accomplished by mass spectrometry, according to established protocols (Bandow, J. E., Becher, D., Buttner, K, Hochgrafe, F., Freiberg, C., Brotz, H. and Hecker, M. (2003) *Proteomics*. 3, 299-306). Briefly, protein spots were excised from stained gels and the gel pieces were treated trypsin solution (Pomega) for 16 h at 37° C. Peptides were extracted from gel onto a sample plate for MALDI-MS. Obtained peptides masses were determined in the positive ion reflector mode in a Voyager-DE STR mass spectrometer (Applied Biosystems). Peptide mass fingerprints were compared to databases using the MS-Fit program (http://prospector.ucsf.edu). To determine the concentrations of YoeB-His and YefM polypeptides, tyrosine and tryptophan absorbance measurements in 0.1 M KOH were used. YefM concentration was calculated using the extinction coefficient of 2381 $M^{-1}$ $cm^{-1}$ at 293.2 nm for single tyrosine (4 tyr). YoeB-His concentration was calculated using extinction coefficient at 280 nm of 1507 $M^{-1}$ $cm^{-1}$ for single tyrosine (6 tyr) and 5377 $M^{-1}$ $cm^{-1}$ for single tryptophan (4 trp). Circular Dichroism (CD) spectra were obtained as described in Example 4 hereinabove. For thermal denaturation experiments, the sample temperature was equilibrated for 30 sec at each temperature interval and the ellipticity at 222 nm was averaged for 1 min. All experiments were performed in PBS, pH 7.3.

Results:

The YoeB-His and YefM polypeptides co-eluted using nickel column chromatography (FIG. 9A), ion-exchange chromatography on a Q-sepharose column (FIG. 9B) and RP-HPLC chromatography using a $C_{18}$ analytical column (FIG. 9C), indicating a toxin-antitoxin complex.

The structure of purified YoeB-His toxin, as indicated from the far-UV circular dichroism (CD) spectrum (FIG. 10A), is consistent with a well-folded protein containing at least 50% α-helical secondary structure. The secondary structure content of the toxin remains nearly unchanged between 4-37° C. A near-UV CD analysis of YoeB-His also showed stability over this temperature range (FIG. 10B) indicating that the tertiary structure of the toxin remains virtually unchanged as well. In addition, the YoeB-His exhibits full structural reversibility within the 4-37° C. temperature range (FIG. 10A).

In order to determine the thermodynamic stability, YoeB-His underwent thermal denaturation between 2 and 80° C. monitored by CD ellipticity at 222 nm in neutral buffer. As can be seen in FIG. 10C, a sharp increase in ellipticity slope was observed during the melting phase at approximately 60° C. Cooling back from 80° C. to 2° C. could not bring to any observed renaturation, indicating that YoeB-His polypeptide could not regain its native conformation following such melt. In order to identify the melting point of the toxin, YoeB-His was partially melted and then cooled back repeatedly, each time raising the target temperature in about 5° C. increments. Conformational changes were monitored by measuring the CD ellipticity at 222 nm. The analysis shows structural reversibility of YoeB-His at a temperature ranging from 4 to 56° C. (FIGS. 11A-B). However, the YoeB-His polypeptide was unable to refold following melting at 60° C. (FIG. 11C), indicating that the polypeptide melting point ($T_M$) is approximately 60° C.

Example 6

Identification of YefM Recognition Determinants

Materials and Methods:

Cloning, expression, and purification of YefM from *E. coli*: performed as described in Example 4 above.

Cloning, expression, and purification of GST-YoeB from *E. coli*: DNA fragment containing the coding sequence of yoeB, flanked by primer-encoded EcoRI and HindIII sites, was produced by a polymerase chain reaction using *E. coli* K-12 MC1061 strain chromosome as template and oligonucleotide primers set forth in SEQ ID NOs:1 and 132. The PCR product was digested with EcoRI and HindIII enzymes (New England Biolabs), cloned into the EcoRI and HindIII restriction sites of the pET42a expression vector in fusion to GST, and transformed into *E. coli* BL21(DE3) pLysS. Bacteria were grown, expressed and lysed in the same manner described above for GST-YefM fusion protein. The supernatant was applied onto a 1 ml glutathione sepharose column (Amersham Pharmacia Biotech) pre-equilibrated with PBS (pH 7.3). The bound protein was eluted using 10 ml of 50 mM Tris-HCl (pH 8.0), 10 mM glutathione. Eluted fractions containing the GST-YoeB fusion protein were collected and quantitatively assessed by Coomassie staining of SDS-PAGE.

Peptide array analysis: Tridecamer peptides corresponding to consecutive overlapping sequences of the YefM polypeptide were arrayed on a cellulose membrane matrix and covalently bound to a Whatman 50 cellulose support (Whatman). Approximately 50 µg aliquots of soluble GST-YoeB fusion were examined for their selective peptide binding ability, on the basis of YefM-YoeB putative interaction.

For low stringency binding the cellulose membrane was briefly washed in 100% ethanol, washed three times with Tris-buffered saline (TBS; 50 mM Tris-HCl pH 7.5, 150 mM NaCl), then blocked for 4 hours using 5% (w/v) non-fat milk in TBS. The membrane was then washed three times in TBS+ 0.1% (v/v) tween 20 (TBS-T) and incubated with 10 ml GST-YoeB solution at 4° C. and slow shaking for 14 hours.

For high stringency binding the washing steps were extensive and multiple and the blocking solution washing step was reduced to a single brief wash.

Following incubation, the membrane was washed once in TBS-T then supplemented with 10 ml suspension comprising TBS, mouse anti-GST antibody and horseradish peroxidase conjugated goat anti-mouse antibody in the appropriate titers. Following 1 hour incubation at room temperature the membrane was briefly washed with TBS-T and TBS. Bound GST-YoeB proteins were detected through an enhanced chemiluminescence reaction following an exposure to a sensitive film.

Western blot analysis: Bacterial culture aliquots (2 ml) were centrifuged at 14,000 rpm for 5 min at 4° C. and re-suspended in 80 µl of double-distilled water. Sixty µl suspension aliquots were added to 20 µl aliquots of 4× sample buffer, and the remaining 20 µl aliquots were used to quantify the total polypeptide using the Coomassie plus protein assay reagent (Pierce). Aliquots containing equal total polypeptide amounts were loaded on a tris-tricine SDS 15% polyacrylamide slab gel. After electrophoresis, the proteins were electroblotted to PVDF membrane filters (Bio-Rad) and exposed to anti-YefM serum raised in rabbit. The membrane was then incubated with peroxidase-conjugated anti-rabbit antibodies and the presence of YefM was determined by an enhanced chemiluminescence reaction following by an exposure to a sensitive film.

Surface plasmon resonance analysis Binding affinities were evaluated by surface plasmon resonance (SPR) using BIAcore™2000 (BIAcore Inc., NJ). Approximately 30 resonance units of the peptide having the amino acid sequence set forth in SEQ ID NO: 7, denoting to the YefM antitoxin binding determinant sequence, was immobilized onto a research grade sensor chip CM5 using amine coupling kit (BIAcore) as described by the manufacturer. Suspensions of 12.5, 25, and 50 nM GST-YoeB fusion polypeptide in 50 mM Tris (pH 7.2) were passed over the chip surface at room temperature and a flow rate of 10 µl/min. The chip surface was regenerated with 10 mM HCl after each run and re-equilibrated with Tris buffer. Sensogram data were analyzed using the BIAevluation 3.0 software package. The rate constants were calculated for the binding data using local fitting for the data set as described in the BIAevaluation 3.0 manual with the 1:1 Langmuir binding model.

Results:

Three putative YefM fragments capable of binding GST-YoeB fusion protein were identified in a peptide array using a low stringency procedure (FIG. 6A). A first region comprises three tridecamer peptides (YefM$_{11-23}$-YefM$_{41-27}$) in decreasing binding capacity, which includes the sequence RTISYSEARONLSATMM (the underlined sequence represents a putative binding site; set forth in SEQ ID NO: 129). A second region includes a single YefM$_{33-45}$ peptide sequence, APILIRQNGEAC (set forth in SEQ ID NO: 130). A third region includes the peptides YefM$_{75-87}$ and YefM$_{77-89}$ which cover the MDSIDSLKSGKGTEKD (set forth in SEQ ID NO: 131). In a high stringency procedure the examined sites were extended to include YefM$_{8-31}$ as the first region, YefM$_{29-48}$ as the second region and YefM$_{72-92}$ as the third region. The shift between each arrayed tridecamer peptide was reduced to a single amino acid which resulted in identifying the YefM$_{11-23}$ peptide, having the amino acid sequence set forth in SEQ ID NO: 7, as a sequence containing the antitoxin binding determinant (FIG. 6B).

In replacing the amino acid leucine in position 22 of the YefM$_{11-23}$ peptide to alanine or to glycine only attenuated the binding capacity of GST-YoeB. On the other hand, replacing the amino acid arginine in position 19 of the YefM$_{11-23}$ peptide, with either alanine or glycine (set forth SEQ ID NOs: 8 and 9, respectively) totally negated the binding capacity of the YefM$_{11-23}$ peptide analog with GST-YoeB (FIG. 6C).

Surface plasmon resonance (BIAcore) analysis was used to quantitative determine the affinity between the YoeB toxin and the YefM$_{11-23}$ peptide fragment. The recognition determinant sequence peptides were immobilized onto the sensor chip and the kinetics of GST-YoeB binding and dissociation was estimated at 12.5, 25, and 50 nM concentrations (FIG. 8). According to data analysis, a $k_a$ of $3.06 \times 10^3$ $(M^{-1}s^{-1})$ and a $k_d$ of $1.22 \times 10^3$ $(M^{-1}s^{-1})$ were calculated (arithmetic mean). Accordingly, an equilibrium constant ($K_D$) of 0.4 µM was determined for the YoeB-YefM$_{11-23}$ complex. This dissociation constant is consistent with a specific binding between the toxin and the peptide fragment.

The isolated binding determinant of the YefM antitoxin can be utilized to identify agents capable of preventing or disrupting the YoeB-YefM toxin-antitoxin binding and thereby to induce death of bacteria expressing the YoeB and YefM toxin-antitoxin pair.

It is appreciated that certain features of the invention, which are, for clarity, described in the context of separate embodiments, may also be provided in combination in a single embodiment Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

REFERENCES CITED

Additional References are Cited Hereinabove

1. Anfinsen, C. B. (1973) *Science* 181, 223-230.
2. Schweers, O., Schönbrunn-Hanebeck, E., Marx, A, and Mandelkow, E. (1994) *J. Biol. Chem.* 269, 24290-24297.
3. Uversky, V. N., Gillespie, J. R. and Fink, A. L. (2000) *Proteins Struct. Funct. Genet.* 41, 415-427.
4. Uversky, V. N. (2002) *Prot. Sci.* 11, 739-756.
5. Uversky, V. N. (2002) *Eur. J. Biochem.* 269, 2-12.
6. Dunker, A. K., Lawson, J. D., Brown, C. J. Williams, R. M., Romero, P., Oh, J. S., Oldfield, C. J., Campen, A. M., Ratliff, C. M., Hipps, K. W., Ausio, J., Nissen, M. S., Reeves, R., Kang, C.-H., Kissinger, C. R., Bailey, R. W., Griswold, M. D., Chiu, W., Garner, E. C. and Obradovié, Z. (2001) *J. Mol. Graph. Model.* 19, 26-59.
7. Dobson, C. M. (1999) *Trends Biochem. Sci.* 24, 329-332.
8. Rochet, J. C. and Lansbury, P. T. Jr. (2000) *Curr. Opin. Struct. Biol.* 10, 60-68.
9. Gazit, E. (2002) *Curr. Med. Chem.* 9, 1725-1735.
10. Dunker A. K., Brown, C. J., Lawson, J. D., Iakoucheva, L. M. and Obradovié, Z. (2002) *Biochemistry* 41, 6573-6582.
11. Gazit, E. and Sauer, R. T. (1999) *J. Biol. Chem.* 274, 2652-2657.
12. Lehnherr, H., Maguin, E., Jafri, S. and Yarmolinsky, M. B. (1993) *J. Mol. Biol.* 233, 414-428.
13. Lehnherr, H. and Yarmolinsky, M. B. (1995) *Proc. Natl. Acad. Sci. USA* 92, 3274-3277.
14. Christensen, S. K. and Gerdes, K. (2003) *Mol. Microbiol.* 48, 1389-1400.
15. Pedersen, K., Zavialov, A. V., Pavlov, M. Y., Elf, J., Gerdes, K and Ehrenberg, M. (2003) *Cell* 112, 131-140.
16. Pedersen, K., Christensen, S. K. and Gerdes, K. (2002) *Mol. Microbiol.* 45, 501-510.
17. Christensen, S. K., Mikkelsen, M., Pedersen, K. and Gerdes, K. (2001) *Proc. Natl. Acad. Sci. USA* 98, 14328-14333.
18. Gerdes, K. (2000) *J. Bacteriol* 182, 561-572.
19. Aizenman, E., Engelberg-Kulka, H. and Glaser, G. (1996) *Proc. Natl. Acad. Sci. USA* 93, 6059-6063.
20. Altschul, S. F., Madden, T. L., Schaffer, A. A., Zhang, J., Zhang, Z., Miller, W. and Lipman, D. J. (1997) *Nucleic Acids Res.* 25, 3389-3402.
21. Thompson, J. D., Higgins, D. G. and Gibson, T. J. (1994) *Nucleic Acids Res* 22, 4673-4680.
22. http://prowl.rockefeller.edu/aainfo/masses.htmn.
23. Pomerantsev, A. P., Golovliov, I. R., Ohara, Y., Mokaievich, A. N., Obuchi, M., Norqvist, A., Kuoppa, K. and Pavlov, V. M. (2001) *Plasmid* 46, 210-222.
24. Grady, R. and Hayes, F. (2003) *Mol. Microbiol.* 47, 1419-1432.
25. Jeness, D. D., Sprecher, C. A. and Johnson, W. C. (1976) *Biopolymers* 15, 513-521.
26. Gazit, E. and Sauer, R. T. (1999) *J. Biol. Chem.* 274, 16813-16818.
27. Oberer, M., Lindner, H., Glatter, O., Kratky, C. and Keller, W. (1999) *Biol. Chem.* 380, 1413-1420.
28. Thi, M. H. D., Messens, J., Wyns, L. and Backmann, J. (2000) *J. Mol. Biol.* 299, 1373-1386.
29. Camacho, A. G., Misselwitz, R., Behika, J., Ayora, S., Welfle, K, Meinhart, A., Lara, B., Saenger, W., Welfle, H. and Alonso, J. C. (2002) *Biol. Chem.* 383, 1701-1713.
30. Romero, P., Obradovié, Z., Li, X., Garner, E. C., Brown, C. J. and Dunker, K. (2001) *Proteins Struct. Funct. Genet.* 42, 38-48.
31. Vihinen, M., Torkkcila, E. and Riikonen, P. (1994) *Proteins* 19, 141-149.
32. Radivojac, P., Obradovié, Z., Brown, C. J. and Dunker, A. K. (2003) *Pac. Symp. Biocomput.* 8, 216-227.

---

What is claimed is:

1. A method of identifying a molecule capable of preventing or disrupting binding between a toxin:antitoxin pair produced by a bacterial cell, the method comprising:

(a) exposing toxin and antitoxin polypeptides of a toxin-antitoxin pair produced by the bacterial cell to a plurality of molecules, wherein said toxin polypeptide comprises the amino acid sequence of SEQ ID NO. 77 and said antitoxin polypeptide comprises the amino acid sequence of SEQ ID NO. 76; and (b) determining if the molecule prevents or disrupts binding between said antitoxin and said toxin polypeptides, thereby identifying a molecule capable of preventing or disrupting binding between a toxin:antitoxin pair produced by a bacterial cell.

* * * * *